US007385085B2

(12) United States Patent
John et al.

(10) Patent No.: US 7,385,085 B2
(45) Date of Patent: *Jun. 10, 2008

(54) OXIME DERIVATIVE SUBSTITUTED HYDROXYETHYLAMINE ASPARTYL PROTEASE INHIBITORS

(75) Inventors: Varghese John, San Francisco, CA (US); Michel Maillard, Redwood City, CA (US); Barbara Jagodzinska, Redwood City, CA (US); Jose Aquino, Dale City, CA (US); Gary Probst, San Francisco, CA (US); Jay Tung, Belmont, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 11/177,324

(22) Filed: Jul. 11, 2005

(65) Prior Publication Data

US 2006/0135581 A1 Jun. 22, 2006
US 2007/0149584 A9 Jun. 28, 2007

Related U.S. Application Data

(60) Provisional application No. 60/681,138, filed on May 16, 2005, provisional application No. 60/656,873, filed on Mar. 1, 2005, provisional application No. 60/608,143, filed on Sep. 9, 2004, provisional application No. 60/586,207, filed on Jul. 9, 2004.

(51) Int. Cl.
    C07C 237/04 (2006.01)
(52) U.S. Cl. ..................................... 564/185
(58) Field of Classification Search .................... None
    See application file for complete search history.

(56) References Cited

U.S. PATENT DOCUMENTS

| 4,522,811 | A | 6/1985 | Eppstein et al. |
| 5,145,684 | A | 9/1992 | Liversidge et al. |
| 5,362,912 | A | 11/1994 | Sowin et al. |
| 5,387,742 | A | 2/1995 | Cordell |
| 5,441,870 | A | 8/1995 | Seubert et al. |
| 5,593,846 | A | 1/1997 | Schenk et al. |
| 5,604,102 | A | 2/1997 | McConlogue et al. |
| 5,612,486 | A | 3/1997 | McConlogue et al. |
| 5,696,270 | A | 12/1997 | Kempf et al. |
| 5,720,936 | A | 2/1998 | Wadsworth et al. |
| 5,721,130 | A | 2/1998 | Seubert et al. |
| 5,744,346 | A | 4/1998 | Chrysler et al. |
| 5,766,846 | A | 6/1998 | Schlossmacher et al. |
| 5,811,633 | A | 9/1998 | Wadsworth et al. |
| 5,850,003 | A | 12/1998 | McLonlogue et al. |
| 5,877,015 | A | 3/1999 | Hardy et al. |
| 5,877,399 | A | 3/1999 | Hsiao et al. |
| 5,892,052 | A | 4/1999 | Kempf et al. |
| 5,912,410 | A | 6/1999 | Cordell |
| 5,942,400 | A | 8/1999 | Anderson et al. |
| 6,045,829 | A | 4/2000 | Liversidge et al. |
| 6,150,530 | A | 11/2000 | Kempf et al. |
| 6,191,166 | B1 | 2/2001 | Audia et al. |
| 2004/0044072 | A1 | 3/2004 | Tenbrink et al. |
| 2005/0239790 | A1* | 10/2005 | John et al. ............ 514/252.1 |

FOREIGN PATENT DOCUMENTS

| EP | 0 279 707 A2 | 8/1988 |
| WO | WO 98/22597 | 5/1998 |
| WO | WO 99/64001 | 12/1999 |
| WO | WO 00/17369 | 3/2000 |
| WO | WO 00/47618 | 8/2000 |
| WO | WO 01/10387 | 2/2001 |
| WO | WO 01/23533 | 4/2001 |
| WO | WO 02/02512 | 1/2002 |
| WO | WO02/085877 | 10/2002 |
| WO | WO 02/098849 | 12/2002 |
| WO | WO 02/100399 A1 | 12/2002 |
| WO | WO 02/100820 A1 | 12/2002 |
| WO | WO 03/006021 A1 | 1/2003 |
| WO | WO 03/006423 | 1/2003 |
| WO | WO 03/029169 A2 | 4/2003 |
| WO | WO 03/040096 | 5/2003 |
| WO | WO 03/050073 | 6/2003 |
| WO | WO 03/072535 | 9/2003 |
| WO | WO 2004/024081 | 3/2004 |
| WO | WO 2004/029019 | 4/2004 |
| WO | WO 2004/029019 A2 | 4/2004 |
| WO | WO 2004/043916 A1 | 5/2004 |
| WO | WO 2004/050609 A1 | 6/2004 |
| WO | WO 2004/050619 A1 | 6/2004 |

(Continued)

OTHER PUBLICATIONS

Ajay, et al., "Designing libraries with CNS activity," J. Med. Chem., (1999) 42, 4942-51.

(Continued)

Primary Examiner—Yvonne Eyler
Assistant Examiner—Yaté K Cutliff
(74) Attorney, Agent, or Firm—Finnegan, Henderson, Farabow, Garrett & Dunner, L.L.P.

(57) ABSTRACT

The invention relates to novel compounds and methods of treating diseases, disorders, and conditions associated with amyloidosis. Amyloidosis refers to a collection of diseases, disorders, and conditions associated with abnormal deposition of A-beta protein.

10 Claims, No Drawings

FOREIGN PATENT DOCUMENTS

| WO | WO 2004/069793 A2 | 8/2004 |
|---|---|---|
| WO | WO 2004/094384 A2 | 11/2004 |
| WO | WO 2004/094413 | 11/2004 |
| WO | WO 2004/094413 A1 | 11/2004 |
| WO | WO 2005/014517 | 2/2005 |
| WO | WO 2005/014540 A1 | 2/2005 |
| WO | WO 2005/016876 A2 | 2/2005 |
| WO | WO 2005/058915 A1 | 6/2005 |
| WO | WO 2005/087714 A2 | 9/2005 |
| WO | WO 2005/108358 A2 | 11/2005 |
| WO | WO 2005/108391 A1 | 11/2005 |

OTHER PUBLICATIONS

Albright, J.D., "Synthesis of 1,4,5,6,-Tetrahydropyrazolo[3,4-d]pyrido[3,2-b]azepine," J. Heterocycl. Chem., (2000), 37, 41-6.

Alexakis, A., et al., "A practical, solvent free, one-pot synthesis of C2-symmetrical secondary amines," Tet. Letters, (2004), 45, 1449-1451.

Alvarez, A., et al., "Synthesis of 3-Arylpyrroles and 3-Pyrrolylacetylenes by Palladium-Catalyzed Coupling Reactions", J. Org. Chem., (1992), 57, 1653.

Anderson, G.W., et al., "Studies in Chemotherapy. X. Antithyroid Compounds. Synthesis of 5- and 6- Substituted 2-Thiouracils from b-Oxoesters and Thiourea," J. Am. Chem. Soc., (1945), 67, 2197.

Anzalone, L. and Hirsch, J.A., "Substituent Effects on Hydrogenation of Aromatic Rings: Hydrogenation vs. Hydrogenolysis in Cyclic Analogues of Benzyl Ethers," J. Org. Chem., (1985), 50, 2128.

Beam, C.F., et al., "Preparation of Pyrazoles from the C(a)NN-Trianion of Hyrdrazones having an a-Hydrogen Atom," J. Chem. Soc., Section C: Organic (1971), 9, 1658-1660.

Becker, D.P. & Flynn, D.L., "A Short Synthesis of 1-Azaadamantan-4-one and the 4r and 4s Isomers of 4-Amino-1-azaadamantane," Synthesis, (1992), 1080.

Benedetti, et al., "Versatile and Stereoselective Synthesis of Diamino Diol Dipeptide Isosteres, Core Units of Psuedopeptide HIV Protease Inhibitors," J. Org. Chem., (1997), 62, 9348-9353.

Boeckman, R. K., Jr.; Liu, X., "Controllable Monoaddition of Carbon Nucleophiles to 1,2,3,4-Diepoxybutane: Two-directional Chain Extension of a C2 Symmetric Four Carbon Diepoxide as a Route to Differentiated Syn 1,2-Diols," Synthesis, (2002), 2138-2142.

Castro, B., et al., "Reactifs de Couplage Peptidique IV (1)—L'Hexaflourophosphate De Benzotriazolyl N-Oxytrisdimethylamino Phosphonium (B.O.P.)," Tet. Letters, (1975), 14, 1219-1222.

Cerri, A., et al., "17beta-O-Aminoalkyloximes of 5beta-androstane-3beta,14beta-diol with digitalis-like activity: synthesis, cardiotonic activity, structure-activity relationships, and molecular modeling of the Na(+),K(+)-ATPase receptor.," J. Med. Chem.; 2000, 43, 2332-2349.

Citron, et al., "Mutation of the B-amyloid precursor protein in familial Alzheimer's disease increases B-protein production," Nature, (1992), 360:672-674.

Coria F. and Rubio, I., "Cerebral amyloid angiopathies," Neuropath Appl. Neurobiol., (1996) 22, 216-227.

Cornelius, L.A.M.; Combs, D.W., "A Convenient Synthesis of Mono- and Polyhalogenated Benzocyclanones," Synthetic Communications, (1994), 24, 2777-2788.

Dai, C. and Fu, G.J., "The first general method for palladium-catalyzed Negishi cross-coupling of aryl and vinyl chlorides: use of commercially available Pd(P(t-Bu)(3))(2) as a catalyst," J. Am. Chem. Soc., (2001), 123, 2719-2724.

Dantzig, A.H., et al., "Reversal of P-glycoprotein-mediated multidrug resistance by a potent cyclopropyldibenzosuberane modulator, LY335979," Cancer Research, (1996), 56, 4171-4179.

Dovey, et al., "Functional gamma-secretase inhibitors reduce beta-amyloid peptide levels in brain," J. Neurochemistry, (2001), 76:173-171.

Emilien, G., et al., "Prospects for Pharmacological Intervention in Alzheimer Disease," Arch. Neurol. (2000), 57:454-459.

Ertl, P., et al., "Fast calculation of molecular polar surface area as a sum of fragment-based contributions and its application to the prediction of drug transport properties," J. Med. Chem., (2000), 43:3714-17.

Fujita, T., et al., "A new substituent constant, ¼, derived from partition coefficient" J. Am. Chem. Soc., (1964), 86, 5157.

Games, et al., "Alzheimer-type neuropathology in transgenic mice overexpressing V717F beta-amyloid precursor protein," Nature, (1995), 373:523-527.

Gibaldi, M. and Perrier, D., Pharmacokinetics, 2nd Ed., 1982, Marcel Dekker Inc., New York, NY, pp. 409-418.

Gilzinsky, A.G., et al., "On the relative power of electophilic fluorinating reagents of the N-F class," J. Fluorine Chemistry, 59, (1992), 157-162.

Hall, J.H., Gisler, M., "A simple method for converting nitriles to amides. Hydrolysis with potassium hydroxide in tert-butyl alcohol," J. Org Chem. (1976), 41, 3769-3770.

Hardy, J., "Framing beta-amyloid," Nature Genet, (1992) 1:233-234.

Harnden, M.R., et al., "Synthesis and antiviral activity of 9-alkoxypurines. 1. 9-(3-Hydroxypropoxy)- and 9-[3-hydroxymethyl)propoxy]purines," J. Med. Chem., (1990), 33, 187-196.

Holy, A., et al., "6-[2-Phosphonomethoxy) alkoxy]pyrimidines with antiviral activity," J. Med. Chem., (2002), 45, 1918-1929.

Huo, S., "Highly efficient, general procedure for the preparation of alkylzinc reagents from unactivated alkyl bromides and chlorides," Org. Lett., (2003), 423.

Hussain, et al., "Identification of a novel aspartic protease (Asp 2) as beta-secretase," Mol. Cell. Neurosci. (1999), 14:419-427.

Hyafil, F., et al., "In vitro and in vivo reversal of multidrug resistance by GF120918, an acridonecarboxamide derivative," Cancer Research, (1993), 53, 4595-4602.

Jones, T.K., et al., "An asymmetric synthesis of MK-0417. Observations on Oxazaborolidine-catalyzed reductions," J. Org. Chem. (1991), 56, 763-769.

Kabalka, G.W., et al., "Tosylation of alcohols," J. Org. Chem., (1986), 51, 2386-2388.

Kaiho, T., et al., "Cardiotonic agents. 1-Methyl-7-(4-pyridyl)-5,6,7,8-tetrahydro-3 (2H)-isoquinolinones and related compounds. Synthesis and activity," J. Med. Chem., (1989), 32(2), 351-357.

Kang, et al., "Synthesis of 1,4-Diaminocyclitols from L-serine Methyl Ester," J. Org. Chem., (1996), 61, 5528-5531.

Kang, et al., "The precursor of Alzheimer's disease amyloid A4 protein resembles a cell-surface receptor,"Nature (1987), 325:733-6.

Katritzky, A.R. et al., Comprehensible Heterocyclic Chemistry: The Structure, Reactions and Synthesis and Use of Heterocyclic Compounds, vol. 1-8, New York: Pergamon Press, 1984.

Kempf, et al., "Symmetry-based inhibitors of HIV protease. Structure-activity studies of acylated 2,4-diamino-1,5-diphenyl-3-hydroxypentane and 2,5-diamino-1,6-diphenylhexane-3,4-diol," J. Med. Chem., (1993), 36, 320-330.

Kikugawa, Y., et al., "N-Methoxydiacetamide: A New Selective Acetylating Agent," Tet. Letters, (1990), 31, 243-246.

Kim, J.T. and Gevorgyan, V., "Double cycloisomerization as a novel and expeditious route to tricyclic heteroaromatic compounds: short and highly diastereoselective synthesis of (+/−)-tetraponerine T6," Org. Lett., (2002), 4, 4697-4669.

Kimura, T., et al., "Strategy for the synthesis of large peptides: an application to the total synthesis of human parathyroid hormone [hPTH (1-84)]," Biopolymers, (1981), 20, 1823-1832.

Kitaguchi, et al., "Novel precursor of Alzheimer's disease amyloid protein shows protease inhibitory activity," Nature (1981), 331:530-532.

Knight, S.D. and Overman, L.E., "Preparation of Spirocyclic Polyethers by Intramolecular Heck Reactions," Heterocycles, (1994), 39, 497.

Knochel, P., et al., "Organozinc Mediated Reactions," Tetrahedron, (1998), 54, 8275-8319.

Kocieski, P.J., Protecting Groups, Stuttgart, FRG: G. T. Verlag 1994.

Kurihara, M., et al., "Stereoselective Synthesis of an Erythro N-protected alpha-Amino Epoxide Derivative," Tetrahedron Letters (1999), 40, 3183-3184.

Lang, F., et al., Amination of aryl halides using copper catalysis, Tet. Letters; (2001), 42, 3251-3254.

Larock, R.C., Comprehensive Organic Transformations, VCH Publishers, 1989, p. 981, 979 & 972.

Larock, R.C., Comprehensive Organic Transformations, Wiley-VCH Publishers, 1999, 2d Ed. pp. 1942-1943, 1953-1955, 1955.

Lee, et al., "Development of a New Type of Protease Inhibitors, Efficacious against FIV and HIV Variants," J. Am. Chem. Soc., (1999), 121, 1145-1155.

Lin, et al., "Human aspartic protease memapsin 2 cleaves the beta-secretase site of beta-amyloid precursor protein," Proceedings Nat'l Acad. Sciences USA (2000) 97:1456-1460.

Lipinski, C.A., et al., "Experimental and computational approaches to estimate solubility and permeability in drug delivery and development settings," Adv. Drug Deliv. Reviews, (1997) 23:3-25.

Liu, G., et al., "Synthesis of Enantiomerically Pure N-tert-Butanesulfinyl Imines (tert-Butanesulfinimines) by the Direct Condensation of tert-Butanesulfinamide with Aldehydes and Ketones," J. Org. Chem., (1999), 64, 1278-1284.

Luly, J.R., et al., "A synthesis of protected aminoalkyl epoxides from a-amino acids," J. Org. Chem., (1987), 52, 1487.

McMahon, J.P. and Ellman, J.A., "Highly stereoselective addition of organometallic reagents to N-tert-butanesulfinyl imines derived from 3- and 4- substituted cyclohexanones," Org. Lett. (2004), 6, 1645-1647.

Negishi, E.I., et al., "A convenient synthesis of unsymmetrical bibenzyls, homoallylarenes, and homopropargylarenes via palladium-catalyzed cross coupling," Tet. Letters, (1983), 24, 3823-3824.

Njar, V.C.O.; "High-Yield Synthesis of Novel Imidazoles and Triazoles from Alcohols and Phenols," Synthesis; (2000); 14; 2019-2028.

Orito, K., et al., Synthesis of 5-Iodobenzofurans and 6-Iodobenzopyrans via Direct Iodination with Mercury(II) Oxide-Iodine Reagent, Synthesis, (1997), 23-25.

Ornstein, P.L., et al., "4-(Tetrazolylalkyl)piperidine-2-carboxylic acids. Potent and selective N-methyl-D-aspartic acid receptor antagonists with a short duration of action," J. Med. Chem. (1991), 34, 90-97.

Padhy, A., et al. "Synthesis and anti-microbial activity of some pyrimidine derivatives," Int. J. Pharm., 42B(4), 910-915, (2003) Section B: Organic Chemistry Including Medicinal Chemistry.

Pirttila, et al., "Longitudinal study of cerebrospinal fluid amyloid proteins and apolipoprotein E in patients with probable Alzheimer's disease," Neuro. Lett. (1998) 249:21-4.

Rogers, G.A. and Bruice, T.C., "Synthesis and evaluation of a model for the so-called "charge-relay" system of the serine esteras," J. Am. Chem. Soc., (1974), 96, 2463-2472.

Rover, S., et al., "High-affinity, non-peptide agonists for the ORL1 (orphanin FQ/nociceptin) receptor,"J. Med. Chem., (2000), 43, 1329-1338.

Saito, M., et al., "Synthesis and immumological activity of 5,6,6a,8,9,11a-hexahydronaphth[1',2':4,5]imidazol[2,1-b]thiazoles and 5,6,6a,9,10,11a-hexahydroanaphth[2',1':4,5]imidazol[2,1-b]thiazoles," J. Med. Chem., (1980), 23, 1364-1372.

Satoh, Y. and Marcopulos, N., "Application of 5-Lithiotetrazoles in Organic Synthesis," Tet. Letters (1995), 36, 1759-1762.

Scott, W.J., et al., "Palladium-catalyzed coupling of vinyl triflates with organostannanes: 4-tert-Butyl-1-Vinylcyclohexene and 1-(4-tert-Butylcyclohexen-1-YL)-2-Propen-1-one," Org. Syn.; (1983); Coll. vol. 8; 97-103.

Selkoe, "The molecular pathology of Alzheimer's disease," Neuron (1991), 6:487.

Seubert, et al., "Isolation and quantification of soluble Alzheimer's beta-peptide from biological fluids," Nature (1992), 359:325-327.

Sinha, et al., "Purification and cloning of amyloid precursor protein -secretase from human brain," Nature (1999), 402:501, 537-554.

Takechi, H., et al., "Screening Search for Organic Florophores: Syntheses and Fluorescence Properties of 3-Azolyl-7-diethylaminocoumarin Derivatives," Chem. Pharm. Bull. (2000), 48, 1702-1710.

Tao, B. and Timberlake, J.W., "Synthesis of Conformationally Constrained Spirohydantoins with a Dibenzo[a,d]heptadiene Ring," Synthesis; (2000); 10; 1449-1453.

Tucker, T.J., et al., "A series of potent HIV-1 protease inhibitors containing a hydroxyethyl secondary amine transition state isostere: synthesis, enzyme inhibition, and antiviral activity," J. Med. Chem., (1992), 35, 2525.

Vassar, et al., "Beta-Secretase Cleavage of Alzheimer's Amyloid Precursor Protein by the Transmembrane Aspartic Protease BACE," Science, (1999), 286:735-741.

Witherspoon, S.M., et al., "Flow Cytometric Assay of Modulation of P-Glycoprotein Function in Whole Blood by the Multidrug Resistance Inhibitor GG918," Clin. Cancer Res., (1996), 2, 7-12.

Yan, et al.,"Membrane-anchored aspartyl protease with Alzheimer's disease beta-secretase activity," Nature, (1999), 402:533-537.

Zuccarello, et al., "HIV-1 Protease Inhibitors Based on Acyclic Carbohydrates," J. Org. Chem., (1998), 63, 4898-4906.

Mauleon et al., "Synthesis and B-Adrenergic Antagonism of 2-(Aryloxy)-1-(2-piperidyl)ethanolis," J. Med. Chem. (1988), 31, 2122-2126.

Xiao-Yi et al., "Solid-Phase Synthesis of Alkyl Aryl Ethers via the Ullmann Condensation," J. Comb. Chem. (2002), 4, 536-539.

Copending U.S. Appl. No. 11/546,347, filed Oct. 12, 2006, published Jun. 28, 2007.

Copending U.S. Appl. No. 11/546,453, filed Oct. 12, 2006, published Jun. 28, 2007.

Copending U.S. Appl. No. 11/038,790, filed Jan. 21, 2005, published Jan. 19, 2006.

Copending U.S. Appl. No. 11/074,828, filed Mar. 9, 2005, published Oct. 27, 2005.

Copending U.S. Appl. No. 11/075,292, filed Mar. 9, 2005, published Nov. 24, 2005.

Copending U.S. Appl. No. 11/075,294, filed Mar. 9, 2005, published Oct. 27, 2005.

Copending U.S. Appl. No. 11/075,312, filed Mar. 9, 2005, published Oct. 27, 2005.

Copending U.S. Appl. No. 11/075,445, filed Mar. 9, 2005, published Jan. 19, 2006.

Copending U.S. Appl. No. 11/177,348, filed Jul. 11, 2005, published Jun. 15, 2006.

Copending U.S. Appl. No. 11/211,484, filed Aug. 26, 2005, published Apr. 6, 2006.

Copending U.S. Appl. No. 11/659,788, filed Feb. 9, 2007.

* cited by examiner

SEQUENCE LISTING

<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Met Asp Ala
 1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Leu Asp Ala
 1

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Covalent attachment of Oregon green at Cys
      residue

<400> SEQUENCE: 3

Ser Glu Val Asn Leu Asp Ala Glu Phe Arg Cys Lys Lys
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Covalent attachment of Oregon green at Cys
      residue

<400> SEQUENCE: 4

Ser Glu Val Lys Met Asp Ala Glu Phe Arg Cys Lys Lys
 1               5                  10

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (20)
<223> OTHER INFORMATION: Covalent attachment of Oregon green at Cys
      residue

<400> SEQUENCE: 5

Gly Leu Asn Ile Lys Thr Glu Glu Ile Ser Glu Ile Ser Tyr Glu Val
 1               5                  10                  15

Glu Phe Arg Cys Lys Lys
            20

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (32)
<223> OTHER INFORMATION: Covalent attachment of Oregon green at Cys
      residue

<400> SEQUENCE: 6

Ala Asp Arg Gly Leu Thr Thr Arg Pro Gly Ser Gly Leu Thr Asn Ile
 1               5                  10                  15

Lys Thr Glu Glu Ile Ser Glu Val Asn Leu Asp Ala Glu Phe Arg Cys
            20                  25                  30

Lys Lys

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Oxidized Cys
<220> FEATURE:
<221> NAME/KEY: MOD_RES
<222> LOCATION: (19)
<223> OTHER INFORMATION: Oxidized Cys
<220> FEATURE:
<221> NAME/KEY: MOD_RES
<222> LOCATION: (31)
<223> OTHER INFORMATION: Covalent attachment of Oregon green at Cys
      residue

<400> SEQUENCE: 7

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Ala Cys Lys
            20                  25                  30

Lys

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

-continued

Cys Gly Gly Ala Asp Arg Gly Leu Thr Thr Arg Pro Gly Ser Gly Leu
 1               5                  10                  15

Thr Asn Ile Lys Thr Glu Glu Ile Ser Glu Val Asn Leu Asp Ala Glu
            20                  25                  30

Phe

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Gly Gly Ala Asp Arg Gly Leu Thr Thr Arg Pro Gly Ser Gly Leu
 1               5                  10                  15

Thr Asn Ile Lys Thr Glu Glu Ile Ser Glu Val Asn Leu
            20                  25

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Glu Val Asn Leu Asp Ala Glu Phe
 1               5

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Asp Arg Gly Leu Thr Thr Arg Pro Gly Ser Gly Leu Thr Asn Ile
 1               5                  10                  15

Lys Thr Glu Glu Ile Ser Glu Val Asn Leu Asp Ala Glu Phe
            20                  25                  30

OXIME DERIVATIVE SUBSTITUTED HYDROXYETHYLAMINE ASPARTYL PROTEASE INHIBITORS

CROSS-REFERENCE TO RELATED APPLICATIONS

This application claims the benefit of priority under 35 U.S.C. § 119(e) to U.S. Provisional Application 60/586,207, filed Jul. 9, 2004, U.S. Provisional Application 60/608,143, filed Sep. 9, 2004, U.S. Provisional Application 60/656,873, filed Mar. 1, 2005, and U.S. Provisional Application 60/681,138, filed May 16, 2005, incorporated herein by reference in full.

FIELD OF THE PRESENT INVENTION

The present invention is directed to novel compounds and also to methods of treating at least one condition, disorder, or disease associated with amyloidosis using such compounds.

BACKGROUND OF THE PRESENT INVENTION

Amyloidosis refers to a collection of conditions, disorders, and diseases associated with abnormal deposition of amyloidal protein. For instance, Alzheimer's disease is believed to be caused by abnormal deposition of amyloidal protein in the brain. Thus, these amyloidal protein deposits, otherwise known as amyloid-beta peptide, A-beta, or betaA4, are the result of proteolytic cleavage of the amyloid precursor protein (APP).

The majority of APP molecules that undergo proteolytic cleavage are cleaved by the aspartyl protease alpha-secretase. Alpha-secretase cleaves APP between Lys687 and Leu688 producing a large, soluble fragment, alpha-sAPP, which is a secreted form of APP that does not result in beta-amyloid plaque formation. The alpha-secretase cleavage pathway precludes the formation of A-beta, thus providing an alternate target for preventing or treating amyloidosis.

Some APP molecules, however, are cleaved by a different aspartyl protease known as beta-secretase which is also referred to in the literature as BACE, BACE1, Asp2, and Memapsin2. Beta-secretase cleaves APP after Met671, creating a C-terminal fragment. See, for example, Sinha et al., Nature, (1999), 402:537-554 and published PCT application WO 00/17369. After cleavage of APP by beta-secretase, an additional aspartyl protease, gamma-secretase, may then cleave the C-terminus of this fragment, at either Val711 or Ile713, (found within the APP transmembrane domain), generating an A-beta peptide. The A-beta peptide may then proceed to form beta-amyloid plaques. A detailed description of the proteolytic processing of APP fragments is found, for example, in U.S. Pat. Nos. 5,441,870, 5,721,130, and 5,942,400.

The amyloidal disease Alzheimer's is a progressive degenerative disease that is characterized by two major pathologic observations in the brain which are (1) neurofibrillary tangles, and (2) beta-amyloid (or neuritic) plaques. A major factor in the development of Alzheimer's disease is A-beta deposits in regions of the brain responsible for cognitive activities. These regions include, for example, the hippocampus and cerebral cortex. A-beta is a neurotoxin that may be causally related to neuronal death observed in Alzheimer's disease patients. See, for example, Selkoe, Neuron, 6 (1991) 487. Since A-beta peptide accumulates as a result of APP processing by beta-secretase, inhibiting beta-secretase's activity is desirable for the treatment of Alzheimer's disease.

Dementia-characterized disorders also arise from A-beta accumulation in the brain including accumulation in cerebral blood vessels (known as vasculary amyloid angiopathy) such as in the walls of meningeal and parenchymal arterioles, small arteries, capillaries, and venules. A-beta may also be found in cerebrospinal fluid of both individuals with and without Alzheimer's disease. Additionally, neurofibrillary tangles similar to the ones observed in Alzheimer's patients can also be found in individuals without Alzheimer's disease. In this regard, a patient exhibiting symptoms of Alzheimer's due to A-beta deposits and neurofibrillary tangles in their cerebrospinal fluid may in fact be suffering from some other form of dementia. See, for example, Seubert et al., Nature, 359 (1992) 325-327. Examples of other forms of dementia where A-beta accumulation generates amyloidogenic plaques or results in vascular amyloid angiopathy include Trisomy 21 (Down's Syndrome), Hereditary Cerebral Hemorrhage with amyloidosis of the Dutch-Type (HCHWA-D), and other neurodegenerative disorders. Consequently, inhibiting beta-secretase is not only desirable for the treatment of Alzheimer's, but also for the treatment of other conditions associated with amyloidosis.

Amyloidosis is also implicated in the pathophysiology of stroke. Cerebral amyloid angiopathy is a common feature of the brains of stroke patients exhibiting symptoms of dementia, focal neurological syndromes, or other signs of brain damage. See, for example, Corio et al., Neuropath Appl. Neurobiol., 22 (1996) 216-227. This suggests that production and deposition of A-beta may contribute to the pathology of Alzheimer's disease, stroke, and other diseases and conditions associated with amyloidosis. Accordingly, the inhibition of A-beta production is desirable for the treatment of Alzheimer's disease, stroke, and other diseases and conditions associated with amyloidosis.

Presently there are no known effective treatments for preventing, delaying, halting, or reversing the progression of Alzheimer's disease and other conditions associated with amyloidosis. Consequently, there is an urgent need for methods of treatment capable of preventing and treating conditions associated with amyloidosis including Alzheimer's disease.

Likewise, there is a need for methods of treatment using compounds that inhibit beta-secretase-mediated cleavage of APP. There is also a need for methods of treatment using compounds that are effective inhibitors of A-beta production, and/or are effective at reducing A-beta deposits or plaques, as well as methods of treatment capable of combating diseases and conditions characterized by amyloidosis, or A-beta deposits, or plaques.

There is also a need for methods of treating conditions associated with amyloidosis using compounds that are efficacious, bioavailable and/or selective for beta-secretase. An increase in efficacy, selectivity, and/or oral bioavailability may result in preferred, safer, less expensive products that are easier for patients to use.

There is also a need for methods of treating at least one condition associated with amyloidosis using compounds with characteristics that would allow them to cross the blood-brain-barrier. Desirable characteristics include a low molecular weight and a high log P (increased log P=increased lipophilicity).

Generally, known aspartyl protease inhibitors are either incapable of crossing the blood-brain barrier or do so with great difficulty. These compounds are unsuitable for the treatment of the conditions described herein. Accordingly, there is a need for methods of treating at least one condition associated with amyloidosis using compounds that can readily cross the blood-brain barrier and inhibit beta-secretase.

There is also a need for a method of finding suitable compounds for inhibiting beta-secretase activity, inhibiting cleavage of APP, inhibiting production of A-beta, and/or reducing A-beta deposits or plaques.

The present invention is directed to novel compounds and also to methods of treating at least one condition, disorder, or disease associated with amyloidosis using such compounds. An embodiment of the present invention is compounds of formula (I) or at least one pharmaceutically acceptable salt thereof, wherein $R_1$, $R_2$, and $R_C$ are defined below. Another embodiment of the present invention is a method of administering at least one compound of formula (I) or at least one pharmaceutically acceptable salt thereof, wherein $R_1$, $R_2$, and $R_C$ are defined below, in treating at least one condition, disorder, or disease associated with amyloidosis. Another embodiment is directed to methods of treatment comprising administering at least one compound of formula (I) or at least one pharmaceutically acceptable salt thereof, wherein $R_1$, $R_2$, and $R_C$ are defined below, useful in preventing, delaying, halting, or reversing the progression of Alzheimer's disease.

Another embodiment of the present invention is directed to uses of beta-secretase inhibitors of at least one compound of formula (I) or at least one pharmaceutically acceptable salt thereof, wherein $R_1$, $R_2$, and $R_C$ are defined below, in treating or preventing at least one condition, disorder, or disease associated with amyloidosis.

Another embodiment of the present invention is the administration of beta-secretase inhibitors of at least one compound of formula (I) or at least one pharmaceutically acceptable salt thereof, wherein $R_1$, $R_2$, and $R_C$ are defined below, exhibiting at least one property chosen from improved efficacy, bioavailability, selectivity, and blood-brain barrier penetrating properties. The present invention accomplishes one or more of these objectives and provides further related advantages.

BRIEF SUMMARY OF THE PRESENT INVENTION

The present invention is directed to novel compounds and also to methods of treating at least one condition, disorder, or disease associated with amyloidosis using such compounds. The present invention is directed to compounds of formula (I) or at least one pharmaceutically acceptable salt thereof, wherein $R_1$, $R_2$, and $R_C$ are defined below, and methods of treating at least one condition, disorder, or disease associated with amyloidosis. As previously noted, amyloidosis refers to a collection of diseases, disorders, and conditions associated with abnormal deposition of A-beta protein.

An embodiment of the present invention is to provide compounds having properties contributing to viable pharmaceutical compositions. These properties include improved efficacy, bioavailability, selectivity, and/or blood-brain barrier penetrating properties. They can be interrelated, though an increase in any one of them correlates to a benefit for the compound and its corresponding method of treatment. For example, an increase in any one of these properties may result in preferred, safer, less expensive products that are easier for patients to use.

Accordingly, an embodiment of the present invention is to provide compounds of formula (I),

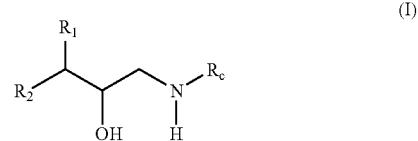

or pharmaceutically acceptable salts thereof, wherein $R_1$, $R_2$, and $R_C$ are defined below.

Another embodiment of the present invention is a method of preventing or treating at least one condition that benefits from inhibition of at least one aspartyl-protease, comprising administering to a host a composition comprising a therapeutically effective amount of at least one compound of formula (I),

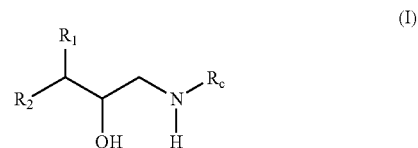

or at least one pharmaceutically acceptable salt thereof, wherein $R_1$, $R_2$, and $R_C$ are defined below.

Another embodiment is to provide selective compounds of formula (I),

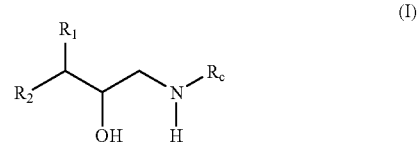

or pharmaceutically acceptable salts thereof, wherein $R_1$, $R_2$, and $R_C$ are defined below.

Another embodiment is to provide efficacious compounds of formula (I),

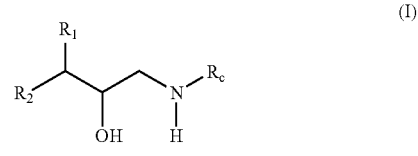

or pharmaceutically acceptable salts thereof, wherein the inhibition is at least 10% for a dose of about 100 mg/kg or less, and wherein $R_1$, $R_2$, and $R_C$ are defined below.

Another embodiment is to provide orally bioavailable compounds of formula (I),

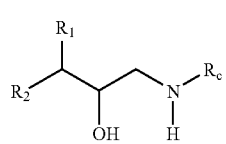

or pharmaceutically acceptable salts thereof, wherein said compound has an F value of at least 10%, and wherein $R_1$, $R_2$, and $R_C$ are defined below.

Another embodiment of the present invention provides a method for preventing or treating at least one condition that benefits from inhibition of at least one aspartyl-protease, comprising administering to a host at least one compound of formula (I), or pharmaceutically acceptable salts thereof, wherein the inhibition is at least 10% for a dose of 100 mg/kg or less, and wherein $R_1$, $R_2$, and $R_C$ are defined below.

Another embodiment of the present invention provides a method for preventing or treating at least one condition that benefits from inhibition of at least one aspartyl-protease, comprising administering to a host a composition comprising a therapeutically effective amount of at least one compound of formula (I), or pharmaceutically acceptable salts thereof, wherein $R_1$, $R_2$, and $R_C$ are as defined below.

Another embodiment of the present invention provides a method of preventing or treating at least one condition that benefits from inhibition of at least one aspartyl-protease, comprising administering to a host a composition comprising a therapeutically effective amount of at least one compound of formula (I), or pharmaceutically acceptable salts thereof, wherein the inhibition is at least 10% for a dose of 100 mg/kg or less, and wherein $R_1$, $R_2$, and $R_C$ are as defined below.

Another embodiment provides a method of preventing or treating at least one condition that benefits from inhibition of beta-secretase, comprising administering to a host a composition comprising a therapeutically effective amount of at least one compound of formula (I), or pharmaceutically acceptable salts thereof, wherein the inhibition is at least 10% for a dose of 100 mg/kg or less, and wherein $R_1$, $R_2$, and $R_C$ are as defined below.

In another embodiment, the present invention provides a method for preventing or treating at least one condition associated with amyloidosis, comprising administering to a patient in need thereof a therapeutically effective amount of at least one compound of formula (I), or at least one pharmaceutically acceptable salt thereof, the compound having an F value of at least 10%, wherein $R_1$, $R_2$, and $R_C$ are as defined below.

In another embodiment, the present invention provides a method of preventing or treating at least one condition associated with amyloidosis, comprising administering to a host a composition comprising a therapeutically effective amount of at least one selective beta-secretase inhibitor of formula (I), or pharmaceutically acceptable salt thereof, wherein $R_1$, $R_2$, and $R_C$ are as defined below.

In another embodiment, the present invention provides a method of preventing or treating Alzheimer's disease by administering to a host an effective amount of at least one compound of formula (I), or at least one pharmaceutically acceptable salt thereof, wherein $R_1$, $R_2$, and $R_C$ are as defined below.

In another embodiment, the present invention provides a method of preventing or treating dementia by administering to a host an effective amount of at least one compound of formula (I), or pharmaceutically acceptable salt thereof, wherein $R_1$, $R_2$, and $R_C$ are as defined below.

In another embodiment, the present invention provides a method of inhibiting beta-secretase activity in a host, the method comprising administering to the host an effective amount of at least one compound of formula (I), or at least one pharmaceutically acceptable salt thereof, wherein $R_1$, $R_2$, and $R_C$ are as defined below.

In another embodiment, the present invention provides a method of inhibiting beta-secretase activity in a cell, the method comprising administering to the cell an effective amount of at least one compound of formula (I), or at least one pharmaceutically acceptable salt thereof, wherein $R_1$, $R_2$, and $R_C$ are as defined below.

In another embodiment, the present invention provides a method of inhibiting beta-secretase activity in a host, the method comprising administering to the host an effective amount of at least one compound of formula (I), or at least one pharmaceutically acceptable salt thereof, wherein the host is a human, and wherein $R_1$, $R_2$, and $R_C$ are as defined below.

In another embodiment, the present invention provides a method of affecting beta-secretase-mediated cleavage of amyloid precursor protein in a patient, comprising administering a therapeutically effective amount of at least one compound of formula (I), or at least one pharmaceutically acceptable salt thereof, wherein $R_1$, $R_2$, and $R_C$ are as defined below.

In another embodiment, the present invention provides a method of inhibiting cleavage of amyloid precursor protein at a site between Met596 and Asp597 (numbered for the APP-695 amino acid isotype), or at a corresponding site of an isotype or mutant thereof, comprising administering a therapeutically effective amount of at least one compound of formula (I), or at least one pharmaceutically acceptable salt thereof, wherein $R_1$, $R_2$, and $R_C$ are as defined below.

In another embodiment, the present invention provides a method of inhibiting production of A-beta, comprising administering to a patient a therapeutically effective amount of at least one compound of formula (I), or at least one pharmaceutically acceptable salt thereof, wherein $R_1$, $R_2$, and $R_C$ are as defined below.

In another embodiment, the present invention provides a method of preventing or treating deposition of A-beta, comprising administering a therapeutically effective amount of at least one compound of formula (I), or at least one pharmaceutically acceptable salt thereof, wherein $R_1$, $R_2$, and $R_C$ are as defined below.

In another embodiment, the present invention provides a method of preventing, delaying, halting, or reversing a disease characterized by A-beta deposits or plaques, comprising administering a therapeutically effective amount of at least one compound of formula (I), or at least one pharmaceutically acceptable salt thereof, wherein $R_1$, $R_2$, and $R_C$ are as defined below.

In another embodiment, the A-beta deposits or plaques are in a human brain.

In another embodiment, the present invention provides a method of inhibiting the activity of at least one aspartyl protease in a patient in need thereof, comprising administering a therapeutically effective amount of at least one compound of formula (I), or at least one pharmaceutically acceptable salt thereof, wherein $R_1$, $R_2$, and $R_C$ are as defined below.

In another embodiment, the at least one aspartyl protease is beta-secretase.

In another embodiment, the present invention provides a method of interacting an inhibitor with beta-secretase, comprising administering to a patient in need thereof a therapeutically effective amount of at least one compound of formula (I), or at least one pharmaceutically acceptable salt thereof, wherein $R_1$, $R_2$, and $R_C$ are as defined below, wherein the at least one compound interacts with at least one beta-secretase subsite such as S1, S1', or S2'.

In another embodiment, the present invention provides an article of manufacture, comprising (a) at least one dosage form of at least one compound of formula (I), or pharmaceutically acceptable salt thereof, wherein $R_1$, $R_2$, and $R_C$ are defined below, (b) a package insert providing that a dosage form comprising a compound of formula (I) should be administered to a patient in need of therapy for at least one disorder, condition or disease associated with amyloidosis, and (c) at least one container in which at least one dosage form of at least one compound of formula (I) is stored.

In another embodiment, the present invention provides a packaged pharmaceutical composition for treating at least one condition related to amyloidosis, comprising (a) a container which holds an effective amount of at least one compound of formula (I), or at least one pharmaceutically acceptable salt thereof, wherein $R_1$, $R_2$, and $R_C$ are as defined below, and (b) instructions for using the pharmaceutical composition.

DEFINTIONS

Throughout the specification and claims, including the detailed description below, the following definitions apply.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different.

APP, amyloid precursor protein, is defined as any APP polypeptide, including APP variants, mutations, and isoforms, for example, as disclosed in U.S. Pat. No. 5,766,846.

Beta-amyloid peptide (A-beta peptide) is defined as any peptide resulting from beta-secretase mediated cleavage of APP, including, for example, peptides of 39, 40, 41, 42, and 43 amino acids, and extending from the beta-secretase cleavage site to amino acids 39, 40, 41, 42, or 43.

Beta-secretase is an aspartyl protease that mediates cleavage of APP at the N-terminus edge of A-beta. Human beta-secretase is described, for example, in WO 00/17369.

The term "complex" as used herein refers to an inhibitor-enzyme complex, wherein the inhibitor is a compound of formula (I) described herein and wherein the enzyme is beta-secretase or a fragment thereof.

The term "host" as used herein refers to a cell or tissue, in vitro or in vivo, an animal, or a human.

The term "treating" refers to administering a compound or a composition of formula (I) to a host having at least a tentative diagnosis of disease or condition. The methods of treatment and compounds of the present invention will delay, halt, or reverse the progression of the disease or condition thereby giving the host a longer and/or more functional life span.

The term "preventing" refers to administering a compound or a composition of formula (I) to a host who has not been diagnosed as having the disease or condition at the time of administration, but who could be expected to develop the disease or condition or be at increased risk for the disease or condition. The methods of treatment and compounds of the present invention may slow the development of disease symptoms, delay the onset of the disease or condition, halt the progression of disease development, or prevent the host from developing the disease or condition at all. Preventing also includes administration of at least one compound or a composition of the present invention to those hosts thought to be predisposed to the disease or condition due to age, familial history, genetic or chromosomal abnormalities, due to the presence of one or more biological markers for the disease or condition, such as a known genetic mutation of APP or APP cleavage products in brain tissues or fluids, and/or due to environmental factors.

The term "halogen" in the present invention refers to fluorine, bromine, chlorine, or iodine.

The term "alkyl" in the present invention refers to straight or branched chain alkyl groups having 1 to 20 carbon atoms. An alkyl group may optionally comprise at least one double bond and/or at least one triple bond. The alkyl groups herein are unsubstituted or substituted in one or more positions with various groups. For example, such alkyl groups may be optionally substituted with at least one group independently selected from alkyl, alkoxy, —C(O)H, carboxy, alkoxycarbonyl, cycloalkyl, heterocycloalkyl, aryl, heteroaryl, amido, alkanoylamino, amidino, alkoxycarbonylamino, N-alkyl amidino, N-alkyl amido, N,N'-dialkylamido, aralkoxycarbonylamino, halogen, alkyl thio, alkylsulfinyl, alkylsulfonyl, hydroxy, cyano, nitro, amino, monoalkylamino, dialkylamino, haloalkyl, haloalkoxy, aminoalkyl, monoalkylaminoalkyl, dialkylaminoalkyl, and the like. Additionally, at least one carbon within any such alkyl may be optionally replaced with —C(O)—.

Examples of alkyls include methyl, ethyl, ethenyl, ethynyl, propyl, 1-ethyl-propyl, propenyl, propynyl, isopropyl, n-butyl, isobutyl, sec-butyl, tert-butyl, 2-methylbutyl, 3-methyl-butyl, 1-but-3-enyl, butynyl, pentyl, 2-pentyl, isopentyl, neopentyl, 3-methylpentyl, 1-pent-3-enyl, 1-pent-4-enyl, pentyn-2-yl, hexyl, 2-hexyl, 3-hexyl, 1-hex-5-enyl, formyl, acetyl, acetylamino, trifluoromethyl, propionic acid ethyl ester, trifluoroacetyl, methylsulfonyl, ethylsulfonyl, 1-hydroxy-1-methylethyl, 2-hydroxy-1,1-dimethyl-ethyl, 1,1-dimethyl-propyl, cyano-dimethyl-methyl, propylamino, and the like.

In an embodiment, alkyls may be selected from sec-butyl, isobutyl, ethynyl, 1-ethyl-propyl, pentyl, 3-methyl-butyl, pent-4-enyl, isopropyl, tert-butyl, 2-methylbutane, and the like.

In another embodiment, alkyls may be selected from formyl, acetyl, acetylamino, trifluoromethyl, propionic acid ethyl ester, trifluoroacetyl, methylsulfonyl, ethylsulfonyl, 1-hydroxy-1-methylethyl, 2-hydroxy-1,1,-dimethyl-ethyl, 1,1-dimethyl-propyl, cyano-dimethyl-methyl, propylamino, and the like.

The term "alkoxy" in the present invention refers to straight or branched chain alkyl groups, wherein an alkyl group is as defined above, and having 1 to 20 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexyloxy, heptyloxy, allyloxy, 2-(2-methoxy-ethoxy)-ethoxy, benzyloxy, 3-methylpentoxy, and the like.

In an embodiment, alkoxy groups may be selected from allyloxy, hexyloxy, heptyloxy, 2-(2-methoxy-ethoxy)-ethoxy, benzyloxy, and the like.

The term "—C(O)-alkyl" or "alkanoyl" refers to an acyl group derived from an alkylcarboxylic acid, a cycloalkylcarboxylic acid, a heterocycloalkylcarboxylic acid, an arylcarboxylic acid, an arylalkylcarboxylic acid, a heteroarylcarboxylic acid, or a heteroarylalkylcarboxylic acid, examples of which include formyl, acetyl, 2,2,2-trifluoroacetyl, propionyl, butyryl, valeryl, 4-methylvaleryl, and the like.

The term "cycloalkyl" refers to an optionally substituted carbocyclic ring system of one or more 3, 4, 5, 6, 7, or 8 membered rings, including 9, 10, 11, 12, 13, and 14 membered fused ring systems, all of which can be saturated or partially unsaturated. The cycloalkyl may be monocyclic, bicyclic, tricyclic, and the like. Bicyclic and tricyclic as used herein are intended to include both fused ring systems, such as adamantyl, octahydroindenyl, decahydro-naphthyl, and the like, substituted ring systems, such as cyclopentylcyclohexyl, and spirocycloalkyls such as spiro[2.5]octane, spiro[4.5]decane, 1,4-dioxa-spiro[4.5]decane, and the like. A cycloalkyl may optionally be a benzo fused ring system, which is optionally substituted as defined herein with respect to the definition of aryl. At least one —CH$_2$— group within any such cycloalkyl ring system may be optionally replaced with —C(O)—, —C(S)—, —C(=N—H)—, —C(=N—OH)—, —C(=N-alkyl)- (optionally substituted as defined herein with respect to the definition of alkyl), or —C(=N—O-alkyl)- (optionally substituted as defined herein with respect to the definition of alkyl).

Further examples of cycloalkyl groups include cyclopropyl, cyclobutyl, cyclopentyl, cyclohexyl, octahydronaphthyl, 2,3-dihydro-1H-indenyl, and the like.

In an embodiment, a cycloalkyl may be selected from cyclopentyl, cyclohexyl, cycloheptyl, adamantenyl, bicyclo[2.2.1]heptyl, and the like.

The cycloalkyl groups herein are unsubstituted or substituted in at least one position with various groups. For example, such cycloalkyl groups may be optionally substituted with alkyl, alkoxy, —C(O)H, carboxy, alkoxycarbonyl, cycloalkyl, heterocycloalkyl, aryl, heteroaryl, amido, alkanoylamino, amidino, alkoxycarbonylamino, N-alkyl amidino, N-alkyl amido, N,N'-dialkylamido, aralkoxycarbonylamino, halogen, alkylthio, alkylsulfinyl, alkylsulfonyl, hydroxy, cyano, nitro, amino, monoalkylamino, dialkylamino, haloalkyl, haloalkoxy, aminoalkyl, monoalkylaminoalkyl, dialkylaminoalkyl, and the like.

The term "cycloalkylcarbonyl" refers to an acyl group of the formula cycloalkyl-C(O)— in which the term "cycloalkyl" has the significance given above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl, and the like.

The term "heterocycloalkyl," "heterocycle," or "heterocyclyl," refers to a monocyclic, bicyclic or tricyclic heterocycle group, containing at least one nitrogen, oxygen or sulfur atom ring member and having 3 to 8 ring members in each ring, wherein at least one ring in the heterocycloalkyl ring system may optionally contain at least one double bond. At least one —CH$_2$— group within any such heterocycloalkyl ring system may be optionally replaced with —C(O)—, —C(S)—, —C(N)—, —C(=N—H)—, —C(=N—OH)—, —C(=N-alkyl)- (optionally substituted as defined herein with respect to the definition of alkyl), or —C(=N—O-alkyl)- (optionally substituted as defined herein with respect to the definition of alkyl).

The terms "bicyclic" and "tricyclic" as used herein are intended to include both fused ring systems, such as 2,3-dihydro-1H-indole, and substituted ring systems, such as bicyclohexyl. At least one —CH$_2$— group within any such heterocycloalkyl ring system may be optionally replaced with —C(O)—, —C(N)— or —C(S)—. Heterocycloalkyl is intended to include sulfones, sulfoxides, N-oxides of tertiary nitrogen ring members, and carbocyclic fused and benzo fused ring systems wherein the benzo fused ring system is optionally substituted as defined herein with respect to the definition of aryl. Such heterocycloalkyl groups may be optionally substituted on one or more carbon atoms by halogen, alkyl, alkoxy, cyano, nitro, amino, alkylamino, dialkylamino, monoalkylaminoalkyl, dialkylaminoalkyl, haloalkyl, haloalkoxy, aminohydroxy, oxo, aryl, aralkyl, heteroaryl, heteroaralkyl, amidino, N-alkylamidino, alkoxycarbonylamino, alkylsulfonylamino, and the like, and/or on a secondary nitrogen atom (i.e., —NH—) by hydroxy, alkyl, aralkoxycarbonyl, alkanoyl, heteroaralkyl, phenyl, phenylalkyl, and the like.

Examples of a heterocycloalkyl include morpholinyl, thiomorpholinyl, thiomorpholinyl S-oxide, thiomorpholinyl S,S-dioxide, piperazinyl, homopiperazinyl, pyrrolidinyl, pyrrolinyl, 2,5-dihydro-pyrrolyl, tetrahydropyranyl, pyranyl, thiopyranyl, piperidinyl, tetrahydrofuranyl, tetrahydrothienyl, imidazolidinyl, homopiperidinyl, 1,2-dihydropyridinyl, homomorpholinyl, homothiomorpholinyl, homothiomorpholinyl S,S-dioxide, oxazolidinonyl, dihydropyrazolyl, dihydropyrrolyl, 1,4-dioxa-spiro[4.5]decyl, dihydropyrazinyl, dihydropyridinyl, dihydropyrimidinyl, dihydrofuryl, dihydropyranyl, tetrahydrothienyl S-oxide, tetrahydrothienyl S,S-dioxide, homothiomorpholinyl S-oxide, 2-oxo-piperidinyl, 5-oxo-pyrrolidinyl, 2-oxo-1,2-dihydro-pyridinyl, 6-oxo-6H-pyranyl, 1,1-dioxo-hexahydro-thiopyranyl, 1-acetyl-piperidinyl, 1-methanesulfonylpiperidinyl, 1-ethanesulfonylpiperidinyl, 1-oxo-hexahydro-thiopyranyl, 1-(2,2,2-trifluoroacetyl)-piperidinyl, 1-formyl-piperidinyl, and the like.

In an embodiment, a heterocycloalkyl may be selected from pyrrolidinyl, 2,5-dihydro-pyrrolyl, piperidinyl, 1,2-dihydro-pyridinyl, pyranyl, piperazinyl, imidazolidinyl, thiopyranyl, tetrahydropyranyl, 1,4-dioxa-spiro[4.5]decyl, and the like.

In another embodiment, a heterocycloalkyl may be selected from 2-oxo-piperidinyl, 5-oxo-pyrrolidinyl, 2-oxo-1,2-dihydro-pyridinyl, 6-oxo-6H-pyranyl, 1,1-dioxo-hexahydro-thiopyranyl, 1-acetyl-piperidinyl, 1-methanesulfonyl piperidinyl, 1-ethanesulfonylpiperidinyl, 1-oxo-hexahydro-thiopyranyl, 1-(2,2,2-trifluoroacetyl)-piperidinyl; 1-formyl-piperidinyl, and the like.

The term "aryl" refers to an aromatic carbocyclic group having a single ring (e.g., phenyl) or multiple condensed rings in which at least one ring is aromatic. The aryl may be monocyclic, bicyclic, tricyclic, etc. Bicyclic and tricyclic as used herein are intended to include both fused ring systems, such as naphthyl and β-carbolinyl, and substituted ring systems, such as biphenyl, phenylpyridyl, diphenylpiperazinyl, tetrahydronaphthyl, and the like. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or substituted in one or more positions with various groups. For example, such aryl groups may be optionally substituted with alkyl, alkoxy, C(O)H, carboxy, alkoxycarbonyl, aryl, heteroaryl, cycloalkyl, heterocycloalkyl, amido, alkanoylamino, amidino, alkoxycarbonylamino, N-alkyl amidino, N-alkyl amido, N,N'-dialkylamido, aralkoxycarbonylamino, halogen, alkyl thio, alkylsulfinyl, alkylsulfonyl, hydroxy, cyano, nitro, amino, monoalkylamino, dialkylamino, aralkoxycarbonylamino, haloalkyl, haloalkoxy, aminoalkyl, monoalkylaminoalkyl, dialkylaminoalkyl, and the like.

Examples of aryl groups are phenyl, p-tolyl, 4-methoxyphenyl, 4-(tert-butoxy)phenyl, 3-methyl-4-methoxyphenyl, 4-CF$_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl, and the like.

Further examples of aryl groups include 3-tert-butyl-1-fluoro-phenyl, 1,3-difluoro-phenyl, (1-hydroxy-1-methyl-ethyl)-phenyl, 1-fluoro-3-(2-hydroxy-1,1-dimethyl-ethyl)-phenyl, (1,1-dimethyl-propyl)-phenyl, cyclobutyl-phenyl, pyrrolidin-2-yl-phenyl, (5-oxo-pyrrolidin-2-yl)-phenyl, (2,5-dihydro-1H-pyrrol-2-yl)-phenyl, (1H-pyrrol-2-yl)-phenyl, (cyano-dimethyl-methyl)-phenyl, tert-butyl-phenyl, 1-fluoro-2-hydroxy-phenyl, 1,3-difluoro-4-propylamino-phenyl, 1,3-difluoro-4-hydroxy-phenyl, 1,3-difluoro-4-ethylamino-phenyl, 3-isopropyl-phenyl, (3H-[1,2,3]triazol-4-yl)-phenyl, [1,2,3]triazol-1-yl-phenyl, [1,2,4]thiadiazol-3-yl-phenyl, [1,2,4]thiadiazol-5-yl-phenyl, (4H-[1,2,4]triazol-3-yl)-phenyl, [1,2,4]oxadiazol-3-yl-phenyl, imidazol-1-yl-phenyl, (3H-imidazol-4-yl)-phenyl, [1,2,4]triazol-4-yl-phenyl, [1,2,4]oxadiazol-5-yl-phenyl, isoxazol-3-yl-phenyl, (1-methyl-cyclopropyl)-phenyl, isoxazol-4-yl-phenyl, isoxazol-5-yl-phenyl, 1-cyano-2-tert-butyl-phenyl, 1-trifluoromethyl-2-tert-butyl-phenyl, 1-chloro-2-tert-butyl-phenyl, 1-acetyl-2-tert-butyl-phenyl, 1-tert-butyl-2-methyl-phenyl, 1-tert-butyl-2-ethyl-phenyl, 1-cyano-3-tert-butyl-phenyl, 1-trifluoromethyl-3-tert-butyl-phenyl, 1-chloro-3-tert-butyl-phenyl, 1-acetyl-3-tert-butyl-phenyl, 1-tert-butyl-3-methyl-phenyl 1-tert-butyl-3-ethyl-phenyl, 4-tert-butyl-1-imidazol-1-yl-phenyl, ethylphenyl, isobutylphenyl, isopropylphenyl, 3-allyloxy-1-fluoro-phenyl, (2,2-dimethyl-propyl)-phenyl, ethynylphenyl, 1-fluoro-3-heptyloxy-phenyl, 1-fluoro-3-[2-(2-methoxy-ethoxy)-ethoxy]-phenyl, 1-benzyloxy-3-fluoro-phenyl, 1-fluoro-3-hydroxy-phenyl, 1-fluoro-3-hexyloxy-phenyl, (4-methyl-thiophen-2-yl)-phenyl, (5-acetyl-thiophen-2-yl)-phenyl, furan-3-yl-phenyl, thiophen-3-yl-phenyl, (5-formyl-thiophen-2-yl)-phenyl, (3-formyl-furan-2-yl)-phenyl, acetylamino-phenyl, trifluoromethylphenyl, sec-butyl-phenyl, pentylphenyl, (3-methyl-butyl)-phenyl, (1-ethyl-propyl)-phenyl, cyclopentyl-phenyl, 3-pent-4-enyl-phenyl, phenyl propionic acid ethyl ester, pyridin-2-yl-phenyl, (3-methyl-pyridin-2-yl)-phenyl, thiazol-2-yl-phenyl, (3-methyl-thiophen-2-yl)-phenyl, fluoro-phenyl, adamantan-2-yl-phenyl, 1,3-difluoro-2-hydroxy-phenyl, cyclopropyl-phenyl, 1-bromo-3-tert-butyl-phenyl, (3-bromo-[1,2,4]thiadiazol-5-yl)-phenyl, (1-methyl-1H-imidazol-2-yl)-phenyl, 3,5-dimethyl-3H-pyrazol-4-yl)-phenyl, (3,6-dimethyl-pyrazin-2-yl)-phenyl, (3-cyano-pyrazin-2-yl)-phenyl, thiazol-4-yl-phenyl, (4-cyano-pyridin-2-yl)-phenyl, pyrazin-2-yl-phenyl, (6-methyl-pyridazin-3-yl)-phenyl, (2-cyano-thiophen-3-yl)-phenyl, (2-chloro-thiophen-3-yl)-phenyl, (5-acetyl-thiophen-3-yl)-phenyl, cyano-phenyl, and the like.

The term "heteroaryl" refers to an aromatic heterocycloalkyl group as defined above. The heteroaryl groups herein are unsubstituted or substituted in at least one position with various groups. For example, such heteroaryl groups may be optionally substituted with, for example, alkyl, alkoxy, halogen, hydroxy, cyano, nitro, amino, monoalkylamino, dialkylamino, haloalkyl, haloalkoxy, C(O)H, carboxy, alkoxycarbonyl, cycloalkyl, heterocycloalkyl, aryl, heteroaryl, amido, alkanoylamino, amidino, alkoxycarbonylamino, N-alkyl amidino, N-alkyl amido, N,N'-dialkylamido, alkyl thio, alkylsulfinyl, alkylsulfonyl, aralkoxycarbonylamino, aminoalkyl, monoalkylaminoalkyl, dialkylaminoalkyl, and the like.

Examples of heteroaryl groups include pyridyl, pyrimidyl, furanyl, imidazolyl, thienyl, oxazolyl, thiazolyl, pyrazinyl, 3-methyl-thienyl, 4-methyl-thienyl, 3-propyl-thienyl, 2-chloro-thienyl, 2-chloro-4-ethyl-thienyl, 2-cyano-thienyl, 5-acetyl-thienyl, 5-formyl-thienyl, 3-formyl-furanyl, 3-methyl-pyridinyl, 3-bromo-[1,2,4]thiadiazolyl, 1-methyl-1H-imidazole, 3,5-dimethyl-3H-pyrazolyl, 3,6-dimethyl-pyrazinyl, 3-cyano-pyrazinyl, 4-tert-butyl-pyridinyl, 4-cyano-pyridinyl, 6-methyl-pyridazinyl, 2-tert-butyl-pyrimidinyl, 4-tert-butyl-pyrimidinyl, 6-tert-butyl-pyrimidinyl, 5-tert-butyl-pyridazinyl, 6-tert-butyl-pyridazinyl, quinolinyl, benzothienyl, indolyl, indolinyl, pyridazinyl, isoindolyl, isoquinolyl, quinazolinyl, quinoxalinyl, phthalazinyl, imidazolyl, isoxazolyl, pyrazolyl, indolizinyl, indazolyl, benzothiazolyl, benzimidazolyl, benzofuranyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, tetrahydrocarbazole, tetrahydrobetacarboline, and the like.

In an embodiment, a heteroaryl group may be selected from pyridyl, pyrimidyl, furanyl, imidazolyl, thienyl, oxazolyl, thiazolyl, pyrazinyl, and the like.

In another embodiment, a heteroaryl group may be selected from 3-methyl-thienyl, 4-methyl-thienyl, 3-propyl-thienyl, 2-chloro-thienyl, 2-chloro-4-ethyl-thienyl, 2-cyano-thienyl, 5-acetyl-thienyl, 5-formyl-thienyl, 3-formyl-furanyl, 3-methyl-pyridinyl, 3-bromo-[1,2,4]thiadiazolyl, 1-methyl-1H-imidazole, 3,5-dimethyl-3H-pyrazolyl, 3,6-dimethyl-pyrazinyl, 3-cyano-pyrazinyl, 4-tert-butyl-pyridinyl, 4-cyano-pyridinyl, 6-methyl-pyridazinyl, 2-tert-butylpyrimidinyl, 4-tert-butyl-pyrimidinyl, 6-tert-butyl-pyrimidinyl, 5-tert-butyl-pyridazinyl, 6-tert-butyl-pyridazinyl, and the like.

Further examples of heterocycloalkyls and heteroaryls may be found in Katritzky, A. R. et al., *Comprehensive Heterocyclic Chemistry: The Structure, Reactions, Synthesis and Use of Heterocyclic Compounds*, Vol. 1-8, New York: Pergamon Press, 1984.

The term "aralkoxycarbonyl" refers to a group of the formula aralkyl-O—C(O)— in which the term "aralkyl" is encompassed by the definitions above for aryl and alkyl. Examples of an aralkoxycarbonyl group include benzyloxycarbonyl 4-methoxyphenylmethoxycarbonyl, and the like.

The term "aryloxy" refers to a group of the formula —O-aryl in which the term aryl is as defined above.

The term "aralkanoyl" refers to an acyl group derived from an aryl-substituted alkanecarboxylic acid such as phenylacetyl, 3-phenylpropionyl(hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like.

The term "aroyl" refers to an acyl group derived from an arylcarboxylic acid, "aryl" having the meaning given above. Examples of such aroyl groups include substituted and unsubstituted benzoyl or naphthoyl such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "haloalkyl" refers to an alkyl group having the meaning as defined above wherein one or more hydrogens are replaced with a halogen. Examples of such haloalkyl groups include chloromethyl, 1-bromoethyl, fluoromethyl, difluoromethyl, trifluoromethyl, 1,1,1-trifluoroethyl, and the like.

The term "epoxide" refers to chemical compounds or reagents comprising a bridging oxygen wherein the bridged atoms are also bonded to one another either directly or indirectly. Examples of epoxides include epoxyalkyl (e.g., ethylene oxide, and 1,2-epoxybutane), and epoxycycloalkyl (e.g., 1,2-epoxycyclohexane, 1,2-epoxy-1-methylcyclohexane), and the like.

The term "structural characteristics" refers to chemical moieties, chemical motifs, and portions of chemical compounds. These include R groups, such as but not limited to those defined herein, ligands, appendages, and the like. For example, structural characteristics may be defined by their properties, such as, but not limited to, their ability to participate in intermolecular interactions including Van der Waal's interactions (e.g., electrostatic interactions, dipole-dipole interactions, dispersion forces, hydrogen bonding, and the like). Such characteristics may impart desired pharmacokinetic properties and thus have an increased ability to cause the desired effect and thus prevent or treat the targeted diseases or conditions.

Compounds of formula (I) also comprise structural moieties that may participate in inhibitory interactions with at least one subsite of beta-secretase. For example, moieties of the compounds of formula (I) may interact with at least one of the S1, S1' and S2' subsites, wherein S1 comprises residues Leu30, Tyr71, Phe108, Ile110, and Trp115, S1' comprises residues Tyr198, Ile226, Val227, Ser 229, and Thr231, and S2' comprises residues Ser35, Asn37, Pro70, Tyr71, Ile118, and Arg128. Such compounds and methods of treatment may have an increased ability to cause the desired effect and thus prevent or treat the targeted diseases or conditions.

The term "pharmaceutically acceptable" refers to those properties and/or substances that are acceptable to the patient from a pharmacological/toxicological point of view, and to the manufacturing pharmaceutical chemist from a physical/chemical point of view regarding composition, formulation, stability, patient acceptance, and bioavailability.

The term "effective amount" as used herein refers to an amount of a therapeutic agent administered to a host, as defined herein, necessary to achieve a desired effect.

The term "therapeutically effective amount" as used herein refers to an amount of a therapeutic agent administered to a host to treat or prevent a condition treatable by administration of a composition of the invention. That amount is the amount sufficient to reduce or lessen at least one symptom of the disease being treated or to reduce or delay onset of one or more clinical markers or symptoms of the disease.

The term "therapeutically active agent" refers to a compound or composition that is administered to a host, either alone or in combination with another therapeutically active agent, to treat or prevent a condition treatable by administration of a composition of the invention.

The terms "pharmaceutically acceptable salt" and "salts thereof" refer to acid addition salts or base addition salts of the compounds in the present invention. A pharmaceutically acceptable salt is any salt which retains the activity of the parent compound and does not impart any deleterious or undesirable effect on the subject to whom it is administered and in the context in which it is administered. Pharmaceutically acceptable salts include salts of both inorganic and organic acids. Pharmaceutically acceptable salts include acid salts such as acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic, toluenesulfonic, and the like. Other acceptable salts may be found, for example, in Stahl et al., *Pharmaceutical Salts: Properties, Selection, and Use*, Wiley-VCH; 1st edition (Jun. 15, 2002).

In an embodiment of the present invention, a pharmaceutically acceptable salt is selected from hydrochloric, hydrobromic, hydroiodic, nitric, sulfuric, phosphoric, citric, methanesulfonic, $CH_3—(CH_2)_{0-4}—COOH$, $HOOC—(CH_2)_{0-4}—COOH$, $HOOC—CH=CH—COOH$, phenyl-COOH, and the like.

The term "unit dosage form" refers to physically discrete units suitable as unitary dosages for human subjects or other mammals, each unit containing a predetermined quantity of active material calculated to produce the desired therapeutic effect, in association with a suitable pharmaceutical vehicle. The concentration of active compound in the drug composition will depend on absorption, inactivation, and/or excretion rates of the active compound, the dosage schedule, the amount administered and medium and method of administration, as well as other factors known to those of skill in the art.

The term "modulate" refers to a chemical compound's activity of either enhancing or inhibiting a functional property of biological activity or process.

The terms "interact" and "interactions" refer to a chemical compound's association and/or reaction with another chemical compound, such as an interaction between an inhibitor and beta-secretase. Interactions include, but are not limited to, hydrophobic, hydrophilic, lipophilic, lipophobic, electrostatic, and van der Waal's interactions including hydrogen bonding.

An "article of manufacture" as used herein refers to materials useful for the diagnosis, prevention or treatment of the disorders described above, such as a container with a label. The label can be associated with the article of manufacture in a variety of ways including, for example, the label may be on the container or the label may be in the container as a package insert. Suitable containers include, for example, blister packs, bottles, bags, vials, syringes, test tubes, and the like. The containers may be formed from a variety of materials such as glass, metal, plastic, rubber, paper, and the like. The container holds a composition as described herein which is effective for diagnosing, preventing, or treating a condition treatable by a compound or composition of the present invention.

The article of manufacture may contain bulk quantities or less of a composition as described herein. The label on, or associated with, the container may provide instructions for the use of the composition in diagnosing, preventing, or treating the condition of choice, instructions for the dosage amount and for the methods of administration. The label may further indicate that the composition is to be used in combination with one or more therapeutically active agents wherein the therapeutically active agent is selected from an antioxidant, an anti-inflammatory, a gamma-secretase inhibitor, a neurotrophic agent, an acetyl cholinesterase inhibitor, a statin, an A-beta, an anti-A-beta antibody, and/or a beta-secretase complex or fragment thereof. The article of manufacture may further comprise multiple containers, also referred to herein as a kit, comprising a therapeutically active agent or a pharmaceutically-acceptable buffer, such as phosphate-buffered saline, Ringer's solution and/or dextrose solution. It may further include other materials desirable from a commercial and user standpoint, including other buffers, diluents, filters, needles, syringes, and/or package inserts with instructions for use.

The compounds of formula (I), their compositions, and methods of treatment employing them, can be enclosed in multiple or single dose containers. The enclosed compounds and/or compositions can be provided in kits, optionally including component parts that can be assembled for use. For example, a compound inhibitor in lyophilized form and a suitable diluent may be provided as separated components for combination prior to use. A kit may include a compound inhibitor and at least one additional therapeutic agent for co-administration. The inhibitor and additional therapeutic agents may be provided as separate component parts.

A kit may include a plurality of containers, each container holding at least one unit dose of the compound of the present invention. The containers are preferably adapted for the desired mode of administration, including, for example, pill, tablet, capsule, powder, gel or gel capsule, sustained-release capsule, or elixir form, and/or combinations thereof, and the like for oral administration, depot products, pre-filled syringes, ampoules, vials, and the like for parenteral administration, and patches, medipads, creams, and the like for topical administration.

The term "$C_{max}$" refers to the peak plasma concentration of a compound in a host.

The term "$T_{max}$" refers to the time at peak plasma concentration of a compound in a host.

The term "half-life" refers to the period of time required for the concentration or amount of a compound in a host to be reduced to exactly one-half of a given concentration or amount.

DETAILED DESCRIPTION OF THE PRESENT INVENTION

The present invention is directed to novel compounds and also to methods of treating at least one condition, disorder, or disease associated with amyloidosis using such compounds. Amyloidosis refers to a collection of diseases, disorders, or conditions associated with abnormal deposition of amyloidal protein.

An embodiment of the present invention is to provide methods of preventing or treating at least one condition associated with amyloidosis using compounds of formula (I) with a high degree of efficacy. Compounds and methods of treatment that are efficacious are those that have an increased ability to cause the desired effect and thus prevent or treat the targeted diseases or conditions.

Another embodiment of the present invention is to provide compounds of formula (I),

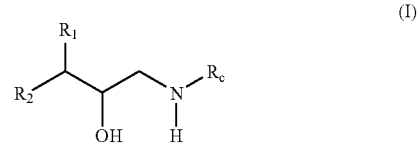

or pharmaceutically acceptable salts thereof, for preventing or treating at least one condition that benefits from inhibition of at least one aspartyl-protease, and wherein $R_1$, $R_2$, and $R_C$ are defined below.

Another embodiment of the present invention is to provide methods for preventing or treating at least one condition that benefits from inhibition of at least one aspartyl-protease, comprising compounds of formula (I), or pharmaceutically acceptable salts thereof, wherein the inhibition is at least 10% for a dose of 100 mg/kg or less, and wherein $R_1$, $R_2$, and $R_C$ are defined below.

Another embodiment of the present invention is to provide a method of preventing or treating at least one condition that benefits from inhibition of at least one aspartyl-protease, comprising administering to a host a composition comprising a therapeutically effective amount of at least one compound of formula (I), or pharmaceutically acceptable salts thereof, wherein $R_1$ is

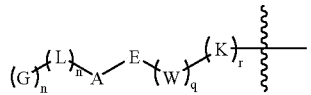

wherein n is 0 or 1; q is 0 or 1; r is 0, 1, or 2;

K is selected from —(CR$_{3a}$R$_{3b}$)—, —O—, —SO$_2$—, —C(O)—, and —CH(NR$_{55}$R$_{60}$)—;

R$_{55}$ and R$_{60}$ are each independently selected from hydrogen and alkyl;

R$_{3a}$ and R$_{3b}$ are independently selected from hydrogen, halogen, —O-alkyl, and alkyl optionally substituted with at least one group independently selected from halogen, —CN, —CF$_3$, and —OH;

W is selected from —(CH$_2$)$_{1-4}$—, —O—, —S(O)$_{0-2}$—, —N(R$_{55}$)—, and —C(O)—;

E is a bond or alkyl;

A is selected from aryl optionally substituted with at least one group independently selected from R$_{50}$, cycloalkyl optionally substituted with at least one group independently selected from R$_{50}$, heteroaryl optionally substituted with at least one group independently selected from R$_{50}$, and heterocycle optionally substituted with at least one group independently selected from R$_{50}$,
  wherein at least one atom of the heterocycle is optionally replaced with —C(O)— and —S(O)$_{0-2}$—,
  wherein at least one heteroatom of the heteroaryl or heterocycle is optionally substituted with a group independently selected from —(CO)$_{0-1}$R$_{215}$, —(CO)$_{0-1}$R$_{220}$, —S(O)$_{0-2}$R$_{200}$, and —N(R$_{200}$)—S(O)$_{0-2}$R$_{200}$;

R$_{50}$ is independently selected from —OH, halogen, —OCF$_3$, —NO$_2$, —CN, —N(R)C(O)R, —CO$_2$—R, —NH—CO$_2$—R, —O-(alkyl)-CO$_2$H, —NRR', —SR, —CH$_2$OH, —C(O)—R$_{25}$, —C(O)NRR', —SO$_2$NRR', —S(O)$_{1-2}$R$_{25}$, alkyl (optionally substituted with at least one group independently selected from —CF$_3$, halogen, —O-alkyl, —OCF$_3$, —NRR', —OH, and —CN), cycloalkyl (optionally substituted with at least one group independently selected from —CF$_3$, halogen, —O-alkyl, —OCF$_3$, —NRR', —OH, and —CN), —O-alkyl (optionally substituted with at least one group independently selected from —CF$_3$, halogen, —O-alkyl, —OCF$_3$, —NRR', —OH, and —CN), —O-benzyl (optionally substituted with at least one group independently selected from —H, —OH, halogen, and alkyl), —O—(CH$_2$)$_{0-2}$—O—(CH$_2$)$_{1-2}$—O-alkyl, and —(CH$_2$)$_{0-2}$—O—(CH$_2$)$_{1-2}$—OH;

R and R' are each independently selected from hydrogen, alkyl, —(CH$_2$)$_{0-2}$-aryl and —(CH$_2$)$_{0-2}$-cycloalkyl, wherein each aryl or cycloalkyl is optionally substituted with at least one group independently selected from halogen, hydroxy, alkyl, —O-alkyl, amino, monoalkylamino, and dialkylamino;

R$_{25}$ is selected from alkyl, —(CH$_2$)$_{0-2}$-aryl and —(CH$_2$)$_{0-2}$-cycloalkyl, wherein each aryl or cycloalkyl is optionally substituted with at least one group independently selected from halogen, hydroxy, alkyl, —O-alkyl, amino, monoalkylamino, and dialkylamino;

L is selected from a bond, —C(O)—, —S(O)$_{1-2}$—, —O—, —C(R$_{110}$)(R$_{112}$)O—, —OC(R$_{110}$)(R$_{112}$)—, —N(R$_{110}$)—, —C(O)N(R$_{110}$)—, —N(R$_{110}$)C(O)—, —C(R$_{110}$)(R')—, —C(OH)R$_{110}$—, —SO$_2$NR$_{110}$—, —N(R$_{110}$)SO$_2$—, —N(R$_{110}$)C(O)N(R$_{112}$)—, —N(R$_{110}$)C(S)N(R$_{112}$)—, —OCO$_2$—, —NCO$_2$—, and —OC(O)N(R$_{110}$)—;

R$_{110}$ and R$_{112}$ are each independently selected from hydrogen and alkyl optionally substituted with at least one group independently selected from —OH, —O-alkyl, and halogen;

G is selected from
  -alkyl optionally substituted with at least one group independently selected from —CO$_2$H, —CO$_2$(alkyl), —O-alkyl, —OH, —NRR', alkyl, haloalkyl, -alkyl-O-alkyl, aryl (optionally substituted with at least one group independently selected from R$_{50}$), and heteroaryl (optionally substituted with at least one group independently selected from R$_{50}$);
  —(CH$_2$)$_{0-3}$-cycloalkyl wherein cycloalkyl is optionally substituted with at least one group independently selected from —CO$_2$H, —CO$_2$—(alkyl), —O-alkyl, —OH, —NH$_2$, haloalkyl, alkyl, -alkyl-O-alkyl, mono(alkyl)amino, di(alkyl)amino, aryl (optionally substituted with at least one group independently selected from R$_{50}$), and heteroaryl (optionally substituted with at least one group independently selected from R$_{50}$);
  —(CRR)$_{0-4}$-aryl wherein the aryl is optionally substituted with at least one group independently selected from R$_{50}$;
  —(CH$_{20-4}$-heteroaryl wherein the heteroaryl is optionally substituted with at least one group independently selected from R$_{50}$;
  —(CH$_2$)$_{0-4}$-heterocycle, wherein the heterocycle is optionally substituted with at least one group independently selected from R$_{50}$; and
  —C(R$_{10}$)(R$_{12}$)—C(O)—NH—R$_{14}$;

R$_{10}$ and R$_{12}$ are each independently selected from —H, alkyl, -(alkyl)$_{0-1}$-aryl, -(alkyl)$_{0-1}$-heteroaryl, -(alkyl)$_{0-1}$-heterocycle, aryl, heteroaryl, heterocycle, —(CH$_2$)$_{1-4}$—OH, —(CH$_2$)$_{1-4}$-Z-(CH$_2$)$_{1-4}$-aryl, and —(CH$_2$)$_{1-4}$-Z-(CH$_2$)$_{1-4}$-heteroaryl; wherein the heterocycle, aryl, and heteroaryl groups included within R$_{10}$ and R$_{12}$ are optionally substituted with at least one group independently selected from R$_{50}$;

Z is selected from —O—, —S—, and —NR$_{16}$—;

R$_{14}$ is selected from —H, alkyl, aryl, heteroaryl, heterocycle, -(alkyl)-aryl, -(alkyl)-heteroaryl, alkyl, and —(CH$_2$)$_{0-2}$—O—(CH$_2$)$_{0-2}$—OH; wherein the heterocycle, aryl, and heteroaryl groups included within R$_{14}$ are optionally substituted with at least one group independently selected from R$_{50}$, R$_{16}$ is selected from hydrogen and alkyl; or R$_1$ is selected from

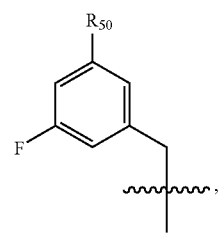
(IIa)

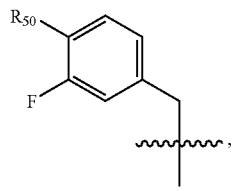
(IIb)

-continued

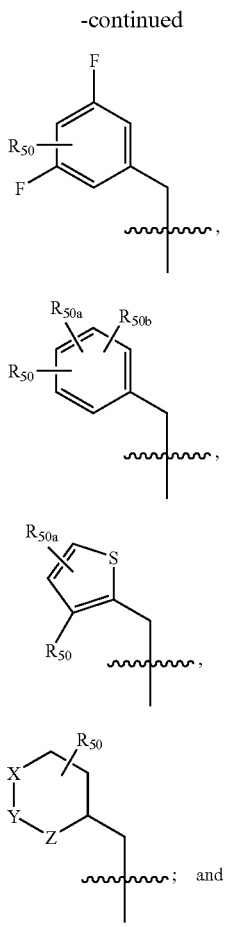

(IIc), (IId), (IIe), (IIf)

alkyl;
wherein
X, Y, and Z are independently selected from —C(H)$_{0-2}$—, —O—, —C(O)—, —NH—, and —N—;
wherein at least one bond of the (IIf) ring may optionally be a double bond;
R$_{50}$, R$_{50a}$, and R$_{50b}$ are independently selected from —H, halogen, —OH, —SH, —CN, —C(O)-alkyl, —NR$_7$R$_8$, —NO$_2$, —S(O)$_{0-2}$-alkyl, alkyl, alkoxy, —O-benzyl (optionally substituted with at least one group independently selected from —H, —OH, and alkyl), —C(O)—NR$_7$R$_8$, alkyloxy, alkoxyalkoxyalkoxy, and cycloalkyl;
wherein the alkyl, alkoxy, and cycloalkyl groups within R$_{50}$, R$_{50a}$, and R$_{50b}$ are optionally substituted with at least one group independently selected from alkyl, halogen, OH, NR$_5$R$_6$, CN, haloalkoxy, NR$_7$R$_8$, and alkoxy;
R$_5$ and R$_6$ are independently selected from —H and alkyl, or
R$_5$ and R$_6$, and the nitrogen to which they are attached, form a 5 or 6 membered heterocycloalkyl ring; and
R$_7$ and R$_8$ are independently selected from —H, alkyl optionally substituted with at least one group independently selected from —OH, —NH$_2$, and halogen, -cycloalkyl, and -alkyl-O-alkyl;
R$_2$ is selected from H, —OH, —O-alkyl (optionally substituted with at least one group independently selected from R$_{200}$), —O-aryl (optionally substituted with at least one group independently selected from R$_{200}$), alkyl (optionally substituted with at least one group independently selected from R$_{200}$), —NH-alkyl (optionally substituted with at least one group independently selected from R$_{200}$), heterocycloalkyl, (wherein at least one carbon is optionally replaced with a group independently selected from —(CR$_{245}$R$_{250}$)—, —O—, —C(O)—, —C(O)C(O)—, —N(R$_{200}$)$_{0-2}$—, and —S(O)$_{0-2}$—, and wherein the heterocycloalkyl is optionally substituted with at least one group independently selected from R$_{200}$), —NH-heterocycloalkyl, (wherein at least one carbon is optionally replaced with a group independently selected from —(CR$_{245}$R$_{250}$)—, —O—, —C(O)—, —C(O)C(O)—, —N(R$_{200}$)$_{0-1}$—, and —S(O)$_{0-2}$—, and wherein the heterocycloalkyl is optionally substituted with at least one group independently selected from R$_{200}$), —C(O)—N(R$_{315}$)(R$_{320}$), (wherein R$_{315}$ and R$_{320}$ are each independently selected from H, alkyl, and aryl), —O—C(O)—N(R$_{315}$)(R$_{320}$), —NH—R$_{400}$, R$_{400}$, —NH—R$_{500}$, R$_{500}$, —NH—R$_{600}$, R$_{600}$, and —NH—R$_{700}$;

R$_{400}$ is

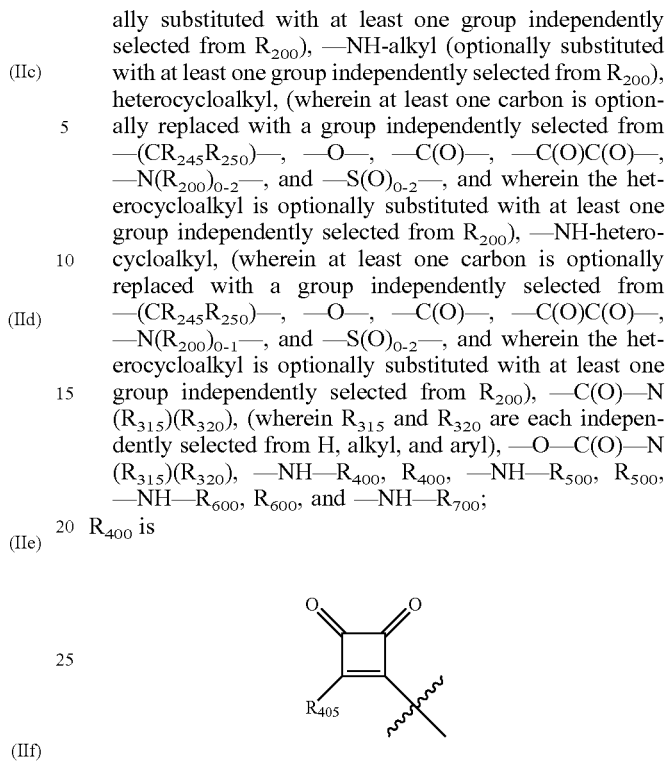

wherein R$_{405}$ is selected from H, —N(R$_{515}$)$_2$ and O-alkyl;
R$_{500}$ is a heteroaryl selected from III(a) and III(b)

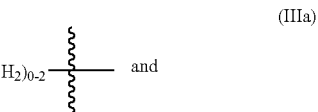 (IIIa)

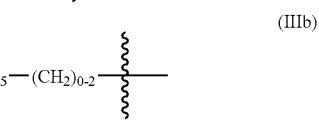 (IIIb)

wherein
M$_1$ and M$_4$ are independently selected from —C(R$_{505}$)—, —N—, —N(R$_{515}$)—, —S—, and —O—;
M$_2$ and M$_3$ are independently selected from —C(R$_{510}$)—, —N(R$_{520}$)$_{0-1}$—, —S—, and —O—;
M$_5$ is selected from —C— and —N—;
R$_{505}$ is independently selected from H, alkyl, halogen, —NO$_2$, —CN, —R$_{200}$, and aryl;
R$_{510}$ is independently selected from H, alkyl, halogen, amino, —CF$_3$, —R$_{200}$, and aryl;
R$_{515}$ is independently selected from H, alkyl, and aryl;
R$_{520}$ is independently selected from H, alkyl, —(CH$_2$)$_{0-2}$-aryl, and —C(Ph)$_3$;
R$_{600}$ is a monocyclic, bicyclic, or tricyclic heteroaryl ring system of 6, 7, 8, 9, 10, 11, 12, 13, or 14 atoms, optionally substituted with at least one group independently selected from R$_{605}$;
R$_{605}$ is selected from hydrogen, halogen, alkyl, aryl, —CO$_2$-alkyl, nitro, —CN, amino, —NR$_{220}$R$_{225}$, -thioalkyl, —CF$_3$, —OH, —O-alkyl, and heterocycloalkyl;
R$_{700}$ is aryl optionally substituted with at least one R$_{205}$;
R$_C$ is selected from formula (IIIa), (IIIb), (IIIc), (IIId), (IIIe), and (IIIf)

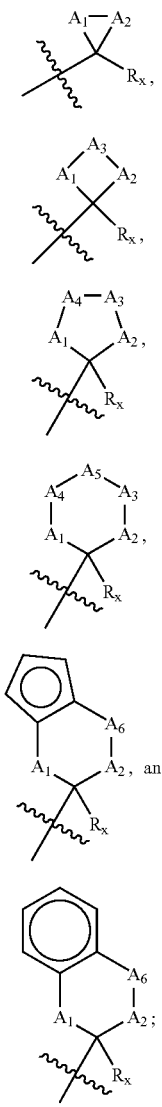

(IIIa)

(IIIb)

(IIIc)

(IIId)

(IIIe)

(IIIf)

wherein, $A_1$ and $A_2$ are independently selected from —$(CH_2)_{1-2}$—, —$CH(R_{200})$—, —$C(R_{200})_2$—, —NH—, —$NR_{220}$—, —$C(=N-R_{230})$—, —$C(=CH-R_{230})$—, —$C(=N-C(O)-R_{230})$—, and —$C(=CH-C(O)-R_{230})$—;

$A_3$, $A_4$, $A_5$, and $A_6$ are independently selected from —$CH_2$—, —$CH(R_{200})$—, —$C(R_{200})_2$—, —O—, —C(O)—, —$S(O)_{0-2}$—, —NH—, —$NR_{220}$—, —$N(CO)_{0-1}R_{200}$—, —$N(S(O_2)alkyl)$-, —$C(=N-R_{230})$—, —$C(=N-NH(alkyl))$-, —$C(=N-N(alkyl)(alkyl))$-, —$C(=N-O-(CH_2)_{1-4}-OH)$—, —$C(=CH-R_{230})$—, —$C(=N-C(O)-R_{230})$—, and —$C(=CH-C(O)-R_{230})$—;

$R_{230}$ is independently selected from —H, —OH, $R_{215}$ (optionally substituted with —OH, —$NH_2$, —C(O)H, and —CN), alkyl, cycloalkyl, alkoxy, -alkyl-OH, -alkyl-$NH_2$, -alkyl-C(O)H, —O—$R_{215}$ (optionally substituted with —OH, —$NH_2$, —C(O)H, and —CN), —O-alkyl, —O-alkyl-OH, —O-alkyl-$NH_2$, —O-alkyl-C(O)H, —$NH_2$, —$NHR_{215}$, —$N(R_{215})_2$, —$NR_{235}R_{240}$, and —CN;

wherein at least one carbon of the alkyl or cycloalkyl within $R_{230}$ is optionally independently replaced with —C(O)— or a heteroatom;

wherein the cycloalkyl and heterocylcoalkyl within formulae (IIIa), (IIIb), (IIIc), (IIId), (IIIe), and (IIIf) may optionally contain at least one double bond;

wherein in formulae (IIIa), (IIIb), (IIIc), and (IIId), at least one of $A_1$, $A_2$, $A_3$, $A_4$, or $A_5$ is selected from —$C(=N-R_{230})$—, —$C(=N-NH(alkyl))$-, —$C(=N-N(alkyl)(alkyl))$-, $C(=N-O-(CH_2)_{1-4}-OH)$—, —$C(=CH-R_{230})$—, —$C(=N-C(O)-R_{230})$—, and —$C(=CH-C(O)-R_{230})$—;

wherein in formulae (IIIe) and (IIIf), when $A_1$, $A_2$, and $A_6$ are selected from —$(CH_2)_{0-2}$—, —$CH(R_{200})$—, —$C(R_{200})_2$—, —O—, —C(O)—, —$S(O)_{0-2}$—, —NH—, —$NR_{220}$—, —$N(CO)_{0-1}R_{200}$—, and —$N(S(O_2)alkyl)$-, at least one carbon of the aryl ring group within (IIIe) and (IIIf) is optionally independently replaced with a group selected from —N—, —NH—, —O—, —C(O)—, and —$S(O)_{0-2}$—;

wherein each aryl or heteroaryl group attached directly or indirectly to $R_C$ is optionally substituted with at least one group independently selected from $R_{200}$;

wherein each cycloalkyl or heterocycloalkyl attached directly or indirectly to $R_C$ is optionally substituted with at least one group independently selected from $R_{210}$; and $R_x$ is selected from
-aryl, heteroaryl, cycloalkyl, heterocycloalkyl, and —$R_{xa}$—$R_{xb}$, wherein $R_{xa}$ and $R_{xb}$ are independently selected from -aryl, -heteroaryl, -cycloalkyl, and -heterocycloalkyl;

wherein each aryl or heteroaryl group within $R_X$ is optionally substituted with at least one group independently selected from $R_{200}$;

wherein each cycloalkyl or heterocycloalkyl within $R_X$ is optionally substituted with at least one group independently selected from $R_{210}$; and wherein at least one carbon of the heteroaryl or heterocycloalkyl group within $R_X$ is independently optionally replaced with a group independently selected from —NH—, —N—, —$N(CO)_{0-1}R_{215}$—, —$N(CO)_{0-1}R_{220}$—, —O—, —C(O)—, —$S(O)_{0-2}$—, and —$NS(O)_{0-2}R_{200}$;

$R_{200}$ at each occurrence is independently selected from
-alkyl optionally substituted with at least one group independently selected from $R_{205}$, —OH, —$NO_2$, -halogen, —CN, —$(CH_2)_{0-4}$—C(O)H, —$(CO)_{0-1}R_{215}$, —$(CO)_{0-1}R_{220}$, —$(CH_2)_{0-4}$—$(CO)_{0-1}$—$NR_{220}R_{225}$, —$(CH_2)_{0-4}$—$(CO)_{0-1}$—$NH(R_{215})$, —$(CH_2)_{0-4}$—C(O)-alkyl, —$(CH_2)_{0-4}$—$(CO)_{0-1}$-cycloalkyl, —$(CH_2)_{0-4}$—$(CO)_{0-1}$-heterocycloalkyl, —$(CH_2)_{0-4}$—$(CO)_{0-1}$-aryl, —$(CH_2)_{0-4}$—$(CO)_{0-1}$-heteroaryl, —$(CH_2)_{0-4}$—C(O)—O—$R_{215}$, —$(CH_2)_{0-4}$—$SO_2$—$NR_{220}R_{225}$, —$(CH_2)_{0-4}$—$S(O)_{0-2}$-alkyl, —$(CH_2)_{0-4}$—$S(O)_{0-2}$-cycloalkyl, —$(CH_2)_{0-4}$—N(H or $R_{215}$)—C(O)—O—$R_{215}$, —$(CH_2)_{0-4}$—N(H or $R_{215}$)—$SO_2$—$R_{220}$, —$(CH_2)_{0-4}$—N(H or $R_{215}$)—C(O)—$N(R_{215})_2$, —$(CH_2)_{0-4}$—N(H or $R_{215}$)—C(O)—$R_{220}$, —$(CH_2)_{0-4}$—O—C(O)-alkyl, —$(CH_2)_{0-4}$—O—

($R_{215}$), —($CH_2$)$_{0-4}$—S—($R_{215}$), —($CH_2$)$_{0-4}$—O-alkyl optionally substituted with at least one halogen, and -adamantane;

wherein each aryl and heteroaryl group included within $R_{200}$ is optionally substituted with at least one group independently selected from $R_{205}$, $R_{210}$, and alkyl (optionally substituted with at least one group independently selected from $R_{205}$ and $R_{210}$);

wherein each cycloalkyl or heterocycloalkyl group included within $R_{200}$ is optionally substituted with at least one group independently selected from $R_{210}$;

$R_{205}$ at each occurrence is independently selected from -alkyl, -haloalkoxy, —($CH_2$)$_{0-3}$-cycloalkyl, -halogen, —($CH_2$)$_{0-6}$—OH, —O-aryl, —OH, —SH, —($CH_2$)$_{0-6}$—C(O)H, —($CH_2$)$_{0-6}$—CN, —($CH_2$)$_{0-6}$—C(O)—$NR_{235}R_{240}$, —($CH_2$)$_{0-6}$—C(O)—$R_{235}$, —($CH_2$)$_{0-4}$—N(H or $R_{215}$)—$SO_2$—$R_{235}$, —$OCF_3$, —$CF_3$, -alkoxy, -alkoxycarbonyl, and —$NR_{235}R_{240}$;

$R_{210}$ at each occurrence is independently selected from —($CH_2$)$_{0-4}$—OH, —($CH_2$)$_{0-4}$—CN, —($CH_2$)$_{0-4}$—C(O)H, -alkyl optionally substituted with at least one group independently selected from $R_{205}$, -alkanoyl, —S-alkyl; —S(O)$_2$-alkyl, -halogen, -alkoxy, -haloalkoxy, —$NR_{220}R_{225}$, -cycloalkyl optionally substituted with at least one group independently selected from $R_{205}$, -heterocycloalkyl, -heteroaryl, —($CH_2$)$_{0-4}$—$NR_{235}R_{240}$, —($CH_2$)$_{0-4}$—$NR_{235}$(alkoxy), —($CH_2$)$_{0-4}$—S—($R_{215}$), —($CH_2$)$_{0-4}$—$NR_{235}$—C(O)H, —($CH_2$)$_{0-4}$—$NR_{235}$—C(O)-(alkoxy), —($CH_2$)$_{0-4}$—$NR_{235}$—C(O)—$R_{240}$, —C(O)—$NHR_{215}$, —C(O)-alkyl, —C(O)—$NR_{235}R_{240}$, and —S(O)$_2$—$NR_{235}R_{240}$;

$R_{215}$ at each occurrence is independently selected from -alkyl, —($CH_2$)$_{0-2}$-aryl, —($CH_2$)$_{0-2}$-cycloalkyl, —($CH_2$)$_{0-2}$-heteroaryl, —($CH_2$)$_{0-2}$-heterocycloalkyl, and —$CO_2$—$CH_2$-aryl; wherein the aryl group included within $R_{215}$ is optionally substituted with at least one group independently selected from $R_{205}$ and $R_{210}$, and wherein the heterocycloalkyl and heteroaryl groups included within $R_{215}$ are optionally substituted with at least one group independently selected from $R_{210}$;

$R_{220}$ and $R_{225}$ at each occurrence are independently selected from —H, alkyl, —($CH_2$)$_{0-4}$—C(O)H, alkylhydroxyl, alkoxycarbonyl, alkylamino, —S(O)$_2$-alkyl, alkanoyl (optionally substituted with at least one halogen), —C(O)—$NH_2$, —C(O)—NH(alkyl), —C(O)—N(alkyl)(alkyl), haloalkyl, —($CH_2$)$_{0-2}$-cycloalkyl, -(alkyl)-O-(alkyl), aryl, heteroaryl, and heterocycloalkyl;

wherein the aryl, heteroaryl, cycloalkyl and heterocycloalkyl groups included within $R_{220}$ and $R_{225}$ are each optionally substituted with at least one group independently selected from $R_{270}$;

$R_{270}$ at each occurrence is independently selected from —$R_{205}$, alkyl (optionally substituted with at least one group independently selected from $R_{205}$), aryl, halogen, alkoxy, haloalkoxy, —$NR_{235}R_{240}$, —OH, —CN, cycloalkyl (optionally substituted with at least one group independently selected from $R_{205}$), —C(O)-alkyl, —S(O)$_2$—$NR_{235}R_{240}$, —C(O)—$NR_{235}R_{240}$, —S(O)$_2$-alkyl, and —($CH_2$)$_{0-4}$—C(O)H;

$R_{235}$ and $R_{240}$ at each occurrence are independently selected from —H, —OH, —$CF_3$, —$OCF_3$, —$OCH_3$, —$NHCH_3$, —N($CH_3$)$_2$, —($CH_2$)$_{0-4}$—C(O)(H or alkyl), alkyl, alkanoyl, —$SO_2$-alkyl, and aryl.

Exemplary $R_{600}$ substituents of monocyclic, bicyclic, or tricyclic heteroaryls include Benzo[4,5]thieno[3,2-d]pyrimidin-4-yl, 4,6-Diamino-[1,3,5]triazin-2-yl, 3-nitro-pyridin-2-yl, 5-trifluoromethyl-pyridin-2-yl, 8-trifluoromethyl-quinolin-4-yl, 4-trifluoromethyl-pyrimidin-2-yl, 2-phenyl-quinazolin-4-yl, 6-Chloro-pyrazin-2-yl, pyrimidin-2-yl, quinolin-2-yl, 3-Chloro-pyrazin-2-yl, 6-Chloro-2,5-diphenyl-pyrimidin-4-yl, 3-Chloro-quinoxalin-2-yl, 5-ethyl-pyrimidin-2-yl, 6-Chloro-2-methylsulfanyl-5-phenyl-pyrimidin-4-yl, quinolin-4-yl, 3-ethoxycarbonyl-pyridin-2yl, 5-Cyano-pyridin-2-yl, 2-phenyl-quinolin-4-yl, 7H-purin-6-yl, 3-Cyano-pyridin-2-yl, 4,6-dimethoxy-[1,3,5]triazin-2-yl, 3-Cyano-pyrazin-2-yl, 9-(tetrahydro-pyran-2-yl)-9H-purin-6-yl, 2-Chloro-7H-purin-6-yl, 2-Amino-6-chloro-pyrimidin-4-yl, 2-Chloro-6-methyl-pyrimidin-4-yl, 2-Amino-6-methyl-pyrimidin-4-yl, 4-Chloro-pyrimidin-2-yl, 2-Amino-7H-purin-6-yl, 4-trifluoromethyl-pyrimidin-2-yl, and the like.

Exemplary $R_2$ substituents include 3-Allyl-5-benzyl-2-oxo-imidazolidin-1-yl, 6-Benzyl-3,3-dimethyl-2-oxo-piperazin-1-yl, 3-Allyl-5-benzyl-2-oxo-pyrrolidin-1-yl, 5-Benzyl-3-isobutyl-2-oxo-imidazolidin-1-yl, 3-Benzyl-5-methyl-1,1-dioxo-1$\lambda^6$-[1,2,5]thiadiazolidin-2-yl, 3-Benzyl-1,1-dioxo-1$\lambda^6$-isothiazolidin-2-yl, 2-Benzyl-5-oxo-pyrrolidin-1-yl, 5-Benzyl-3-ethyl-2-oxo-pyrrolidin-1-yl, 3-Amino-5-benzyl-2-oxo-pyrrolidin-1-yl, 3-Acetylamino-5-benzyl-2-oxo-pyrrolidin-1-yl, 5-Benzyl-3-[1,3]dioxolan-4-ylmethyl-2-oxo-pyrrolidin-1-yl, 3-Benzyl-5-oxo-morpholin-4-yl, 2-Benzyl-6-oxo-piperazin-1-yl, 8-Benzyl-6-methyl-10-oxo-6,9-diaza-spiro[4.5]dec-9-yl, 5-Benzyl-3-furan-2-ylmethylene-2-oxo-pyrrolidin-1-yl, 3-acetylamino-3-(sec-butyl)-2-oxo-pyrrolidin-1-yl, 3-acetylamino-3-(cyclopropylmethyl)-2-oxo-pyrrolidin-1-yl, 3-(2-amino-5-carboxypentanoylamino)-3-(sec-butyl)-2-oxo-pyrrolidin-1-yl, 3-(2-methoxy-acetylamino)-3-(sec-butyl)-2-oxo-pyrrolidin-1-yl, 3-ethoxycarbonylamino-3-(sec-butyl)-2-oxo-pyrrolidin-1-yl, 3-ethylureido-3-(sec-butyl)-2-oxo-pyrrolidin-1-yl, and 3-hydroxypropionylamino-3-(sec-butyl)-2-oxo-pyrrolidin-1-yl.

In an embodiment, $R_1$ is selected from 3-allyloxy-5-fluoro-benzyl, 3-benzyloxy-5-fluoro-benzyl, 3-propyl-thiophen-2-yl-methyl, 3,5-difluoro-2-propylamino-benzyl, 2-ethylamino-3,5-difluoro-benzyl, 2-hydroxy-5-methyl-benzamide, 3-fluoro-5-[2-(2-methoxy-ethoxy)-ethoxy]-benzyl, 3-fluoro-5-heptyloxy-benzyl, and 3-fluoro-5-hexyloxy-benzyl.

In another embodiment, $R_1$ is selected from a —$CH_2$-aryl, wherein the aryl ring is optionally substituted with at least one group independently selected from halogen, —$C_1$-$C_2$ alkyl, —C1-$C_2$ alkoxy, and —OH.

In another embodiment, $R_1$ is selected from 3-Allyloxy-5-fluoro-benzyl, 3-Benzyloxy-5-fluoro-benzyl, 4-hydroxy-benzyl, 3-hydroxy-benzyl, 3-propyl-thiophen-2-yl-methyl, 3,5-difluoro-2-propylamino-benzyl, 5-chloro-thiophen-2-yl-methyl, 5-chloro-3-ethyl-thiophen-2-yl-methyl, 3,5-difluoro-2-hydroxy-benzyl, 2-ethylamino-3,5-difluoro-benzyl, piperidin-4-yl-methyl, 2-oxo-piperidin-4-yl-methyl, 2-oxo-1,2-dihydro-pyridin-4-yl-methyl, 5-hydroxy-6-oxo-6H-pyran-2-yl-methyl, 2-Hydroxy-5-methyl-benzamide, 3,5-Difluoro-4-hydroxy-benzyl, 3,5-Difluoro-benzyl, 3-Fluoro-4-hydroxy-benzyl, 3-Fluoro-5-[2-(2-methoxy-ethoxy)-ethoxy]-benzyl, 3-Fluoro-5-heptyloxy-benzyl, 3-Fluoro-5-hexyloxy-benzyl, 3-Fluoro-5-hydroxy-benzyl, 3-Fluoro-benzyl, and the like.

Exemplary R₂ substituents include 3-Allyl-5-benzyl-2-oxo-imidazolidin-1-yl, 6-Benzyl-3,3-dimethyl-2-oxo-piperazin-1-yl, 3-Allyl-5-benzyl-2-oxo-pyrrolidin-1-yl, 5-Benzyl-3-isobutyl-2-oxo-imidazolidin-1-yl, 3-Benzyl-5-methyl-1,1-dioxo-1λ⁶-[1,2,5]thiadiazolidin-2-yl, 3-Benzyl-1,1-dioxo-1λ⁶-isothiazolidin-2-yl, 2-Benzyl-5-oxo-pyrrolidin-1-yl, 5-Benzyl-3-ethyl-2-oxo-pyrrolidin-1-yl, 3-Amino-5-benzyl-2-oxo-pyrrolidin-1-yl, 3-Acetylamino-5-benzyl-2-oxo-pyrrolidin-1-yl, 5-Benzyl-3-[1,3]dioxolan-4-ylmethyl-2-oxo-pyrrolidin-1-yl, 3-Benzyl-5-oxo-morpholin-4-yl, 2-Benzyl-6-oxo-piperazin-1-yl, 8-Benzyl-6-methyl-10-oxo-6,9-diaza-spiro[4.5]dec-9-yl, 5-Benzyl-3-furan-2-ylmethylene-2-oxo-pyrrolidin-1-yl, 3-acetylamino-3-(sec-butyl)-2-oxo-pyrrolidin-1-yl, 3-acetylamino-3-(cyclopropylmethyl)-2-oxo-pyrrolidin-1-yl, 3-(2-amino-5-carboxypentanoylamino)-3-(sec-butyl)-2-oxo-pyrrolidin-1-yl, 3-(2-methoxy-acetylamino)-3-(sec-butyl)-2-oxo-pyrrolidin-1-yl, 3-ethoxycarbonylamino-3-(sec-butyl)-2-oxo-pyrrolidin-1-yl, 3-ethylureido-3-(sec-butyl)-2-oxo-pyrrolidin-1-yl, 3-hydroxypropionylamino-3-(sec-butyl)-2-oxo-pyrrolidin-1-yl, and the like.

In another embodiment, R₂ is selected from hydrogen, 3-Bromo-[1,2,4]thiadiazol-5-ylamino, [1,2,4]thiadiazol-5-ylamino, 4-Chloro-[1,2,5]thiadiazol-3-ylamino, [1,2,5]thiadiazol-3-ylamino, thiazol-2-ylamino, 5-Bromo-[1,3,4]thiadiazol-2-ylamino, [1,3,4]thiadiazol-2-ylamino, 5-Amino-[1,3,4]thiadiazol-2-ylamino, 2-Bromo-thiazol-5-ylamino, thiazol-5-ylamino, 5-trifluoromethyl-[1,3,4]thiadiazol-2-ylamino, 5-trifluoromethyl-[1,3,4]oxadiazol-2-ylamino, 5-Amino-[1,3,4]oxadiazol-2-ylamino, 1-trityl-1H-[1,2,4]triazol-3-ylamino, 1H-[1,2,4]triazol-3-ylamino, oxazol-2-ylamino, 5-Bromo-2-trityl-2H-[1,2,3]triazol-4-ylamino, 2-trityl-2H-[1,2,3]triazol-4-ylamino, 5-Bromo-2H-[1,2,3]triazol-4-ylamino, 2H-[1,2,3]triazol-4-ylamino, thiophen-2-ylamino, 3-methyl-5-nitro-3H-imidazol-4-ylamino, 4-Cyano-5-phenyl-isothiazol-3-ylamino, 4-phenyl-[1,2,5]thiadiazol-3-ylamino, 3,4-dioxo-cyclobut-1-enylamino, 2-methoxy-3,4-dioxo-cyclobut-1-enylamino, and 2-methylamino-3,4-dioxo-cyclobut-1-enylamino, and the like.

In another embodiment, $R_C$ is selected from

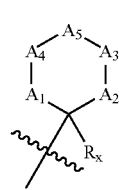

(IIId)

wherein A₅ is —C(=N—R₂₃₀) and A₁, A₂, A₃, A₄, $R_X$ and R₂₃₀ are defined above.

In another embodiment, A₅ is selected from —C(=N—OH)—, —C(=N—O—CH₃)—, —C(=N—O—CH₂CH₃)—, —C(=N—O—CH₂CH₂OH)—, —C(=N—O—CH₂CH₂NH₂)—, —C(=N—NHCH₃)—, and —C(=N—CN)—, and A₁, A₂, A₃, and A₄ are —CH₂—.

In another embodiment, A₅ is selected from —C(=N—OH)—, —C(=N—O—CH₃)—, —C(=N—O—CH₂CH₃)—, —C(=N—O—CH₂CH₂OH)—, —C(=N—O—CH₂CH₂NH₂)—, —C(=N—NHCH₃)—, and —C(=N—CN)—.

In another embodiment, $R_C$ is selected from 1-(3-tert-Butyl-phenyl)-4-hydroxyimino-cyclohexyl, 1-(3-tert-Butyl-phenyl)-4-methoxyimino-cyclohexyl, 1-(3-tert-Butyl-phenyl)-4-ethoxyimino-cyclohexyl, 1-(3-tert-Butyl-phenyl)-4-(2-hydroxy-ethoxyimino)-cyclohexyl, 1-(3-tert-Butyl-phenyl)-4-(2-amino-ethoxyimino)-cyclohexyl, 5-(3-tert-Butyl-phenyl)-2-hydroxyimino-hexahydro-pyrimidin-5-yl, 1-(3-tert-Butyl-phenyl)-4-(methyl-hydrazono)-cyclohexyl, 1-(3-tert-Butyl-phenyl)-4-cyanoimino-cyclohexyl, 5-(3-tert-Butyl-phenyl)-4,5,6,7-tetrahydro-2H-indazol-5-yl, 5-(3-tert-Butyl-phenyl)-4,5,6,7-tetrahydro-benzo[c]isoxazol-5-yl, 1-(Acrylic acid methyl ester)-4-(tert-Butyl-phenyl)-cyclohexane-4-yl, 1-(Acrylamide)-4-(tert-Butyl-phenyl)-cyclohexane-4-yl, 1-(3-tert-Butyl-phenyl)-4-(2-hydroxy-ethylidene)-cyclohex-1-yl, 1-(3-tert-Butyl-phenyl)-4-(methyl-hydrazono)-cyclohex-1-yl, 1-(3-tert-Butyl-phenyl)-4-(dimethyl-hydrazono)-cyclohex-1-yl, 4-methoxyimino-1-(3-thiophen-3-yl-phenyl)-cyclohexyl, 1-(3-furan-3-yl-phenyl)-4-methoxyimino-cyclohexyl, 4-methoxyimino-1-[3-(1H-pyrrol-2-yl)-phenyl]-cyclohexyl, 4-methoxyimino-1-(3-pyridin-4-yl-phenyl)-cyclohexyl, 4-methoxyimino-1-(3-pyrimidin-5-yl-phenyl)-cyclohexyl, 4-methoxyimino-1-(3-pyrazol-1-yl-phenyl)-cyclohexyl, 2-Acetyl-5-(3-tert-butyl-phenyl)-4,5,6,7-tetrahydro-2H-indazol-5-yl, 1-(3-tert-Butyl-phenyl)-4-methylene-cyclohexyl, ethyl 2-(4-(3-tert-butylphenyl)cyclohexylidene)acetate, and the like.

In another embodiment, $R_X$ is selected from 3-(1,1-dimethyl-propyl)-phenyl, 3-(1-ethyl-propyl)-phenyl, 3-(1H-pyrrol-2-yl)-phenyl, 3-(1-hydroxy-1-methyl-ethyl)-phenyl, 3-(1-methyl-1H-imidazol-2-yl)-phenyl, 3-(1-methyl-cyclopropyl)-phenyl, 3-(2,2-dimethyl-propyl)-phenyl, 3-(2,5-dihydro-1H-pyrrol-2-yl)-phenyl, 3-(2-Chloro-thiophen-3-yl)-phenyl, 3-(2-Cyano-thiophen-3-yl)-phenyl, 3-(2-fluoro-benzyl)-phenyl, 3-(3,5-dimethyl-3H-pyrazol-4-yl)-phenyl, 3-(3,6-dimethyl-pyrazin-2-yl)-phenyl, 3-(3-Cyano-pyrazin-2-yl)-phenyl, 3-(3-formyl-furan-2-yl)-phenyl, 3-(3H-[1,2,3]triazol-4-yl)-phenyl, 3-(3H-imidazol-4-yl)-phenyl, 3-(3-methyl-butyl)-phenyl, 3-(3-methyl-pyridin-2-yl)-phenyl, 3-(3-methyl-thiophen-2-yl)-phenyl, 3-(4-Cyano-pyridin-2-yl)-phenyl, 3-(4-fluoro-benzyl)-phenyl, 3-(4H-[1,2,4]triazol-3-yl)-phenyl, 3-(4-methyl-thiophen-2-yl)-phenyl, 3-(5-Acetyl-thiophen-2-yl)-phenyl, 3-(5-Acetyl-thiophen-3-yl)-phenyl, 3-(5-formyl-thiophen-2-yl)-phenyl, 3-(5-oxo-pyrrolidin-2-yl)-phenyl, 3-(6-methyl-pyridazin-3-yl)-phenyl, 3-(6-methyl-pyridin-2-yl)-phenyl, 3-(Cyano-dimethyl-methyl)-phenyl, 3-[1-(2-tert-Butyl-pyrimidin-4-yl)-cyclohexylamino, 3-[1,2,3]triazol-1-yl-phenyl, 3-[1,2,4]oxadiazol-3-yl-phenyl, 3-[1,2,4]oxadiazol-5-yl-phenyl, 3-[1,2,4]thiadiazol-3-yl-phenyl, 3-[1,2,4]thiadiazol-5-yl-phenyl, 3-[1,2,4]triazol-4-yl-phenyl, 3-Acetyl-5-tert-butyl-phenyl, 3'-Acetylamino-biphenyl-3-yl, 3-Adamantan-2-yl-phenyl, 3-Bromo-[1,2,4]thiadiazol-5-yl)-phenyl, 3-Bromo-5-tert-butyl-phenyl, 3-Cyano-phenyl, 3-Cyclobutyl-phenyl, 3-Cyclopentyl-phenyl, 3-Cyclopropyl-phenyl, 3-ethyl-phenyl, 3-ethynyl-phenyl, 3-fluoro-5-(2-hydroxy-1,1-dimethyl-ethyl)-phenyl, 3-furan-3-yl-phenyl, 3-imidazol-1-yl-phenyl, 3-isobutyl-phenyl, 3-isopropyl-phenyl, 3-isoxazol-3-yl-phenyl, 3-isoxazol-4-yl-phenyl, 3-isoxazol-5-yl-phenyl, 3-pent-4-enyl-phenyl, 3-pentyl-phenyl, 3-Phenyl-propionic acid ethyl ester, 3-pyrazin-2-yl-phenyl, 3-pyridin-2-yl-phenyl, 3-pyrrolidin-2-yl-phenyl, 3-sec-Butyl-phenyl, 3-tert-Butyl-4-chloro-phenyl, 3-tert-Butyl-4-cyano-phenyl, 3-tert-Butyl-4-ethyl-phenyl, 3-tert-Butyl-4-methyl-phenyl, 3-tert-Butyl-4-trifluoromethyl-phenyl, 3-tert-Butyl-5-chloro-phenyl, 3-tert-Butyl-5-cyano-phenyl, 3-tert-Butyl-5-ethyl-phenyl, 3-tert-Butyl-5-fluoro-phenyl, 3-tert-Butyl-5-methyl-phenyl, 3-tert-Butyl-5-trifluoromethyl-phenyl, 3-tert-Butyl-phenyl, 3-thiazol-2-yl-phenyl, 3-thiazol-4-yl-phenyl, 3-thiophen-3-yl-phenyl, 3-trifluoromethyl-phenyl, 4-Acetyl-3-tert-butyl-phenyl, 4-tert-Butyl-pyridin-2-yl, 4-tert-Butyl-pyrimidin-2- yl, 5-tert-Butyl-pyridazin-3-yl, and 6-tert-Butyl-pyridazin-4-yl, 6-tert-Butyl-pyrimidin-4-yl, and the like.

In another embodiment, $R_X$ is 3-tert-Butyl-phenyl.

In another embodiment, the present invention provides a method of preventing or treating at least one condition that benefits from inhibition of at least one aspartyl-protease, comprising administering to a host a composition comprising a therapeutically effective amount of at least one compound of the formula,

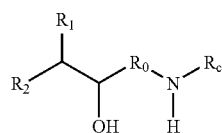

or pharmaceutically acceptable salts thereof, wherein $R_1$, $R_2$, and $R_C$ are as defined below and $R_0$ is selected from —CH(alkyl)-, —C(alkyl)$_2$-, —CH(cycloalkyl)-, —C(alkyl)(cycloalkyl)-, and —C(cycloalkyl)$_2$-.

In another embodiment, the present invention encompasses compounds of formula (I) wherein the hydroxyl substituent alpha to the —(CHR$_1$)— group, as shown in formula (I), may optionally be replaced by —NH$_2$, —NH(R$_{700}$), —N(R$_{700}$)(R$_{700}$), —SH, and —SR$_{700}$, wherein R$_{700}$ is alkyl optionally substituted with at least one group independently selected from R$_{200}$, R$_{205}$, R$_{210}$, R$_{215}$, R$_{220}$, and R$_{225}$.

Among the compounds of formula (I), or pharmaceutically acceptable salts thereof, examples include 4-[1-(3-tert-Butyl-phenyl)-4-hydroxyimino-cyclohexylamino]-2-(3,5-difluoro-benzyl)-3-hydroxy-N-methyl-butyramide, 4-[1-(3-tert-Butyl-phenyl)-4-methoxyimino-cyclohexylamino]-2-(3,5-difluoro-benzyl)-3-hydroxy-N-methyl-butyramide, 4-[1-(3-tert-Butyl-phenyl)-4-ethoxyimino-cyclohexylamino]-2-(3,5-difluoro-benzyl)-3-hydroxy-N-methyl-butyramide, 4-[1-(3-tert-Butyl-phenyl)-4-(2-hydroxy-ethoxyimino)-cyclohexylamino]-2-(3,5-difluoro-benzyl)-3-hydroxy-N-methyl-butyramide, 4-[4-(2-Amino-ethoxyimino)-1-(3-tert-butyl-phenyl)-cyclohexylamino]-2-(3,5-difluoro-benzyl)-3-hydroxy-N-methyl-butyramide, 4-[5-(3-tert-Butyl-phenyl)-2-hydroxyimino-hexahydro-pyrimidin-5-ylamino]-2-(3,5-difluoro-benzyl)-3-hydroxy-N-methyl-butyramide, 4-[1-(3-tert-Butyl-phenyl)-4-(methyl-hydrazono)-cyclohexylamino]-2-(3,5-difluoro-benzyl)-3-hydroxy-N-methyl-butyramide, 4-[1-(3-tert-Butyl-phenyl)-4-(dimethyl-hydrazono)-cyclohexylamino]-2-(3,5-difluoro-benzyl)-3-hydroxy-N-methyl-butyramide, 4-[1-(3-tert-Butyl-phenyl)-4-cyanoimino-cyclohexylamino]-2-(3,5-difluoro-benzyl)-3-hydroxy-N-methyl-butyramide, 4-[5-(3-tert-Butyl-phenyl)-4,5,6,7-tetrahydro-2H-indazol-5-ylamino]-2-(3,5-difluoro-benzyl)-3-hydroxy-N-methyl-butyramide, 4-[5-(3-tert-Butyl-phenyl)-4,5,6,7-tetrahydro-benzo[c]isoxazol-5-ylamino]-2-(3,5-difluoro-benzyl)-3-hydroxy-N-methyl-butyramide, 4-[1-(3-tert-Butyl-phenyl)-4-methylcarbamoylmethylene-cyclohexylamino]-2-(3,5-difluoro-benzyl)-3-hydroxy-N-methyl-butyramide, {4-(3-tert-Butyl-phenyl)-4-[4-(3,5-difluoro-phenyl)-2-hydroxy-3-methylcarbamoyl-butylamino]-cyclohexylidene}-acetic acid methyl ester, 4-[1-(3-tert-Butyl-phenyl)-4-(2-hydroxy-ethylidene)-cyclohexylamino]-2-(3,5-difluoro-benzyl)-3-hydroxy-N-methyl-butyramide, 4-[1-(3-tert-Butyl-phenyl)-4-hydroxyimino-cyclohexylamino]-2-(3,5-difluoro-benzyl)-3-hydroxy-N-phenyl-butyramide, 4-[1-(3-tert-Butyl-phenyl)-4-methoxyimino-cyclohexylamino]-2-(3,5-difluoro-benzyl)-3-hydroxy-N-phenyl-butyramide, 4-[1-(3-tert-Butyl-phenyl)-4-ethoxyimino-cyclohexylamino]-2-(3,5-difluoro-benzyl)-3-hydroxy-N-phenyl-butyramide, 4-[1-(3-tert-Butyl-phenyl)-4-(2-hydroxy-ethoxyimino)-cyclohexylamino]-2-(3,5-difluoro-benzyl)-3-hydroxy-N-phenyl-butyramide, 4-[4-(2-Amino-ethoxyimino)-1-(3-tert-butyl-phenyl)-cyclohexylamino]-2-(3,5-difluoro-benzyl)-3-hydroxy-N-phenyl-butyramide, 4-[5-(3-tert-Butyl-phenyl)-2-hydroxyimino-hexahydro-pyrimidin-5-ylamino]-2-(3,5-difluoro-benzyl)-3-hydroxy-N-phenyl-butyramide, 4-[1-(3-tert-Butyl-phenyl)-4-(methyl-hydrazono)-cyclohexylamino]-2-(3,5-difluoro-benzyl)-3-hydroxy-N-phenyl-butyramide, 4-[1-(3-tert-Butyl-phenyl)-4-(dimethyl-hydrazono)-cyclohexylamino]-2-(3,5-difluoro-benzyl)-3-hydroxy-N-phenyl-butyramide, 4-[1-(3-tert-Butyl-phenyl)-4-cyanoimino-cyclohexylamino]-2-(3,5-difluoro-benzyl)-3-hydroxy-N-phenyl-butyramide, 4-[5-(3-tert-Butyl-phenyl)-4,5,6,7-tetrahydro-2H-indazol-5-ylamino]-2-(3,5-difluoro-benzyl)-3-hydroxy-N-phenyl-butyramide, 4-[5-(3-tert-Butyl-phenyl)-4,5,6,7-tetrahydro-benzo[c]isoxazol-5-ylamino]-2-(3,5-difluoro-benzyl)-3-hydroxy-N-phenyl-butyramide, 4-[1-(3-tert-Butyl-phenyl)-4-methylcarbamoylmethylene-cyclohexylamino]-2-(3,5-difluoro-benzyl)-3-hydroxy-N-phenyl-butyramide, {4-(3-tert-Butyl-phenyl)-4-[4-(3,5-difluoro-phenyl)-2-hydroxy-3-phenylcarbamoyl-butylamino]-cyclohexylidene}-acetic acid methyl ester, 4-[1-(3-tert-Butyl-phenyl)-4-(2-hydroxy-ethylidene)-cyclohexylamino]-2-(3,5-difluoro-benzyl)-3-hydroxy-N-phenyl-butyramide, 4-(3-tert-Butyl-phenyl)-4-[4-(3,5-difluoro-phenyl)-2-hydroxy-3-(1H-imidazol-2-yl)-butylamino]-cyclohexanone oxime, 4-(3-tert-Butyl-phenyl)-4-[4-(3,5-difluoro-phenyl)-2-hydroxy-butylamino]-cyclohexanone oxime, 4-(3-tert-Butyl-phenyl)-4-[3-(3,5-difluoro-phenoxy)-2-hydroxy-propylamino]-cyclohexanone oxime, 4-(3-tert-Butyl-phenyl)-4-[3-(3,5-difluoro-benzenesulfonyl)-2-hydroxy-propylamino]-cyclohexanone oxime, 4-(3-tert-Butyl-phenyl)-4-[4-(3,5-difluoro-phenyl)-2-hydroxy-4-oxo-butylamino]-cyclohexanone oxime, 4-(3-tert-Butyl-phenyl)-4-[4-(3,5-difluoro-phenyl)-2-hydroxy-pentylamino]-cyclohexanone oxime, 4-(3-tert-Butyl-phenyl)-4-[4-(3,5-difluoro-phenyl)-2-hydroxy-pentylamino]-cyclohexanone oxime, 4-(3-tert-Butyl-phenyl)-4-[4-(3,5-difluoro-phenyl)-2-hydroxy-3-tetrazol-1-yl-butylamino]-cyclohexanone oxime, 4-(3-tert-Butyl-phenyl)-4-[4-(3,5-difluoro-phenyl)-2-hydroxy-3-(5-trifluoromethyl-[1,3,4]oxadiazol-2-yl)-butylamino]-cyclohexanone oxime, 4-(3-tert-Butyl-phenyl)-4-[4-(3,5-difluoro-phenyl)-2-hydroxy-3-([1,2,4]thiadiazol-5-ylamino)-butylamino]-cyclohexanone oxime, 3-[3-[1-(3-tert-Butyl-phenyl)-4-hydroxyimino-cyclohexylamino]-1-(3,5-difluoro-benzyl)-2-hydroxy-propylamino]-4-methylamino-cyclobut-3-ene-1,2-dione, 3-[3-[1-(3-tert-Butyl-phenyl)-4-hydroxyimino-cyclohexylamino]-1-(3,5-difluoro-benzyl)-2-hydroxy-propylamino]-4-methoxy-cyclobut-3-ene-1,2-dione, 4-(3-tert-Butyl-phenyl)-4-[2-hydroxy-4-(3-propyl-thiophen-2-yl)-3-([1,2,4]thiadiazol-5-ylamino)-butylamino]-cyclohexanone oxime, 1-(5-(3-tert-butylphenyl)-4,5,6,7-tetrahydro-2H-indazol-5-ylamino)-4-(3,5-difluorophenyl)butan-2-ol, 1-(5-(3-tert-butylphenyl)-2-methyl-4,5,6,7-tetrahydro-2H-indazol-5-ylamino)-4-(3,5-difluorophenyl)butan-2-ol, and the like.

The present invention encompasses methods of treatment using compounds with structural characteristics designed for interacting with their target molecules. Such characteristics include at least one moiety capable of interacting with at least one subsite of beta-secretase. Such characteristics also include at least one moiety capable of enhancing the interaction between the target and at least one subsite of beta-secretase.

It is preferred that the compounds of formula (I) are efficacious. For example, it is preferred that the compounds of formula (I) decrease the level of beta-secretase using low dosages of the compounds. Preferably, the compounds of formula (I) decrease the level of A-beta by at least 10% using dosages of about 100 mg/kg. It is more preferred that the compounds of formula (I) decrease the level of A-beta by at least 10% using dosages of less than 100 mg/kg. It is also more preferred that the compounds of formula (I) decrease the level of A-beta by greater than 10% using dosages of about 100 mg/kg. It is most preferred that the compounds of formula (I) decrease the level of A-beta by greater than 10% using dosages of less than 100 mg/kg.

In an embodiment, the host is a cell.

In another embodiment, the host is an animal.

In another embodiment, the host is human.

In another embodiment, at least one compound of formula (I) is administered in combination with a pharmaceutically acceptable carrier or diluent.

In another embodiment, the pharmaceutical compositions comprising compounds of formula (I) can be used to treat a wide variety of disorders or conditions including Alzheimer's disease, Down's syndrome or Trisomy 21 (including mild cognitive impairment (MCI) Down's syndrome), hereditary cerebral hemorrhage with amyloidosis of the Dutch type, chronic inflammation due to amyloidosis, prion diseases (including Creutzfeldt-Jakob disease, Gerstmann-Straussler syndrome, kuru scrapie, and animal scrapie), Familial Amyloidotic Polyneuropathy, cerebral amyloid angiopathy, other degenerative dementias including dementias of mixed vascular and degenerative origin, dementia associated with Parkinson's disease, dementia associated with progressive supranuclear palsy and dementia associated with cortical basal degeneration, diffuse Lewy body type of Alzheimer's disease, and frontotemporal dementias with parkinsonism (FTDP).

In another embodiment, the condition is Alzheimer's disease.

In another embodiment, the condition is dementia.

When treating or preventing these diseases, the methods of the present invention can either employ the compounds of formula (I) individually or in combination, as is best for the patient.

In treating a patient displaying any of the conditions discussed above, a physician may employ a compound of formula (I) immediately and continue administration indefinitely, as needed. In treating patients who are not diagnosed as having Alzheimer's disease, but who are believed to be at substantial risk for it, the physician may start treatment when the patient first experiences early pre-Alzheimer's symptoms, such as memory or cognitive problems associated with aging. In addition, there are some patients who may be determined to be at risk for developing Alzheimer's disease through the detection of a genetic marker such as APOE4 or other biological indicators that are predictive for Alzheimer's disease and related conditions. In these situations, even though the patient does not have symptoms of the disease or condition, administration of the compounds of formula (I) may be started before symptoms appear, and treatment may be continued indefinitely to prevent or delay the onset of the disease. Similar protocols are provided for other diseases and conditions associated with amyloidosis, such as those characterized by dementia.

In an embodiment, the methods of preventing or treating at least one condition associated with amyloidosis, comprising administering to a host a composition comprising a therapeutically effective amount of at least one compound of formula (I), which may include beta-secretase complexed with at least one compound of formula (I), or at least one pharmaceutically acceptable salt thereof, wherein $R_1$, $R_2$, and $R_C$ are as previously defined.

One embodiment of the present invention provides a method of preventing or treating the onset of Alzheimer's disease comprising administering to a patient a therapeutically effective amount of at least one compound of formula (I), or at least one pharmaceutically acceptable salt thereof, wherein $R_1$, $R_2$, and $R_C$ are as previously defined.

Another embodiment of the present invention provides a method of preventing or treating the onset of dementia comprising administering to a patient a therapeutically effective amount of at least one compound of formula (I), or at least one pharmaceutically acceptable salt thereof, wherein $R_1$, $R_2$, and $R_C$ are as previously defined.

Another embodiment of the present invention provides a method of preventing or treating at least one condition associated with amyloidosis by administering to a host an effective amount of at least one compound of formula (I), or at least one pharmaceutically acceptable salt thereof, wherein $R_1$, $R_2$, and $R_C$ are as previously defined.

Another embodiment of the present invention provides a method of preventing or treating Alzheimer's disease by administering to a host an effective amount of at least one compound of formula (I), or at least one pharmaceutically acceptable salt thereof, wherein $R_1$, $R_2$, and $R_C$ are as previously defined.

Another embodiment of the present invention provides a method of preventing or treating dementia by administering to a host an effective amount of at least one compound of formula (I), or at least one pharmaceutically acceptable salt thereof, wherein $R_1$, $R_2$, and $R_C$ are as previously defined.

Another embodiment of the present invention provides a method of inhibiting beta-secretase activity in a cell. This method comprises administering to the cell an effective amount of at least one compound of formula (I), or at least one pharmaceutically acceptable salt thereof, wherein $R_1$, $R_2$, and $R_C$ are as previously defined.

Another embodiment of the present invention provides a method of inhibiting beta-secretase activity in a host. This method comprises administering to the host an effective amount of at least one compound of formula (I), or at least one pharmaceutically acceptable salt thereof, wherein $R_1$, $R_2$, and $R_C$ are as previously defined.

Another embodiment of the present invention provides a method of inhibiting beta-secretase activity in a host. This method comprises administering to the host an effective amount of at least one compound of formula (I), or at least one pharmaceutically acceptable salt thereof, wherein $R_1$, $R_2$, and $R_C$ are as previously defined, and wherein the host is a human.

Another embodiment of the present invention provides methods of affecting beta-secretase-mediated cleavage of amyloid precursor protein in a patient, comprising administering a therapeutically effective amount of at least one compound of formula (I), or at least one pharmaceutically acceptable salt thereof, wherein $R_1$, $R_2$, and $R_C$ are as previously defined.

Another embodiment of the present invention provides a method of inhibiting cleavage of amyloid precursor protein at a site between Met596 and Asp597 (numbered for the APP-695 amino acid isotype), or at a corresponding site of an isotype or mutant thereof, comprising administering a therapeutically effective amount of at least one compound of formula (I), or at least one pharmaceutically acceptable salt thereof, wherein $R_1$, $R_2$, and $R_C$ are as previously defined.

Another embodiment of the present invention provides a method of inhibiting cleavage of amyloid precursor protein or mutant thereof at a site between amino acids, comprising administering a therapeutically effective amount of at least one compound of formula (I), or at least one pharmaceutically acceptable salt thereof, wherein $R_1$, $R_2$, and $R_C$ are as previously defined, and wherein the site between amino acids corresponds to between Met652 and Asp653 (numbered for the APP-751 isotype), between Met671 and Asp672 (numbered for the APP-770 isotype), between Leu596 and Asp597 of the APP-695 Swedish Mutation, between Leu652 and Asp653 of the APP-751 Swedish Mutation, or between Leu671 and Asp672 of the APP-770 Swedish Mutation.

Another embodiment of the present invention provides a method of inhibiting production of A-beta, comprising administering to a patient a therapeutically effective amount of at least one compound of formula (I), or at least one pharmaceutically acceptable salt thereof, wherein $R_1$, $R_2$, and $R_C$ are as previously defined.

Another embodiment of the present invention provides a method of preventing or treating deposition of A-beta, comprising administering a therapeutically effective amount of at least one compound of formula (I), or at least one pharmaceutically acceptable salt thereof, wherein $R_1$, $R_2$, and $R_C$ are as previously defined.

Another embodiment of the present invention provides a method of preventing, delaying, halting, or reversing a disease characterized by A-beta deposits or plaques, comprising administering a therapeutically effective amount of at least one compound of formula (I), or at least one pharmaceutically acceptable salt thereof, wherein $R_1$, $R_2$, and $R_C$ are as previously defined.

In one embodiment the A-beta deposits or plaques are in a human brain.

Another embodiment of the present invention provides a method of preventing, delaying, halting, or reversing a condition associated with a pathological form of A-beta in a host comprising administering to a patient in need thereof an effective amount of at least one compound of formula (I), or at least one pharmaceutically acceptable salt thereof, wherein $R_1$, $R_2$, and $R_C$ are as previously defined.

Another embodiment of the present invention provides a method of inhibiting the activity of at least one aspartyl protease in a patient in need thereof, comprising administering a therapeutically effective amount of at least one compound of formula (I), or at least one pharmaceutically acceptable salt thereof to the patient, wherein $R_1$, $R_2$, and $R_C$ are as previously defined.

In one embodiment, the at least one aspartyl protease is beta-secretase.

Another embodiment of the present invention provides a method of interacting an inhibitor with beta-secretase, comprising administering to a patient in need thereof a therapeutically effective amount of at least one compound of formula (I), or at least one pharmaceutically acceptable salt thereof, wherein $R_1$, $R_2$, and $R_C$ are as previously defined, and wherein the at least one compound interacts with at least one beta-secretase subsite such as S1, S1', or S2'.

Another embodiment provides a method of selecting compounds of formula (I) wherein the pharmacokinetic parameters are adjusted for a an increase in desired effect (e.g., increased brain uptake).

Another embodiment provides a method of selecting at least one compound of formula (I) wherein $C_{max}$, $T_{max}$, and/or half-life are adjusted to provide for maximum efficacy.

Another embodiment of the present invention provides a method of treating a condition in a patient, comprising administering a therapeutically effective amount of at least one compound of formula (I), or at least one pharmaceutically acceptable salt, derivative or biologically active metabolite thereof, to the patient, wherein $R_1$, $R_2$, and $R_C$ are as previously defined.

In an embodiment, the condition is Alzheimer's disease.

In another embodiment, the condition is dementia.

In another embodiment, the compounds of formula (I) are administered in oral dosage form. The oral dosage forms are generally administered to the patient 1, 2, 3, or 4 times daily. It is preferred that the compounds be administered either three or fewer times daily, more preferably once or twice daily. It is preferred that, whatever oral dosage form is used, it be designed so as to protect the compounds from the acidic environment of the stomach. Enteric coated tablets are well known to those skilled in the art. In addition, capsules filled with small spheres, each coated to be protected from the acidic stomach, are also well known to those skilled in the art.

Therapeutically effective amounts include, for example, oral administration from about 0.1 mg/day to about 1,000 mg/day, parenteral, sublingual, intranasal, intrathecal administration from about 0.2 mg/day to about 100 mg/day, depot administration and implants from about 0.5 mg/day to about 50 mg/day, topical administration from about 0.5 mg/day to about 200 mg/day, and rectal administration from about 0.5 mg/day to about 500 mg/day.

When administered orally, an administered amount therapeutically effective to inhibit beta-secretase activity, to inhibit A-beta production, to inhibit A-beta deposition, or to treat or prevent Alzheimer's disease is from about 0.1 mg/day to about 1,000 mg/day.

In various embodiments, the therapeutically effective amount may be administered in, for example, pill, tablet, capsule, powder, gel, or elixir form, and/or combinations thereof. It is understood that, while a patient may be started at one dose or method of administration, that dose or method of administration may vary over time as the patient's condition changes.

Another embodiment of the present invention provides a method of prescribing a medication for preventing, delaying, halting, or reversing at least one disorder, condition or disease associated with amyloidosis. The method includes identifying in a patient symptoms associated with at least one disorder, condition or disease associated with amyloidosis, and prescribing at least one dosage form of at least one compound of formula (I), or at least one pharmaceutically acceptable salt, to the patient, wherein $R_1$, $R_2$, and $R_C$ are as previously defined.

Another embodiment of the present invention provides an article of manufacture, comprising (a) at least one dosage form of at least one compound of formula (I), or at least one pharmaceutically acceptable salt thereof, wherein $R_1$, $R_2$, and $R_C$ are as previously defined, (b) a package insert providing that a dosage form comprising a compound of formula (I) should be administered to a patient in need of therapy for at least one disorder, condition or disease associated with amyloidosis, and (c) at least one container in which at least one dosage form of at least one compound of formula (I) is stored.

Another embodiment provides a packaged pharmaceutical composition for treating at least one condition related to amyloidosis, comprising (a) a container which holds an effective amount of at least one compound of formula (I), or at least one pharmaceutically acceptable salt thereof, and (b) instructions for using the pharmaceutical composition.

Another embodiment of the present invention provides an article of manufacture, comprising (a) a therapeutically effective amount of at least one compound of formula (I), or pharmaceutically acceptable salt thereof, wherein $R_1$, $R_2$, and $R_C$ are as previously defined, (b) a package insert providing an oral dosage form should be administered to a patient in need of therapy for at least one disorder, condition or disease associated with amyloidosis, and (c) at least one container comprising at least one oral dosage form of at least one compound of formula (I).

Another embodiment of the present invention provides an article of manufacture, comprising (a) at least one oral dosage form of at least one compound of formula (I), or at least one pharmaceutically acceptable salt thereof, wherein $R_1$, $R_2$, and $R_C$ are as previously defined, in a dosage amount ranging from about 2 mg to about 1000 mg, associated with (b) a package insert providing that an oral dosage form comprising a compound of formula (I) in a dosage amount ranging from about 2 mg to about 1000 mg should be administered to a patient in need of therapy for at least one disorder, condition or disease associated with amyloidosis, and (c) at least one container in which at least one oral dosage form of at least one compound of formula (I) in a dosage amount ranging from about 2 mg to about 1000 mg is stored.

Another embodiment of the present invention provides an article of manufacture, comprising (a) at least one oral dosage form of at least one compound of formula (I) in a dosage amount ranging from about 2 mg to about 1000 mg in combination with (b) at least one therapeutically active agent, associated with (c) a package insert providing that an oral dosage form comprising a compound of formula (I) in a dosage amount ranging from about 2 mg to about 1000 mg in combination with at least one therapeutically active agent should be administered to a patient in need of therapy for at least one disorder, condition or disease associated with amyloidosis, and (d) at least one container in which at least one dosage form of at least one compound of formula (I) in a dosage amount ranging from about 2 mg to about 1000 mg in combination with a therapeutically active agent is stored.

Another embodiment of the present invention provides an article of manufacture, comprising (a) at least one parenteral dosage form of at least one compound of formula (I) or at least one pharmaceutically acceptable salt thereof, in a dosage amount ranging from about 0.2 mg/mL to about 50 mg/mL, associated with (b) a package insert providing that a parenteral dosage form comprising a compound of formula (I) in a dosage amount ranging from about 0.2 mg/mL to about 50 mg/mL should be administered to a patient in need of therapy for at least one disorder, condition or disease associated with amyloidosis, and (c) at least one container in which at least one parenteral dosage form of at least one compound of formula (I), or at least one pharmaceutically acceptable salt thereof, in a dosage amount ranging from about 0.2 mg/mL to about 50 mg/mL is stored.

A further embodiment of the present invention provides an article of manufacture comprising (a) a medicament comprising an effective amount of at least one compound of formula (I) or at least one pharmaceutically acceptable salt thereof, in combination with active and/or inactive pharmaceutical agents, (b) a package insert providing that an effective amount of at least one compound of formula (I) should be administered to a patient in need of therapy for at least one disorder, condition or disease associated with amyloidosis, and (c) a container in which a medicament comprising an effective amount of at least one compound of formula (I) in combination with a therapeutically active and/or inactive agent is stored.

In an embodiment, the therapeutically active agent is selected from an antioxidant, an anti-inflammatory, a gamma-secretase inhibitor, a neurotrophic agent, an acetyl cholinesterase inhibitor, a statin, an A-beta, and/or an anti-A-beta antibody.

Another embodiment of the present invention provides an article of manufacture comprising: (a) a medicament comprising: an effective amount of at least one compound of formula (I),

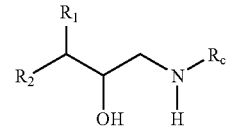

(I)

or at least one pharmaceutically acceptable salt thereof, wherein $R_1$, $R_2$, and $R_C$ are defined bellow, in combination with active and/or inactive pharmaceutical agents; (b) a package insert providing that an effective amount of at least one compound of formula (I) should be administered to a patient in need of therapy for at least one disorder, condition or disease associated with amyloidosis; and (c) a container in which a medicament comprising: an effective amount of at least one compound of formula (I) in combination with active and/or inactive pharmaceutical agents is stored.

Another embodiment of the present invention provides a kit comprising: (a) at least one dosage form of at least one compound of formula (I); and (b) at least one container in which at least one dosage form of at least one compound of formula (I) is stored.

In an embodiment, the kit further comprises a package insert: a) containing information of the dosage amount and duration of exposure of a dosage form containing at least one compound of formula (I), or at least one pharmaceutically acceptable salt thereof, and b) providing that the dosage form should be administered to a patient in need of therapy for at least one disorder, condition or disease associated with amyloidosis.

In another embodiment, the kit further comprises at least one therapeutically active agent.

In another embodiment of a kit, the therapeutically active agent is selected from an antioxidant, an anti-inflammatory, a gamma-secretase inhibitor, a neurotrophic agent, an acetyl cholinesterase inhibitor, a statin, an A-beta, and an anti-A-beta antibody.

A further embodiment of the present invention provides method of preventing or treating at least one condition associated with amyloidosis, comprising: administering to a host a composition comprising a therapeutically effective amount of at least one selective beta-secretase inhibitor of formula (I), or at least one pharmaceutically acceptable salt thereof, further comprising a composition including beta-secretase complexed with at least one compound of formula (I), wherein $R_1$, $R_2$, and $R_C$ are defined bellow, or pharmaceutically acceptable salt thereof.

Another embodiment of the present invention provides a method of producing a beta-secretase complex comprising exposing beta-secretase to a compound of formula (I), or at least one pharmaceutically acceptable salt thereof, in a reaction mixture under conditions suitable for the production of the complex.

Another embodiment of the present invention provides a manufacture of a medicament for preventing, delaying, halting, or reversing Alzheimer's disease, comprising adding an effective amount of at least one compound of formula (I), or at least one pharmaceutically acceptable salt thereof, wherein $R_1$, $R_2$, and $R_C$ are defined below, to a pharmaceutically acceptable carrier.

Another embodiment of the present invention provides a method of selecting a beta-secretase inhibitor comprising targeting at least one moiety of at least one formula (I) compound, or at least one pharmaceutically acceptable salt thereof, to interact with at least one beta-secretase subsite such as but not limited to S1, S1', or S2'.

The methods of treatment described herein include administering the compounds of formula (I) orally, parenterally (via intravenous injection (IV), intramuscular injection (IM), depo-IM, subcutaneous injection (SC or SQ), or depo-SQ), sublingually, intranasally (inhalation), intrathecally, topically, or rectally. Dosage forms known to those skilled in the art are suitable for delivery of the compounds of formula (I).

In treating or preventing the above diseases, the compounds of formula (I) are administered using a therapeutically effective amount. The therapeutically effective amount will vary depending on the particular compound used and the route of administration, as is known to those skilled in the art.

The compositions are preferably formulated as suitable pharmaceutical preparations, such as for example, pill, tablet, capsule, powder, gel, or elixir form, and/or combinations thereof, for oral administration or in sterile solutions or suspensions for parenteral administration. Typically the compounds described above are formulated into pharmaceutical compositions using techniques and/or procedures well known in the art.

For example, a therapeutically effective amount of a compound or mixture of compounds of formula (I), or a physiologically acceptable salt is combined with a physiologically acceptable vehicle, carrier, binder, preservative, stabilizer, flavor, and the like, in a unit dosage form as called for by accepted pharmaceutical practice and is defined herein. The amount of active substance in those compositions or preparations is such that a suitable dosage in the range indicated is obtained. The compound concentration is effective for delivery of an amount upon administration that lessens or ameliorates at least one symptom of the disorder for which the compound is administered. For example, the compositions can be formulated in a unit dosage form, each dosage containing from about 2 mg to about 1000 mg.

The active ingredient may be administered in a single dose, or may be divided into a number of smaller doses to be administered at intervals of time. It is understood that the precise dosage and duration of treatment is a function of the disease or condition being treated and may be determined empirically using known testing protocols or by extrapolation from in vivo or in vitro test data. It is to be noted that concentrations and dosage values may vary with the severity of the condition to be alleviated. It is also to be understood that the precise dosage and treatment regimens may be adjusted over time according to the individual need and the professional judgment of the person administering or supervising the administration of the compositions, and that the concentration ranges set forth-herein are exemplary only and are not intended to limit the scope or practice of the claimed compositions. A dosage and/or treatment method for any particular patient also may depend on, for example, the age, weight, sex, diet, and/or health of the patient, the time of administration, and/or any relevant drug combinations or interactions.

To prepare compositions to be employed in the methods of treatment, at least one compound of formula (I) or at least one pharmaceutically acceptable salt thereof, wherein $R_1$, $R_2$, and $R_C$ are defined below, is mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. An effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. Additionally, the active materials can also be mixed with other active materials that do not impair the desired action, or with materials that supplement the desired action, or have another action. For example, the compounds of formula (I) may be formulated as the sole pharmaceutically active ingredient in the composition or may be combined with other active ingredients.

Where the compounds exhibit insufficient solubility, methods for solubilizing may be used. Such methods are known and include, for example, using co-solvents (such as dimethylsulfoxide (DMSO)), using surfactants (such as Tween®), and/or dissolution in aqueous sodium bicarbonate. Derivatives of the compounds, such as salts, metabolites, and/or pro-drugs, may also be used in formulating effective pharmaceutical compositions. Such derivatives may improve the pharmacokinetic properties of treatment administered.

A kit may include a plurality of containers, each container holding at least one unit dose of the compound of the present invention. The containers are preferably adapted for the desired mode of administration, including, for example, pill, tablet, capsule, powder, gel or gel capsule, sustained-release capsule, or elixir form, and/or combinations thereof and the like for oral administration, depot products, pre-filled syringes, ampoules, vials, and the like for parenteral administration, and patches, medipads, creams, and the like for topical administration.

The tablets, pills, capsules, troches, and the like may contain a binder (e.g., gum tragacanth, acacia, corn starch, gelatin, and the like); a vehicle (e.g., microcrystalline cellulose, starch, lactose, and the like); a disintegrating agent (e.g., alginic acid, corn starch, and the like); a lubricant (e.g., magnesium stearate, and the like); a gildant (e.g., colloidal silicon dioxide, and the like); a sweetening agent (e.g., sucrose, saccharin, and the like); a flavoring agent (e.g., peppermint, methyl salicylate, and the like); or fruit flavoring; compounds of a similar nature, and/or mixtures thereof.

When the dosage unit form is a capsule, it can contain, in addition to material described above, a liquid carrier such as a fatty oil. Additionally, dosage unit forms can contain various other materials, which modify the physical form of the dosage unit, for example, coatings of sugar or other enteric agents. A method of treatment can also administer the compound as a component of an elixir, suspension, syrup, wafer, chewing gum, or the like. A syrup may contain, in addition to the active compounds, sucrose as a sweetening agent, flavors, preservatives, dyes and/or colorings.

The methods of treatment may employ at least one carrier that protects the compound against rapid elimination from the body, such as time-release formulations or coatings. Such carriers include controlled release formulations, such as, for example, implants or microencapsulated delivery systems, and the like or biodegradable, biocompatible polymers such as collagen, ethylene vinyl acetate, polyanhydrides, polyglycolic acid, polyorthoesters, polylactic acid, and the like. Methods for preparation of such formulations are known to those in the art.

When orally administered, the compounds of the present invention can be administered in usual dosage forms for oral administration as is well known to those skilled in the art. These dosage forms include the usual solid unit dosage forms of tablets and capsules as well as liquid dosage forms such as solutions, suspensions, and elixirs. When solid dosage forms are used, it is preferred that they be of the sustained release type so that the compounds of the present invention need to be administered only once or twice daily. When liquid oral dosage forms are used, it is preferred that they be of about 10 mL to about 30 mL each. Multiple doses may be administered daily.

The methods of treatment may also employ a mixture of the active materials and other active or inactive materials that do not impair the desired action, or with materials that supplement the desired action.

Solutions or suspensions used for parenteral, intradermal, subcutaneous, or topical application can include a sterile diluent (e.g., water for injection, saline solution, fixed oil, and the like); a naturally occurring vegetable oil (e.g., sesame oil, coconut oil, peanut oil, cottonseed oil, and the like); a synthetic fatty vehicle (e.g., ethyl oleate, polyethylene glycol, glycerine, propylene glycol, and the like, including other synthetic solvents); antimicrobial agents (e.g., benzyl alcohol, methyl parabens, and the like); antioxidants (e.g., ascorbic acid, sodium bisulfite, and the like); chelating agents (e.g., ethylenediaminetetraacetic acid (EDTA) and the like); buffers (e.g., acetates, citrates, phosphates, and the like); and/or agents for the adjustment of tonicity (e.g., sodium chloride, dextrose, and the like); or mixtures thereof.

Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and the like, and mixtures thereof. Liposomal suspensions including tissue-targeted liposomes may also be suitable as pharmaceutically acceptable carriers. These may be prepared according to methods known, for example, as described in U.S. Pat. No. 4,522,811.

The methods of treatment include delivery of the compounds of the present invention in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The methods of treatment include administration of the compounds parenterally, for example, by IV, IM, SC, or depo-SC. When administered parenterally, a therapeutically effective amount of about 0.2 mg/mL to about 50 mg/mL is preferred. When a depot or IM formulation is used for injection once a month or once every two weeks, the preferred dose should be about 0.2 mg/mL to about 50 mg/mL.

The methods of treatment include administration of the compounds sublingually. When given sublingually, the compounds of the present invention should be given one to four times daily in the amounts described above for IM administration.

The methods of treatment include administration of the compounds intranasally. When given by this route, the appropriate dosage forms are a nasal spray or dry powder, as is known to those skilled in the art. The dosage of the compounds of the present invention for intranasal administration is the amount described above for IM administration.

The methods of treatment include administration of the compounds intrathecally. When given by this route the appropriate dosage form can be a parenteral dosage form as is known to those skilled in the art. The dosage of the compounds of the present invention for intrathecal administration is the amount described above for IM administration.

The methods of treatment include administration of the compounds topically. When given by this route, the appropriate dosage form is a cream, ointment, or patch. When topically administered, the dosage is from about 0.2 mg/day to about 200 mg/day. Because the amount that can be delivered by a patch is limited, two or more patches may be used. The number and size of the patch is not important. What is important is that a therapeutically effective amount of a compound of the present invention be delivered as is known to those skilled in the art. The compound can be administered rectally by suppository as is known to those skilled in the art. When administered by suppository, the therapeutically effective amount is from about 0.2 mg to about 500 mg.

The methods of treatment include administration of the compounds by implants as is known to those skilled in the art. When administering a compound of the present invention by implant, the therapeutically effective amount is the amount described above for depot administration.

Given a particular compound of the present invention and/or a desired dosage form and medium, one skilled in the art would know how to prepare and administer the appropriate dosage form and/or amount.

The methods of treatment include use of the compounds of the present invention, or acceptable pharmaceutical salts thereof, in combination, with each other or with other therapeutic agents, to treat or prevent the conditions listed above. Such agents or approaches include acetylcholine esterase inhibitors such as tacrine (tetrahydroaminoacridine, marketed as COGNEX®), donepezil hydrochloride, (marketed as Aricept®) and rivastigmine (marketed as Exelon®), gamma-secretase inhibitors, anti-inflammatory agents such as cyclooxygenase II inhibitors, anti-oxidants such as Vitamin E or ginkolides, immunological approaches, such as, for example, immunization with A-beta peptide or administration of anti-A-beta peptide antibodies, statins, and direct or indirect neurotropic agents such as Cerebrolysin®, AIT-082

(Emilien, 2000, *Arch. Neurol.* 57:454), and other neurotropic agents, and complexes with beta-secretase or fragments thereof.

Additionally, methods of treatment of the present invention also employ the compounds of the present invention with inhibitors of P-glycoprotein (P-gp). P-gp inhibitors and the use of such compounds are known to those skilled in the art. See, for example, *Cancer Research*, 53, 4595-4602 (1993), *Clin. Cancer Res.*, 2, 7-12 (1996), *Cancer Research*, 56, 4171-4179 (1996), International Publications WO 99/64001 and WO 01/10387. The blood level of the P-gp inhibitor should be such that it exerts its effect in inhibiting P-gp from decreasing brain blood levels of the compounds of formula (I). To that end the P-gp inhibitor and the compounds of formula (I) can be administered at the same time, by the same or different route of administration, or at different times. Given a particular compound of formula (I), one skilled in the art would know whether a P-gp inhibitor is desirable for use in the method of treatment, which P-gp inhibitor should be used, and how to prepare and administer the appropriate dosage form and/or amount.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102,918, quinoline-3-carboxylic acid (2-{4-[2-(6,7-dimethyl-3,4-dihydro-1H-isoquinoline-2-yl)-ethyl]phenylcarbamoyl}-4,5-dimethylphenyl)-amide (Xenova), or other compounds. Compounds that have the same function and therefore achieve the same outcome are also considered to be useful.

The P-gp inhibitors can be administered orally, parenterally, (via IV, IM, depo-IM, SQ, depo-SQ), topically, sublingually, rectally, intranasally, intrathecally, or by implant.

The therapeutically effective amount of the P-gp inhibitors is from about 0.1 mg/kg to about 300 mg/kg daily, preferably about 0.1 mg/kg to about 150 mg/kg daily. It is understood that while a patient may be started on one dose, that dose may vary over time as the patient's condition changes.

When administered orally, the P-gp inhibitors can be administered in usual dosage forms for oral administration as is known to those skilled in the art. These dosage forms include the usual solid unit dosage forms of tablets or capsules as well as liquid dosage forms such as solutions, suspensions or elixirs. When the solid dosage forms are used, it is preferred that they be of the sustained release type so that the P-gp inhibitors need to be administered only once or twice daily. The oral dosage forms are administered to the patient one through four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that the dosage form used is designed to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered via IV, IM, depo-IM, SQ or depo-SQ.

The P-gp inhibitors can be given sublingually. When given sublingually, the P-gp inhibitors should be given one through four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository or by implants, both of which are known to those skilled in the art.

It should be apparent to one skilled in the art that the exact dosage and frequency of administration will depend on the particular compounds of the present invention administered, the particular condition being treated, the severity of the condition being treated, the age, weight, or general physical condition of the particular patient, or any other medication the individual may be taking as is well known to administering physicians who are skilled in this art.

Another embodiment of the present invention provides a method of preventing or treating at least one condition associated with amyloidosis using compounds with increased oral bioavailability (increased F values).

Another embodiment of the present invention provides methods for preventing or treating at least one condition associated with amyloidosis, comprising administering to a host, a therapeutically effective amount of at least one compound of formula (I), or at least one pharmaceutically acceptable salt thereof, wherein $R_1$, $R_2$, and $R_C$ are as previously defined, and wherein the compound has an F value of at least 10%.

In another embodiment, the host is an animal.

In another embodiment, the host is human.

In another embodiment, the F value is greater than about 20%. In yet a further embodiment, the F value is greater than about 30%.

Another embodiment of the present invention provides methods of preventing or treating at least one condition associated with amyloidosis using compounds with a high degree of selectivity.

Investigation of potential beta-secretase inhibitors produced compounds with increased selectivity for beta-secretase over other aspartyl proteases such as cathepsin D (catD), cathepsin E (catE), Human Immunodeficiency Viral (HIV) protease, and renin. Selectivity was calculated as a ratio of inhibition ($IC_{50}$) values in which the inhibition of beta-secretase was compared to the inhibition of other aspartyl proteases. A compound is selective when the $IC_{50}$ value (i.e., concentration required for 50% inhibition) of a desired target (e.g., beta-secretase) is less than the $IC_{50}$ value of a secondary target (e.g., catD).

Alternatively, a compound is selective when its binding affinity is greater for its desired target (e.g., beta-secretase) versus a secondary target (e.g., catD).

Accordingly, methods of treatment include administering selective compounds of formula (I) having a lower $IC_{50}$ value for inhibiting beta-secretase, or greater binding affinity for beta-secretase, than for other aspartyl proteases such as catD, catE, HIV protease, or renin. A selective compound is also capable of producing a higher ratio of desired effects to adverse effects, resulting in a safer method of treatment.

Exemplary compounds of formula (I) are provided in the Examples below.

EXAMPLE 1

Exemplary Formula (I) Compounds

| EXAMPLE No. | Compound |
|---|---|
| 1-1. | 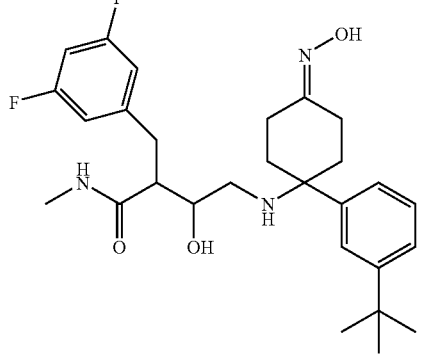<br>4-[1-(3-tert-Butyl-phenyl)-4-hydroxyimino-cyclohexylamino]-2-(3,5-difluoro-benzyl)-3-hydroxy-N-methyl-butyramide |
| 1-2. | 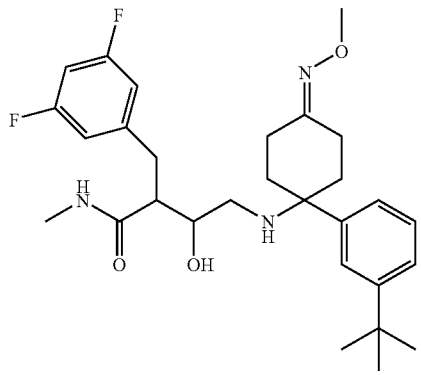<br>4-[1-(3-tert-Butyl-phenyl)-4-methoxyimino-cyclohexylamino]-2-(3,5-difluoro-benzyl)-3-hydroxy-N-methyl-butyramide |
| 1-3. | 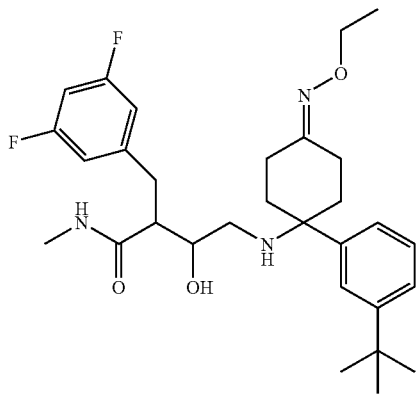<br>4-[1-(3-tert-Butyl-phenyl)-4-ethoxyimino-cyclohexylamino]-2-(3,5-difluoro-benzyl)-3-hydroxy-N-methyl-butyramide |
| 1-4. | 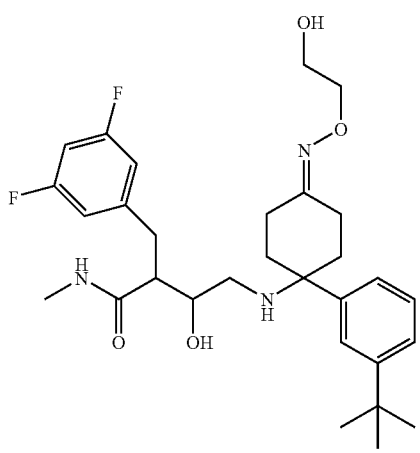<br>4-[1-(3-tert-Butyl-phenyl)-4-(2-hydroxy-ethoxyimino)-cyclohexylamino]-2-(3,5-difluoro-benzyl)-3-hydroxy-N-methyl-butyramide |
| 1-5. | 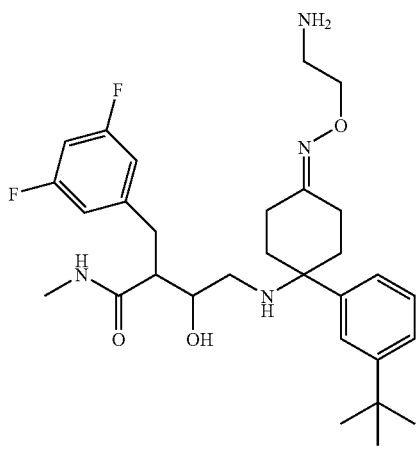<br>4-[4-(2-Amino-ethoxyimino)-1-(3-tert-butyl-phenyl)-cyclohexylamino]-2-(3,5-difluoro-benzyl)-3-hydroxy-N-methyl-butyramide |

-continued

| EXAMPLE No. | Compound |
|---|---|
| 1-6. | 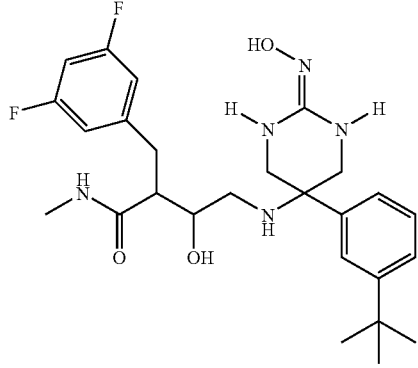<br>4-[5-(3-tert-Butyl-phenyl)-2-hydroxyimino-hexahydro-pyrimidin-5-ylamino]-2-(3,5-difluoro-benzyl)-3-hydroxy-N-methyl-butyramide |
| 1-7. | 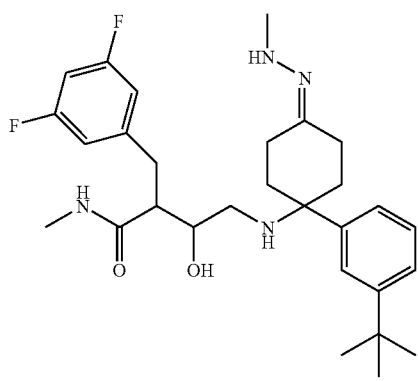<br>4-[1-(3-tert-Butyl-phenyl)-4-(methyl-hydrazono)-cyclohexyl-amino]-2-(3,5-difluoro-benzyl)-3-hydroxy-N-methyl-butyramide |
| 1-8. | 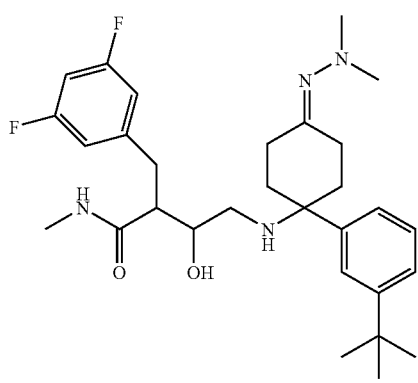<br>4-[1-(3-tert-Butyl-phenyl)-4-(dimethyl-hydrazono)-cyclohexyl-amino]-2-(3,5-difluoro-benzyl)-3-hydroxy-N-methyl-butyramide |

-continued

| EXAMPLE No. | Compound |
|---|---|
| 1-9. | 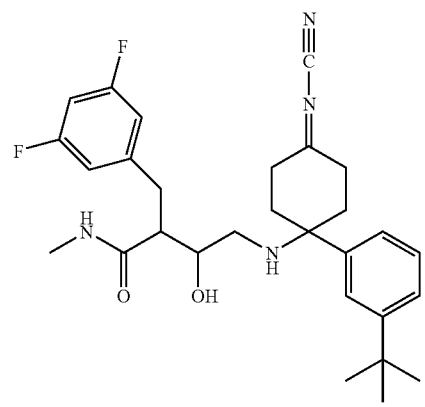<br>4-[1-(3-tert-Butyl-phenyl)-4-cyanoimino-cyclohexylamino]-2-(3,5-difluoro-benzyl)-3-hydroxy-N-methyl-butyramide |
| 1-10. | 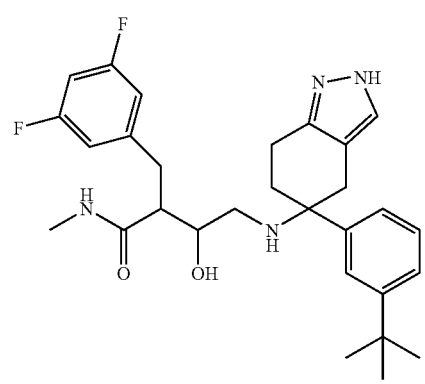<br>4-[5-(3-tert-Butyl-phenyl)-4,5,6,7-tetrahydro-2H-indazol-5-yl-amino]-2-(3,5-difluoro-benzyl)-3-hydroxy-N-methyl-butyramide |
| 1-11. | 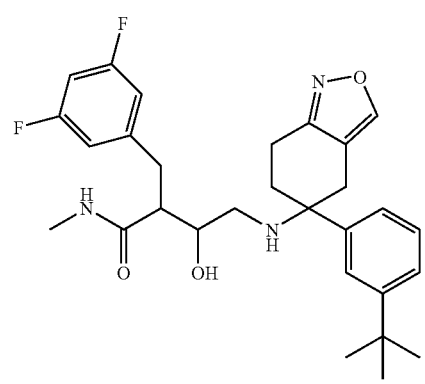<br>4-[5-(3-tert-Butyl-phenyl)-4,5,6,7-tetrahydro-benzo[c]isoxazol-5-ylamino]-2-(3,5-difluoro-benzyl)-3-hydroxy-N-methyl-butyramide |

| EX-AMPLE No. | Compound |
|---|---|
| 1-12. | 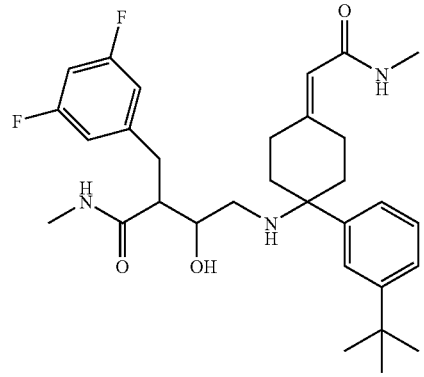 4-[1-(3-tert-Butyl-phenyl)-4-methylcarbamoylmethylene-cyclo-hexylamino]-2-(3,5-difluoro-benzyl)-3-hydroxy-N-methyl-butyramide |
| 1-13. | 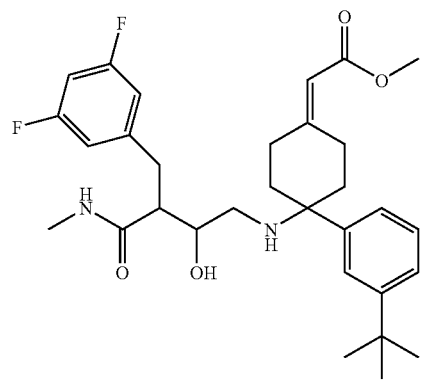 {4-(3-tert-Butyl-phenyl)-4-[4-(3,5-difluoro-phenyl)-2-hydroxy-3-methylcarbamoyl-butylamino]-cyclohexylidene}-acetic acid methyl ester |
| 1-14. | 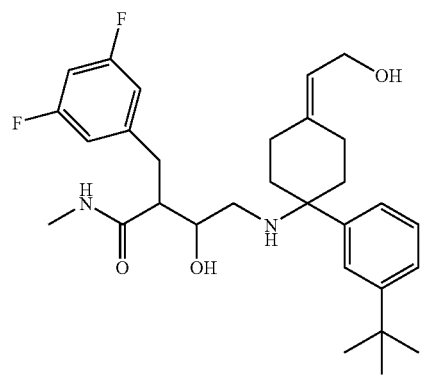 4-[1-(3-tert-Butyl-phenyl)-4-(2-hydroxy-ethylidene)-cyclohexyl-amino]-2-(3,5-difluoro-benzyl)-3-hydroxy-N-methyl-butyramide |
| 1-15. | 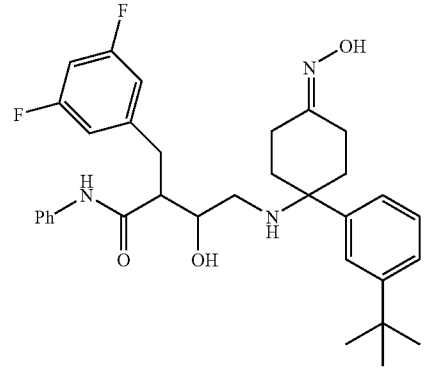 4-[1-(3-tert-Butyl-phenyl)-4-hydroxyimino-cyclohexylamino]-2-(3,5-difluoro-benzyl)-3-hydroxy-N-phenyl-butyramide |
| 1-16. | 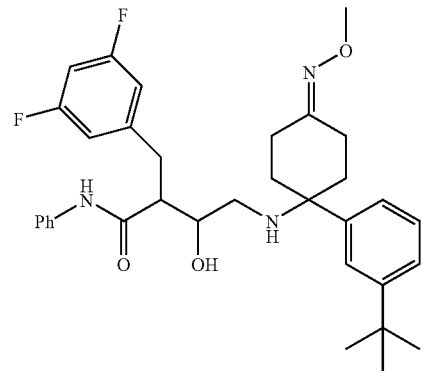 4-[1-(3-tert-Butyl-phenyl)-4-methoxyimino-cyclohexylamino]-2-(3,5-difluoro-benzyl)-3-hydroxy-N-phenyl-butyramide |
| 1-17. | 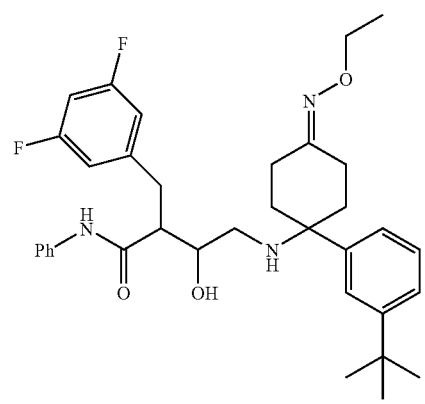 4-[1-(3-tert-Butyl-phenyl)-4-ethoxyimino-cyclohexylamino]-2-(3,5-difluoro-benzyl)-3-hydroxy-N-phenyl-butyramide |

| EXAMPLE No. | Compound |
|---|---|
| 1-18. | 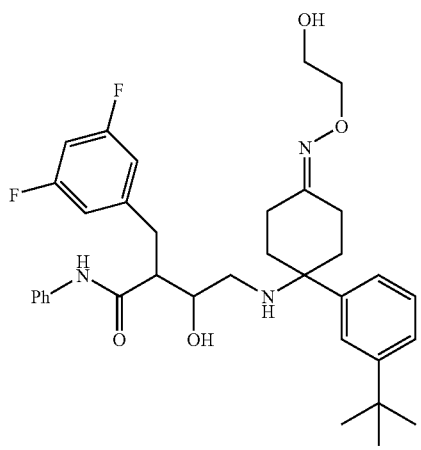<br>4-[1-(3-tert-Butyl-phenyl)-4-(2-hydroxy-ethoxyimino)-cyclohexylamino]-2-(3,5-difluoro-benzyl)-3-hydroxy-N-phenyl-butyramide |
| 1.19. | 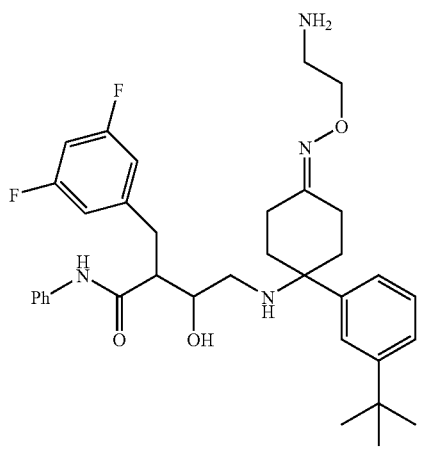<br>4-[4-(2-Amino-ethoxyimino)-1-(3-tert-butyl-phenyl)-cyclohexylamino]-2-(3,5-difluoro-benzyl)-3-hydroxy-N-phenyl-butyramide |
| 1-20. | 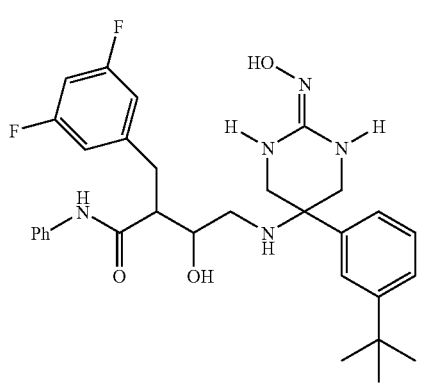<br>4-[5-(3-tert-Butyl-phenyl)-2-hydroxyimino-hexahydro-pyrimidin-5-ylamino]-2-(3,5-difluoro-benzyl)-3-hydroxy-N-phenyl-butyramide |
| 1-21. | 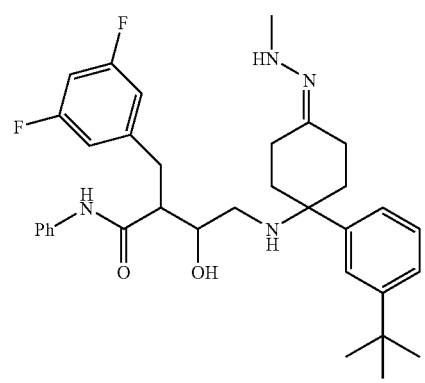<br>4-[1-(3-tert-Butyl-phenyl)-4-(methyl-hydrazono)-cyclohexylamino]-2-(3,5-difluoro-benzyl)-3-hydroxy-N-phenyl-butyramide |
| 1-22. | 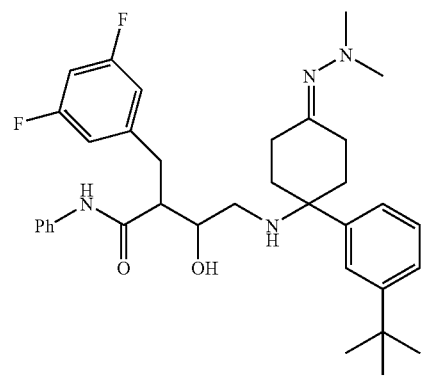<br>4-[1-(3-tert-Butyl-phenyl)-4-(dimethyl-hydrazono)-cyclohexylamino]-2-(3,5-difluoro-benzyl)-3-hydroxy-N-phenyl-butyramide |
| 1-23. | 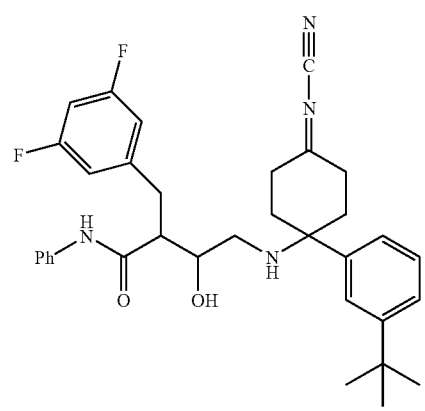<br>4-[1-(3-tert-Butyl-phenyl)-4-cyanoimino-cyclohexylamino]-2-(3,5-difluoro-benzyl)-3-hydroxy-N-phenyl-butyramide |

| EX-AMPLE No. | Compound |
|---|---|
| 1-24. | 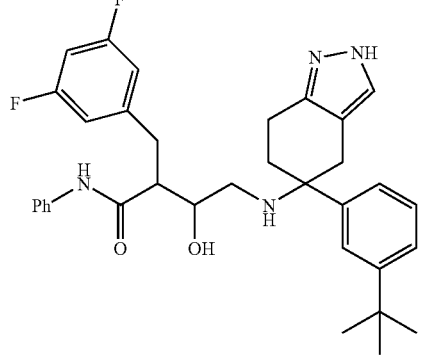<br>4-[5-(3-tert-Butyl-phenyl)-4,5,6,7-tetrahydro-2H-indazol-5-yl-amino]-2-(3,5-difluoro-benzyl)-3-hydroxy-N-phenyl-butyramide |
| 1-25. | 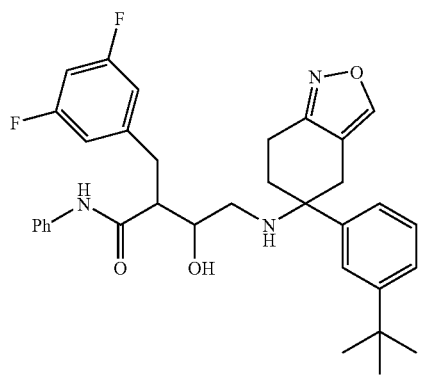<br>4-[5-(3-tert-Butyl-phenyl)-4,5,6,7-tetrahydro-benzo[c]isoxazol-5-ylamino]-2-(3,5-difluoro-benzyl)-3-hydroxy-N-phenyl-butyramide |
| 1-26. | 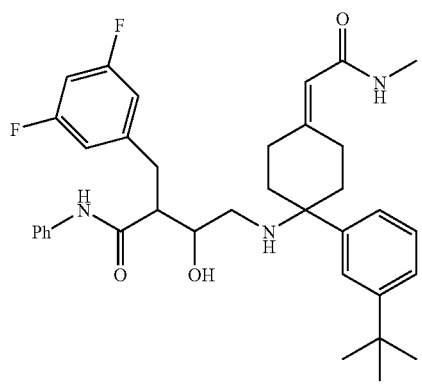<br>4-[1-(3-tert-Butyl-phenyl)-4-methylcarbamoylmethylene-cyclohexylamino]-2-[3,5-difluoro-benzyl)-3-hydroxy-N-phenyl-butyramide |
| 1-27. | 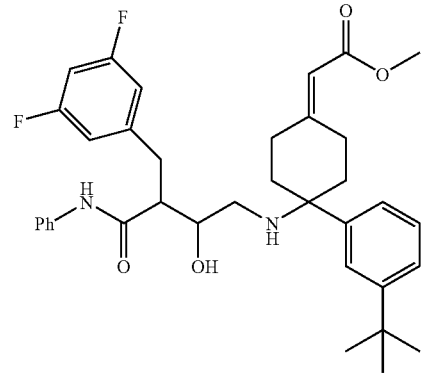<br>{4-(3-tert-Butyl-phenyl)-4-[4-(3,5-difluoro-phenyl)-2-hydroxy-3-phenylcarbamoyl-butylamino]-cyclohexylidene}-acetic acid methyl ester |
| 1-28. | 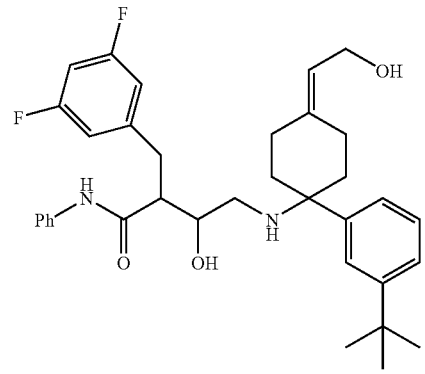<br>4-[1-(3-tert-Butyl-phenyl)-4-(2-hydroxy-ethylidene)-cyclohexyl-amino]-2-(3,5-difluoro-benzyl)-3-hydroxy-N-phenyl-butyramide |
| 1-29. | 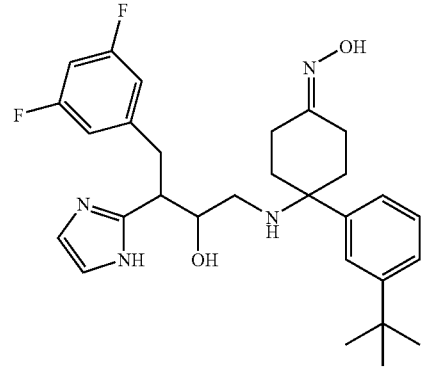<br>4-(3-tert-Butyl-phenyl)-4-[4-(3,5-difluoro-phenyl)-2-hydroxy-3-(1H-imidazol-2-yl)-butylamino]-cyclohexanone oxime |

-continued

| EX-AMPLE No. | Compound |
|---|---|
| 1-30. | 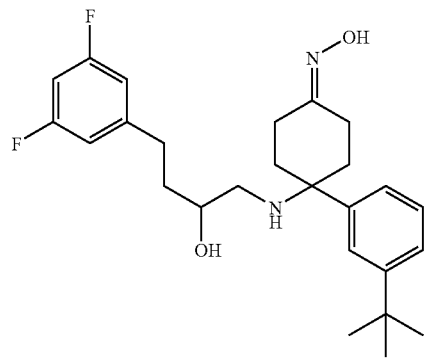<br>4-(3-tert-Butyl-phenyl)-4-[4-(3,5-difluoro-phenyl)-2-hydroxy-butylamino]-cyclohexanone oxime |
| 1-31. | 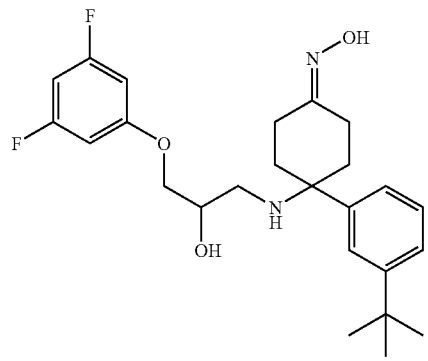<br>4-(3-tert-Butyl-phenyl)-4-[3-(3,5-difluoro-phenoxy)-2-hydroxy-propylamino]-cyclohexanone oxime |
| 1-32. | 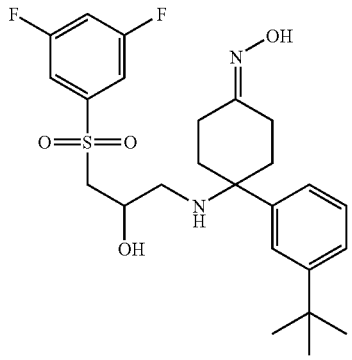<br>4-(3-tert-Butyl-phenyl)-4-[3-(3,5-difluoro-benzenesulfonyl)-2-hydroxy-propylamino]-cyclohexanone oxime |

-continued

| EX-AMPLE No. | Compound |
|---|---|
| 1-33. | 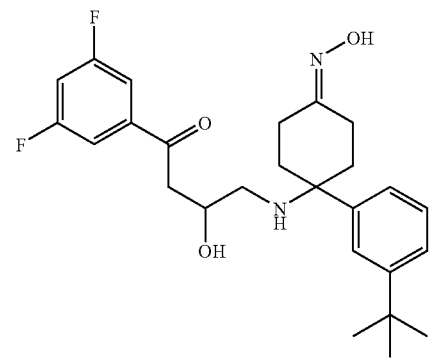<br>4-(3-tert-Butyl-phenyl)-4-[4-(3,5-difluoro-phenyl)-2-hydroxy-4-oxo-butylamino]-cyclohexanone oxime |
| 1-34. | 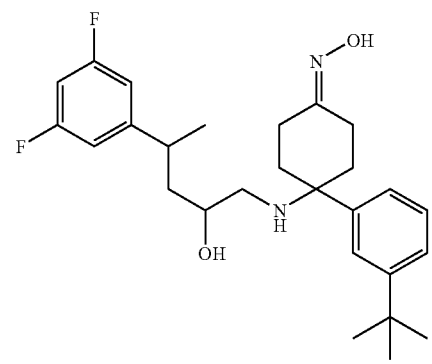<br>4-(3-tert-Butyl-phenyl)-4-[4-(3,5-difluoro-phenyl)-2-hydroxy-pentylamino]-cyclohexanone oxime |
| 1-35. | 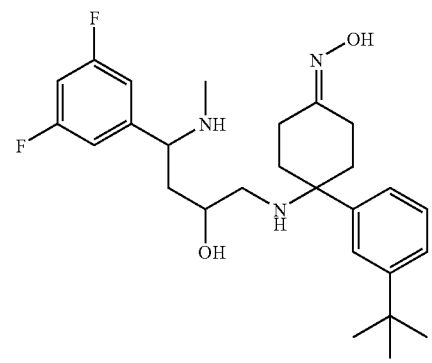<br>4-(3-tert-Butyl-phenyl)-4-[4-(3,5-difluoro-phenyl)-2-hydroxy-pentylamino]-cyclohexanone oxime |

| EX-AMPLE No. | Compound |
|---|---|
| 1-36. | 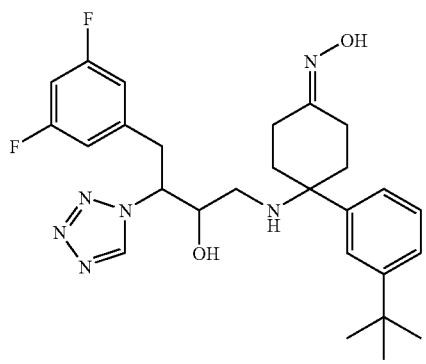<br>4-(3-tert-Butyl-phenyl)-4-[4-(3,5-difluoro-phenyl)-2-hydroxy-3-tetrazol-1-yl-butylamino]-cyclohexanone oxime |
| 1-37. | 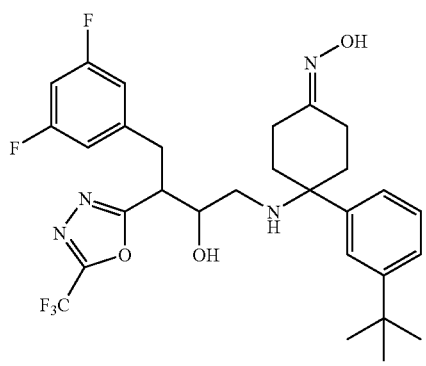<br>4-(3-tert-Butyl-phenyl)-4-[4-(3,5-difluoro-phenyl)-2-hydroxy-3-(5-trifluoromethyl-[1,3,4]oxadiazol-2-yl)-butylamino]-cyclohexanone oxime |
| 1-38. | 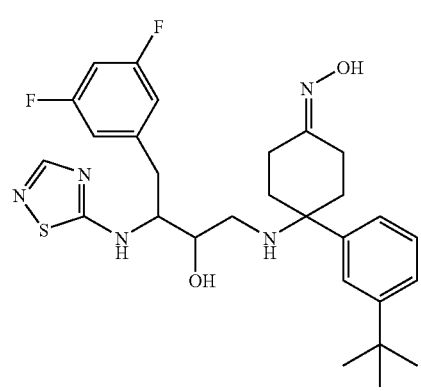<br>4-(3-tert-Butyl-phenyl)-4-[4-(3,5-difluoro-phenyl)-2-hydroxy-3-([1,2,4]thiadiazol-5-ylamino)-butylamino]-cyclohexanone oxime |
| 1-39. | 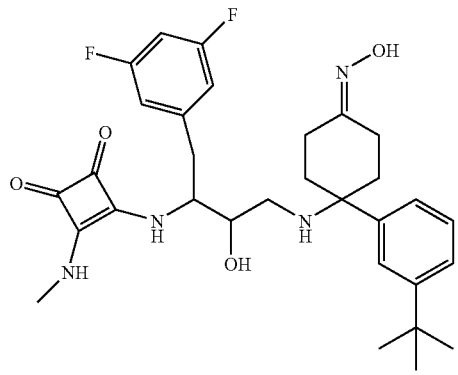<br>3-[3-[1-(3-tert-Butyl-phenyl)-4-hydroxyimino-cyclohexylamino]-1-(3,5-difluoro-benzyl)-2-hydroxy-propylamino]-4-methylamino-cyclobut-3-ene-1,2-dione |
| 1-40. | 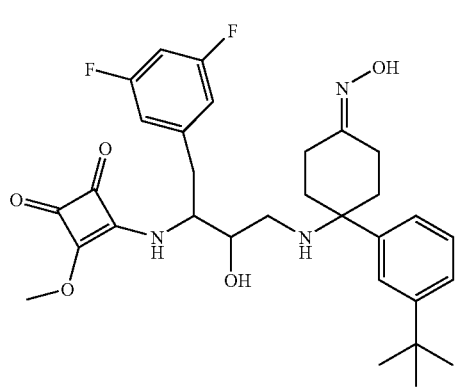<br>3-[3-[1-(3-tert-Butyl-phenyl)-4-hydroxyimino-cyclohexylamino]-1-(3,5-difluoro-benzyl)-2-hydroxy-propylamino]-4-methoxy-cyclobut-3-ene-1,2-dione |
| 1-41. | 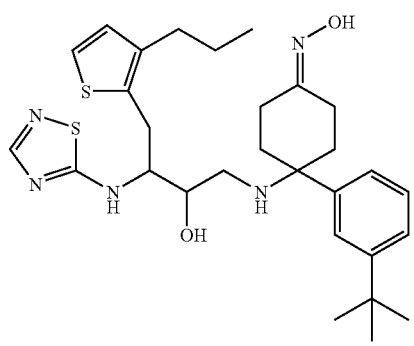<br>4-(3-tert-Butyl-phenyl)-4-[2-hydroxy-4-(3-propyl-thiophen-2-yl)-3-([1,2,4]thiadiazol-5-ylamino)-butylamino]-cyclohexanone oxime |

| EX-AMPLE No. | Compound |
|---|---|
| 1-42. | 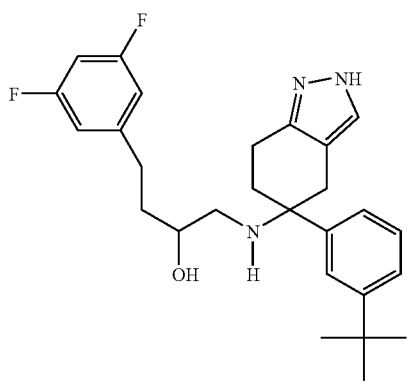<br>1-(5-(3-tert-butylphenyl)-4,5,6,7-tetrahydro-2H-indazol-5-ylamino)-4-(3,5-difluorophenyl)butan-2-ol |
| 1-43. | 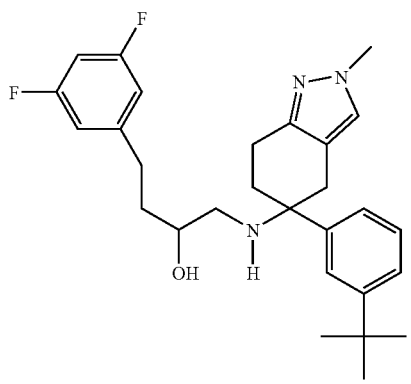<br>1-(5-(3-tert-butylphenyl)-2-methyl-4,5,6,7-tetrahydro-2H-indazol-5-ylamino)-4-(3,5-difluorophenyl)butan-2-ol |

EXPERIMENTAL PROCEDURES

The compounds and the methods of treatment of the present invention can be prepared by one skilled in the art based on knowledge of the compound's chemical structure. The chemistry for the preparation of the compounds employed in the methods of treatment of this invention is known to those skilled in the art. In fact, there is more than one process to prepare the compounds employed in the methods of treatment of the present invention. Specific examples of methods of preparation can be found in the art. For examples, see Zuccarello et al., *J. Org. Chem.* 1998, 63, 4898-4906; Benedetti et al., *J. Org. Chem.* 1997, 62, 9348-9353; Kang et al., *J. Org. Chem.* 1996, 61, 5528-5531; Kempf et al., *J. Med. Chem.* 1993, 36, 320-330; Lee et al., *J. Am. Chem. Soc.* 1999, 121, 1145-1155; and references cited therein; *Chem. Pharm. Bull.* (2000), 48(11), 1702-1710; *J. Am. Chem. Soc.* (1974), 96(8), 2463-72; *Ind. J. Chem.*, §B: *Organic Chemistry Including Medicinal Chemistry* (2003), 42B(4), 910-915; and *J. Chem. Soc.* §C: *Organic* (1971), (9), 1658-10. See also U.S. Pat. Nos. 6,150,530, 5,892,052, 5,696,270, and 5,362,912, and references cited therein, which are incorporated herein by reference.

$^1$H and $^{13}$C NMR spectra were obtained on a Varian 400 MHz, Varian 300 MHz, or Bruker 300 MHz instrument and as described in the above examples. Unless otherwise stated, HPLC samples were analyzed using a YMC ODS-AQ S-3 120 A 3.0×50 mm cartridge, with a standard gradient from 5% acetonitrile containing 0.01% heptafluorobutyric acid (HFBA) and 1% isopropanol in water containing 0.01% HFBA to 95% acetonitrile containing 0.01% HFBA and 1% isopropanol in water containing 0.01% HFBA over 5 minutes. Mass spec samples were performed with electron spray ionization (ESI).

Exemplary HPLC Procedures

Various High Pressure Liquid Chromatography (HPLC) procedures employed the following methods:

Method [1] utilizes a 20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [2] utilizes a 50% [B]: 50% [A] to 95% [B]: 5% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [3] utilizes a 5% [B]: 95% [A] to 20% [B]: 80% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [4] utilizes a 20% [B]: 80% [A] to 70% [B]: 30% [A] gradient in 2.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [5] utilizes a 50% [B]: 50% [A] to 95% [B]: 5% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [6] utilizes a 5% [B]: 95% [A] to 20% [B]: 80% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [7] utilizes a 20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [8] utilizes a YMC ODS-AQ S-3 120 A 3.0×50 mm cartridge, with a standard gradient from 5% acetonitrile containing 0.01% heptafluorobutyric acid (HFBA) and 1% isopropanol in water containing 0.01% HFBA to 95% acetonitrile containing 0.01% HFBA and 1% isopropanol in water containing 0.01% HFBA over 5 min.

Method [9] utilizes a 20% [B]: 80% [A] to 70% [B]: 30% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

EXAMPLE 2

General Preparation of Formula (I) Compounds

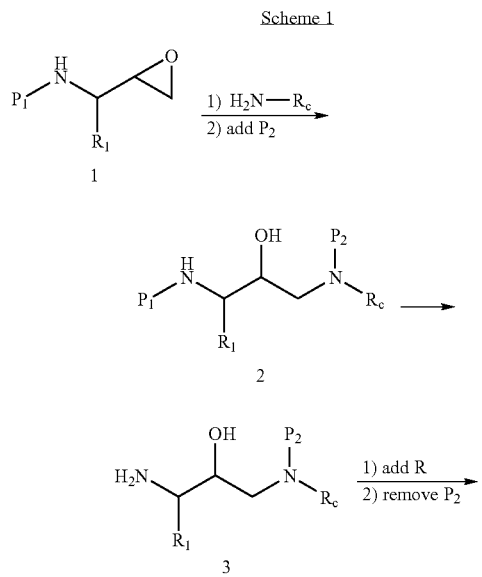

The general synthesis of compounds of formula (I) are shown in the above Scheme 1, and Schemes 2 and 3 below. In Scheme 1, chiral epoxides (1), which were derived from amino acids and are known in the art (see Luly, J. R. et al. *J. Org. Chem.* 1987, 52, 1487; Tucker, T. J. et al. *J. Med. Chem.* 1992, 35, 2525), were treated with 1.5-5 equivalents of primary amine $H_2N$—$R_C$ in a $C_1$-$C_6$ alcoholic solvent, such as ethanol, isopropanol, or sec-butanol to effect ring opening of the epoxide. The reactions can be run at temperatures ranging from about 20-25° C. up to about the reflux temperature of the alcohol employed. The preferred temperature range for conducting the reaction is between 40° C. and the refluxing temperature of the alcohol employed. A more preferred embodiment is to perform this reaction at reflux in isopropanol.

The resulting amino alcohol is protected with capping group $P_2$. Appropriate protecting groups such as tert-butoxycarbonyl (Boc) or benzyloxycarbonyl (Cbz) may be introduced via treatment with the appropriate anhydride or carbamoyl chloride as known in the art in order to provide compounds of type 2. It is preferred to select protecting groups $P_2$ which may be orthogonally removed independently from $P_1$.

The protecting group $P_1$ is removed affording the corresponding amine by means known to those skilled in the art for removal of amine protecting groups. For example, it is preferred to remove the preferred protecting group, Boc, by dissolving 2 in a trifluoroacetic acid/dichloromethane (1/1) mixture. When complete, the solvents are removed under reduced pressure yielding the corresponding amine (3) (as the corresponding salt, i.e. trifluoroacetic acid salt) which is used without further purification. If desired, the amine can be purified further by means well known to those skilled in the art, such as, for example, recrystallization. Further, if the non-salt form is desired, it also can be obtained by means known to those skilled in the art, such as, for example, preparing the free base amine via treatment of the salt with mild basic conditions. Additional Boc deprotection conditions and deprotection conditions for other protecting groups can be found in T. W. Green and P. G. M. Wuts in *Protecting Groups in Organic Chemistry*, $3^{rd}$ edition, John Wiley and Sons, 1999.

The addition of the group R may be achieved by a variety of methods known in the art, depending on the nature of R, and can be found in R. C. Larock's *Comprehensive Organic Transformations*, VCH Publishers, 1989, e.g., pp. 972, 979, and 981. Removal of the protecting group $P_2$ by methods known in the art would then afford 4.

EXAMPLE 3

Alternative Preparation of Formula (I) Compounds

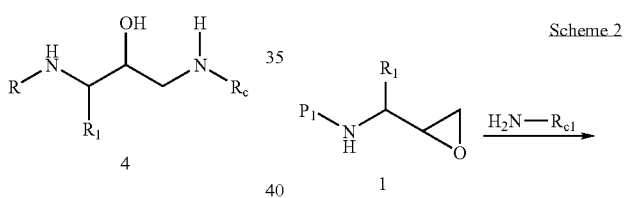

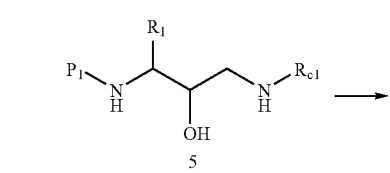

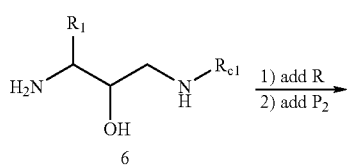

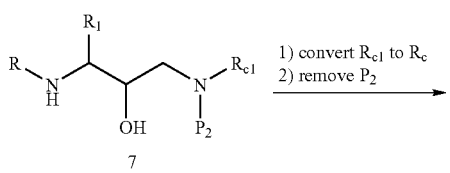

-continued

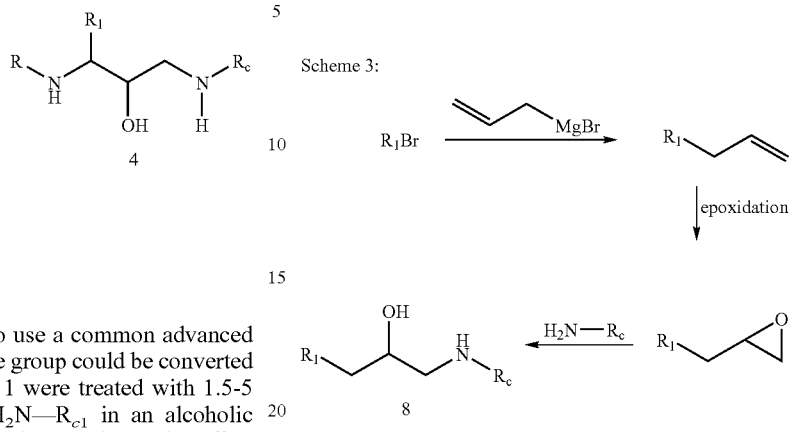

An alternative approach was to use a common advanced intermediate 7 by which a reactive group could be converted to yield compounds 4. Epoxides 1 were treated with 1.5-5 equivalents of primary amine $H_2N$—$R_{c1}$ in an alcoholic solvent, such as ethanol, isopropanol, or sec-butanol to effect ring opening of the epoxide. In an embodiment, this reaction is prepared at elevated temperatures from 40° C. to reflux. In another embodiment, this reaction is performed at reflux in isopropanol. The resulting amino alcohol 5 was then deprotected.

When $R_{c1}$ contains a labile functional group, such as an aryl iodide, aryl bromide, aryl trifluoromethanesulfonate, or aryl boronic ester, which may be converted into $R_C$ via transition metal-mediated coupling, this allows for the rapid synthesis of a variety of analogs 4. Such conversions may include Suzuki (aryl boronic acid or boronic ester and aryl halide), Negishi (arylzinc and aryl or vinyl halide), and Sonogashira (arylzinc and alkynyl halide) couplings. Subsequent to the coupling reaction, the protecting group $P_2$ is removed in methods known in the art to yield compounds 4.

EXAMPLE 4

Alternative Preparation of Formula (I) Compounds

As described herein, one embodiment of the present invention provides for compounds of formula 8 as shown above in Scheme 3. These compounds may be made by methods known to those skilled in the art from starting compounds that are also known to those skilled in the art. The process chemistry is further well known to those skilled in the art. A suitable process for the preparation of compounds of formula 8 is set forth in Scheme 3 above.

EXAMPLE 5

Prepatation of 8-(3-ISOPROPYLPHENYL)-1,4-DIOXA-SPIRO[4.5]DECANE-8-AMINE ACETATE (11)

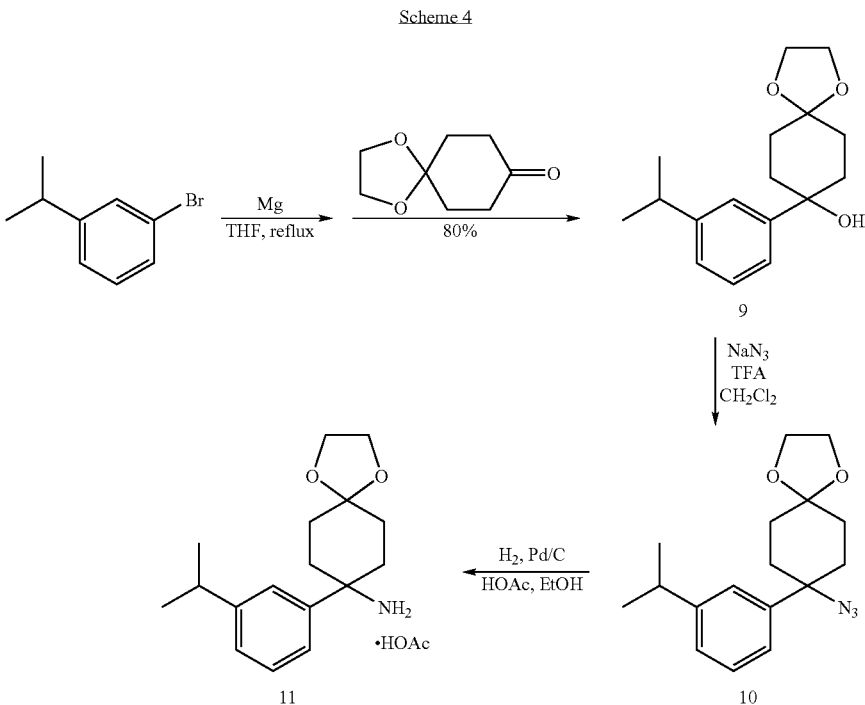

Step 1. Preparation of 8-(3-isopropylphenyl)-1,4-dioxa-spiro[4.5]decane-8-alcohol (9)

A solution of 3-bromoisopropylbenzene (25 mmol) in 20 mL of dry THF was added dropwise over 20 min to 1.22 g (50 mmol) of magnesium turnings in 10 mL of refluxing THF under nitrogen and the mixture was refluxed for an additional 25 min to form the Grignard reagent. The Grignard solution was cooled and added by cannula to a suspension of CuBr-dimethylsulfide complex (0.52 g, 2.5 mmol) in dry THF at −25° C. The suspension was stirred at −25° C. for 20 min, and then a solution of 1,4 cyclohexanedione, monoethylene ketal (3.9 g, 25 mmol) in 15 mL of THF was added dropwise over 5 min. The mixture was allowed to gradually warm to ambient temperature. After chromatography over silica gel, eluting with 20% to 30% ethyl acetate in heptane, alcohol 9 (5.6 g, 20 mmol, 80%) was isolated as a colorless oil which crystallized to a white solid on cooling: $^1$H NMR (CDCl$_3$) δ 7.39 (s, 1 H), 7.33 (m, 1H), 7.28 (t, J=7.5 Hz, 1H), 7.13 (d, J=7.5 Hz, 1H), 4.0 (m, 4H), 2.91 (hept, J=7 Hz, 1H), 2.15 (m, 4H), 1.82 (br d, J=11.5 Hz, 2H), 1.70 (brd, J=11.5 Hz, 2H), 1.25 (d, J=7 Hz, 6 H); MS (CI) m/z 259.2 (M−OH).

Step 2. Preparation of 8-(3-isopropylphenyl)-1,4-dioxa-spiro[4.5]decane-8-azide (10)

8-(3-isopropylphenyl)-1,4-dioxa-spiro[4.5]decane-8-alcohol 9 (5.5 g, 20 mmol) was reacted with sodium azide (2.9 g, 45 mmol) and trifluoroacetic acid (TFA, 13 mL, 170 mmol) in 120 mL of CH$_2$Cl$_2$ at 0° C., allowing the reaction to stir 2 h after dropwise addition of the TFA. The reaction was quenched by dropwise addition of 18 mL of concentrated NH$_4$OH.

The mixture was taken up in water, ethyl acetate, and heptane, and the organic phase was washed three more times with water and once with brine. The solution was dried (Na$_2$SO$_4$), filtered, concentrated, and chromatographed over silica gel, eluting with 3% acetone in heptane. Concentration of the product-containing fractions afforded 2.2 g (7.3 mmol, 36%) of 10 as a colorless oil: $^1$H NMR (CDCl$_3$) δ 7.33-7.26 (m, 3 H), 7.17 (m, 1 H), 3.98 (m, 4 H), 2.92 (hept, J=7 Hz, 1 H), 2.2-2.12 (m, 2 H), 2.07-1.95 (m, 4 H), 1.72 (m, 2 H), 1.26 (d, J=7 Hz, 6 H).

Step 3. Preparation of 8-(3-isopropylphenyl)-1,4-dioxa-spiro[4.5]decane-8-amine acetate (11)

2.2 g (7.3 mmol) of 8-(3-isopropylphenyl)-1,4-dioxa-spiro[4.5]decane-8-azide (10) in 200 mL of ethanol was reduced under 16 psi of hydrogen in the presence of 0.7 g of 10% palladium on carbon for 4.5 h. Filtration and removal of solvents with a toluene azeotrope affords a white solid which was triturated with pentane to yield 2.14 g (6.4 mmol, 87%) of 11 as a white solid: $^1$H NMR (CDCl$_3$) δ 7.37-7.33 (m, 2 H), 7.30-7.26 (m, 1 H), 7.13 (d, J=7.5 Hz, 1 H), 5.91 (br, 3 H), 3.96 (m, 4 H), 2.90 (hept., J=7 Hz, 1 H), 2.32 (m, 2 H), 2.03 (s, 3 H), 2.0-1.85 (m, 4 H), 1.63 (m, 2 H), 1.25 (d, J=7 Hz, 6 H); MS (CI) m/z 259.2 (M-NH$_2$).

EXAMPLE 6

Exemplary Preparation of Oxime Precursor

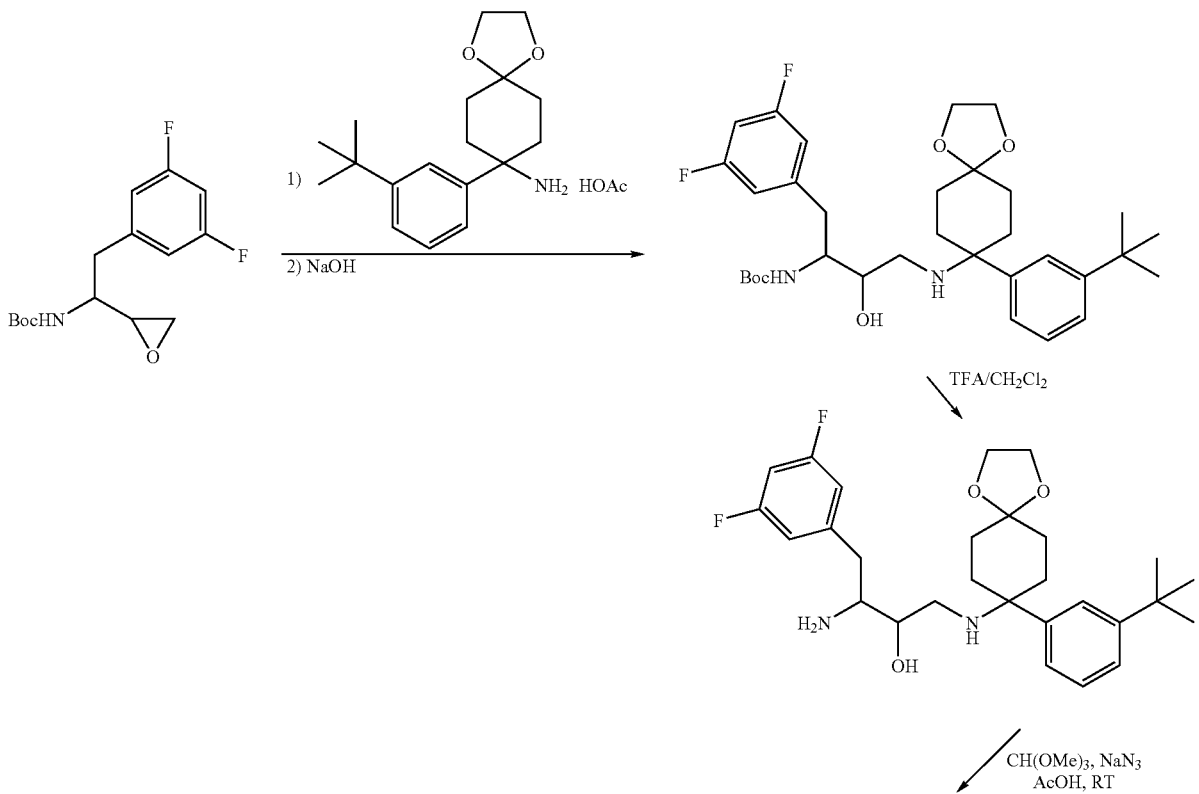

Scheme 5

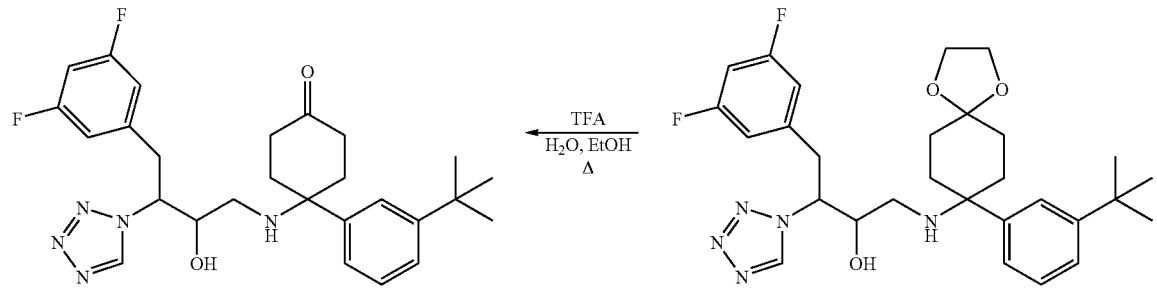
EXAMPLE 7
Exemplary Prepatation of an Oxime
EXAMPLE 8
Exemplary Preparation of a Hydrazone
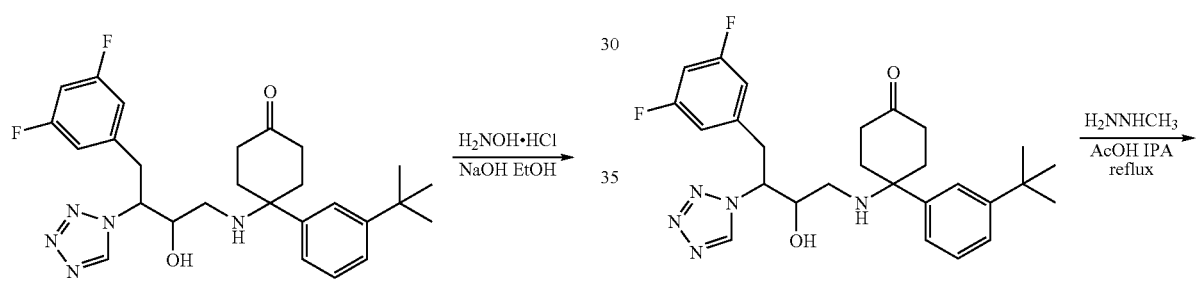
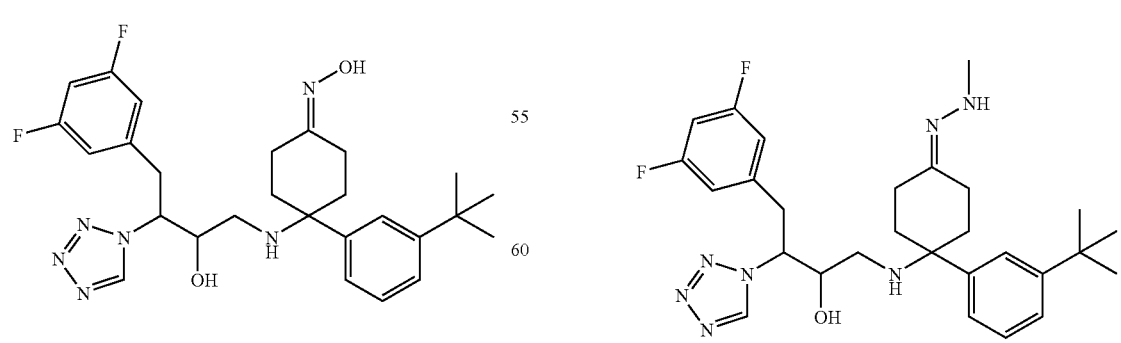

EXAMPLE 9

Preparation of N-((1S,2R)-1-(3,5-DIFLUOROBENZYL)-2-HYDROXY-3-{[1-(3-ISOPROPYLPHENYL)CYCLOHEXAN-4-ONE]AMINO}PROPYL) ACETAMIDE (15)

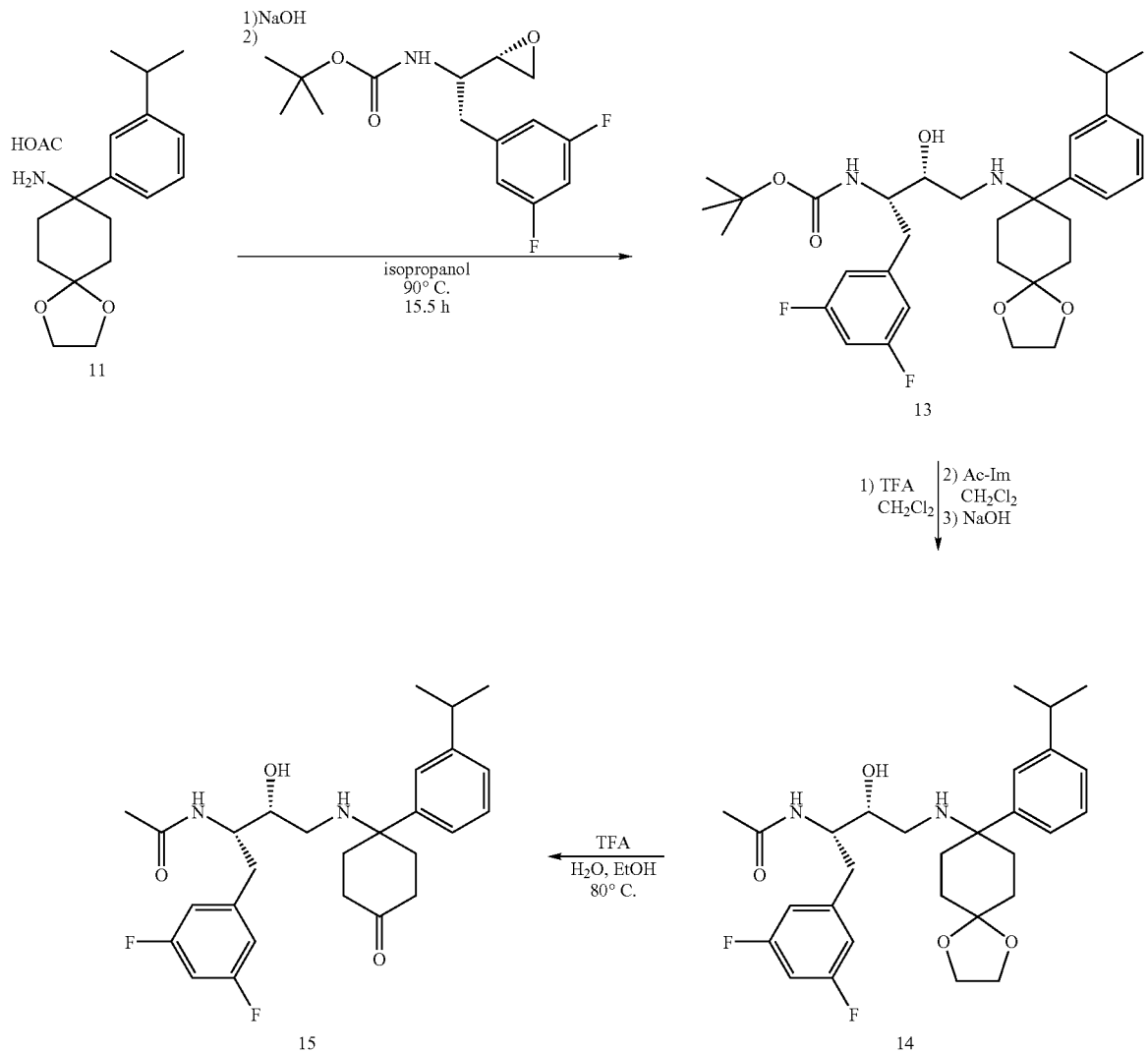

Scheme 6

Step 1. Preparation of tert-butyl (1S,2R)-1-(3,5-difluorobenzyl)-2-hydroxy-3-{8-(3-isopropylphenyl)-1,4-dioxa-spiro[4.5]decane-8-amino}propylcarbamate (13)

8-(3-isopropylphenyl)-1,4-dioxa-spiro[4.5]decane-8-amine acetate 11 (3.2 mmol) was neutralized and reacted with [2-(3,5-Difluoro-phenyl)-1-oxiranyl-ethyl]-carbamic acid tert-butyl ester 12 (0.6 g, 2.0 mmol) in refluxing isopropanol (15 mL) for 15.5 h. The reaction mixture was concentrated and chromatographed over silica gel, eluting with 4% methanol (containing 2% of NH$_4$OH) in CH$_2$Cl$_2$ to separate the crude product from excess 8-(3-isopropylphenyl)-1,4-dioxa-spiro[4.5]decane-8-amine. The crude product was then re-chromatographed over silica gel, eluting with 10% to 20% acetone in CH$_2$Cl$_2$ yielding 0.600 g (1.04 mmol, 52%) of 13 as a colorless oil: $^1$H NMR (CDCl$_3$) δ 7.27-7.20 (m, 3 H), 7.09 (d, J=7 Hz, 1 H), 6.69 (m, 2 H), 6.63 (m, 1 H), 4.64 (d, J=9 Hz, 1H), 3.95 (m, 4H), 3.72 (m, 1H), 3.28 (m, 1H), 2.88 (m, 2H), 2.69 (dd, J=8.5, 14 Hz, 1 H), 2.32 (m, 2 H), 2.15 (m, 2 H), 1.99-1.86 (m, 4 H), 1.63 (m, 2 H), 1.35 (s, 9 H), 1.24 (d, J=7 Hz, 6 H); MS (CI) m/z 575.4 (MH+)

Step 2. Preparation of N-((1S,2R)-1-(3,5-difluorobenzyl)-2-hydroxy-3-{8-(3-isopropylphenyl)-1,4-dioxa-spiro[4.5]decane-8-amino}propyl)acetamide (14)

Tert-butyl (1S,2R)-1-(3,5-difluorobenzyl)-2-hydroxy-3-{8-(3-isopropylphenyl)-1,4-dioxa-spiro[4.5]decane-8-amino}propylcarbamate 13 (0.600 g, 1.04 mmol) was deprotected, acetylated, and saponified yielding, after chromatography on silica gel, eluting with 32.5% acetone and 2.5% methanol in $CH_2Cl_2$, acetamide 14 (335 mg, 0.65 mmol, 62%) as a white solid by concentration from ethyl ether: $^1H$ NMR ($CDCl_3$) δ 7.31-7.26 (m, 3 H), 7.15 (m, 1 H), 6.69-6.61 (m, 3 H), 5.9 (br, 1 H), 4.13 (m, 1 H), 3.95 (m, 4 H), 3.48 (m, 1 H), 2.92-2.83 (m, 2 H), 2.73 (dd, J=8.5, 14 Hz, 1 H), 2.45-2.25 (m, 4 H), 2.10 (m, 2 H), 1.88 (s+m, 5 H), 1.62 (m, 2 H), 1.25 (d, J=7 Hz, 6 H); MS (CI) m/z 517.4 (MH+).

Step 3. Preparation of N-((1S,2R)-1-(3,5-difluorobenzyl)-2-hydroxy-3-{[1-(3-isopropylphenyl)cyclohexan-4-one]amino}propyl)acetamide (15)

To N-((1S,2R)-1-(3,5-difluorobenzyl)-2-hydroxy-3-{8-(3-isopropylphenyl)-1,4-dioxa-spiro[4.5]decane-8-amino}propyl)acetamide 14 (255 mg, 0.49 mmol) in 5 mL of ethanol and 5 mL of water was added 6 mL of trifluoroacetic acid, and the mixture was refluxed for 2 h under nitrogen. It was concentrated and taken up in aqueous 10% $Na_2CO_3$ and ethyl acetate. The organic phase was washed twice more with 10% $Na_2CO_3$ and then with brine. It was dried over $Na_2SO_4$, and concentrated to a colorless oil. Evaporation in vacuo from ethyl ether affords 15 (140 mg, 0.30 mmol, 60%) as a white solid: $^1H$ NMR ($CDCl_3$) δ 7.35-7.18 (m, 4 H), 6.71-6.64 (m, 3 H), 5.65 (br, 1 H), 4.12 (m, 1 H), 3.43 (m, 1 H), 2.95-2.90 (m, 2 H), 2.75 (dd, J=8.5, 14 Hz, 1 H), 2.64 (m, 2 H), 2.4-2.25 (m, 8 H), 1.87 (s, 3 H), 1.25 (d, J=7 Hz, 6 H); MS (CI) m/z 473.4 (MH+). The LC-MS spectrum in methanol solvent showed a small signal at 505.4 (MH+$CH_3OH$) due to hemiketal formation. IR (diffuse reflectance) 3311, 2958, 1710, 1646, 1628, 1595, 1550, 1544, 1460, 1372, 1315, 1116, 983, 846, 707 $cm^{-1}$.

MS (EI) m/z (relative intensity) 472 (M+, 6), 472 (6), 417 (5), 416 (33), 415 (99), 398 (8), 397 (30), 327 (11), 244 (9), 215 (13), 214 (6). HRMS (ESI) calculated for $C_{27}H_{34}N_2O_3F_2+H_1$ 473.2615, found 473.2627. Anal. Calc'd for $C_{27}H_{34}F_2N_2O_3+0.5H_2O$: C, 67.34; H, 7.33; N, 5.82. Found (av): C, 67.89; H, 7.32; N, 5.86.

EXAMPLE 10

Preparation of N-[3-[1-(3-TERT)-BUTYL-PHENYL)-4-HYDROXYIMINO-CYCLOHEXYLAMINO]-1-(3,5-DIFLUORO-BENZYL)-2-HYDROXY-PROPYL]-ACETAMIDE

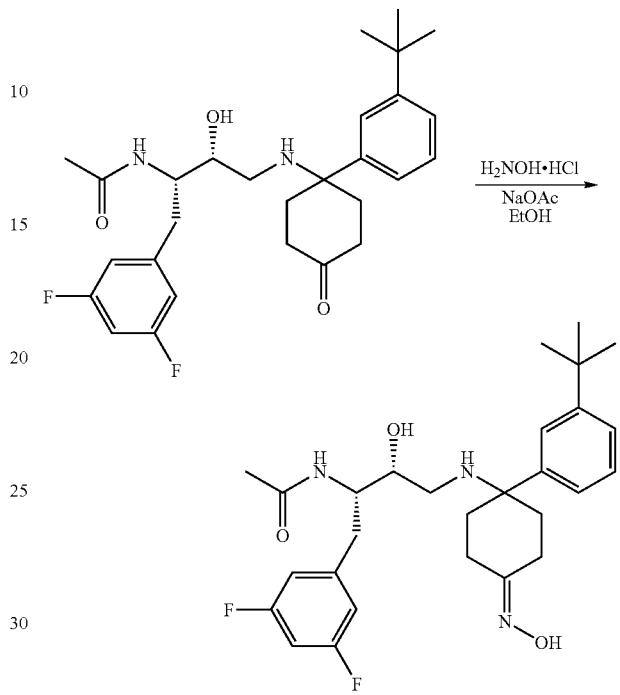

To a solution of N-[3-[1-(3-tert)-Butyl-phenyl)-4-oxo-cyclohexylamino]-1-(3,5-difluoro-benzyl)-2-hydroxy-propyl]-acetamide (0.208 g, 0.43 mmol) in ethanol (4 mL) was added hydroxylamine hydrochloride (0.074 g, 1.07 mmol) and sodium acetate (0.17 g, 2.05 mmol). The reaction mixture was stirred at room temperature for 2.5 h prior to partitioning between $H_2O$ and $CH_2Cl_2$. The organic layer was separated, dried ($Na_2SO_4$) and concentrated under reduced pressure. The residue was purified by flash chromatography (5% MeOH/$CH_2Cl_2$) to yield the desired product (0.11 g, 53%). MS (ESI): 502.2 (M+H). See Bravo, P., et al., *J. Fluorine Chem.*, 59 (1992), 153-56.

EXAMPLE 11

Preparation of N-[3-[1-(3-TERT)-BUTYL-PHENYL)-4-METHOXYIMINO-CYCLOHEXYLAMINO]-1-(3,5-DIFLUORO-BENZYL)-2-HYDROXY-PROPYL]-ACETAMIDE

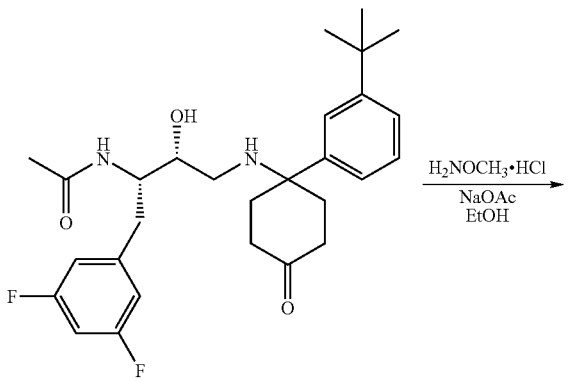

-continued

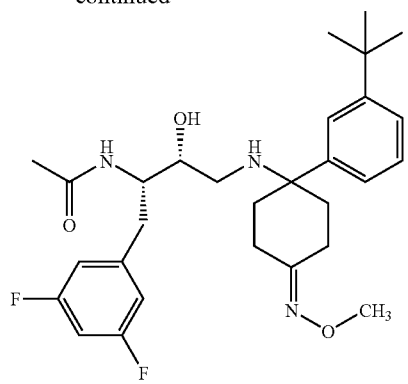

N-[3-[1-(3-tert)-Butyl-phenyl)-4-methoxyimino-cyclohexylamino]-1-(3,5-difluoro-benzyl)-2-hydroxy-propyl]-acetamide was prepared according to essentially the same procedure as described in EXAMPLE 10. MS (ESI): 516.3 (M+H).

EXAMPLE 12

N-[3-[1-(3-TERT)-BUTYL-PHENYL)-4-ETHOXY-IMINO-CYCLOHEXYLAMINO]-1-(3,5-DIF-LUORO-BENZYL)-2-HYDROXY-PROPYL]-ACETAMIDE

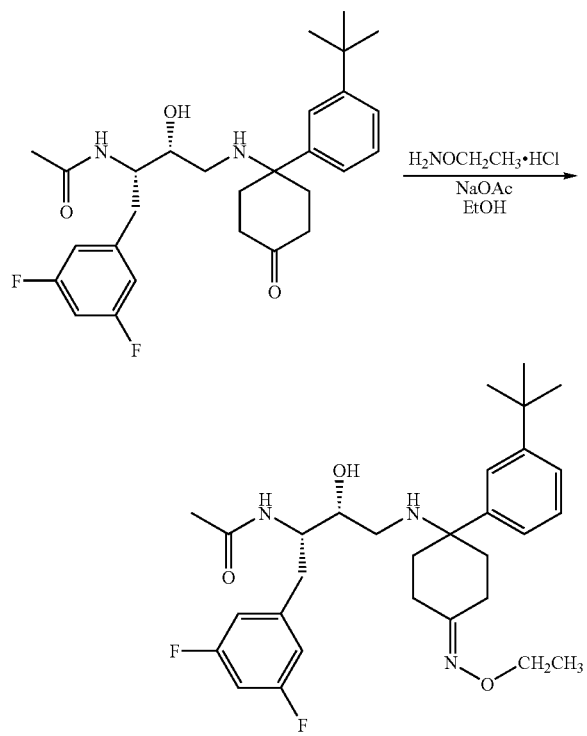

N-[3-[1-(3-tert)-Butyl-phenyl)-4-methoxyimino-cyclohexylamino]-1-(3,5-difluoro-benzyl)-2-hydroxy-propyl]-acetamide was prepared according to essentially the same procedure as described in EXAMPLE 10. MS (ESI): 530.2 (M+H).

EXAMPLE 13

2-AMINOETHANOL HYDROCHLORIDE

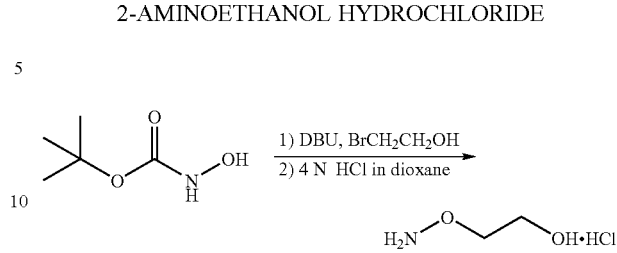

Tert-Butyl N-hydroxycarbamate (Aldrich, 2.64 g, 19.8 mmol) was dissolved in 1,8-diazabicyclo[5.4.0]undec-7-ene (3.0 mL, 20 mmol) and 2-bromoethanol (1.7 mL, 24 mmol). The reaction mixture was allowed to stir at room temperature overnight and quenched with 1N HCl. The product was extracted with $CH_2Cl_2$, dried ($Na_2SO_4$), and concentrated under reduced pressure. The residue was purified by flash chromatography (Hexane:EtOAc, 1:1) yielding the desired product (2.48 g, 71%). MS (ESI): 200.1 (M+Na).

The N-Boc intermediate was deprotected by treatment with 4 N HCl in dioxane. The reaction mixture was allowed to stir at room temperature for 2 h prior to concentration under reduced pressure. See Jones, D. S., et al., *Tet. Lett.*, 41, (2000) 1531-33.

EXAMPLE 14

N-[3-[1-(3-TERT)-BUTYL-PHENYL)-4-(2-HY-DROXY-ETHOXYIMINO-CYCLOHEXY-LAMINO]-1-(3,5-DIFLUORO-BENZYL)-2-HY-DROXY-PROPYL]-ACETAMIDE

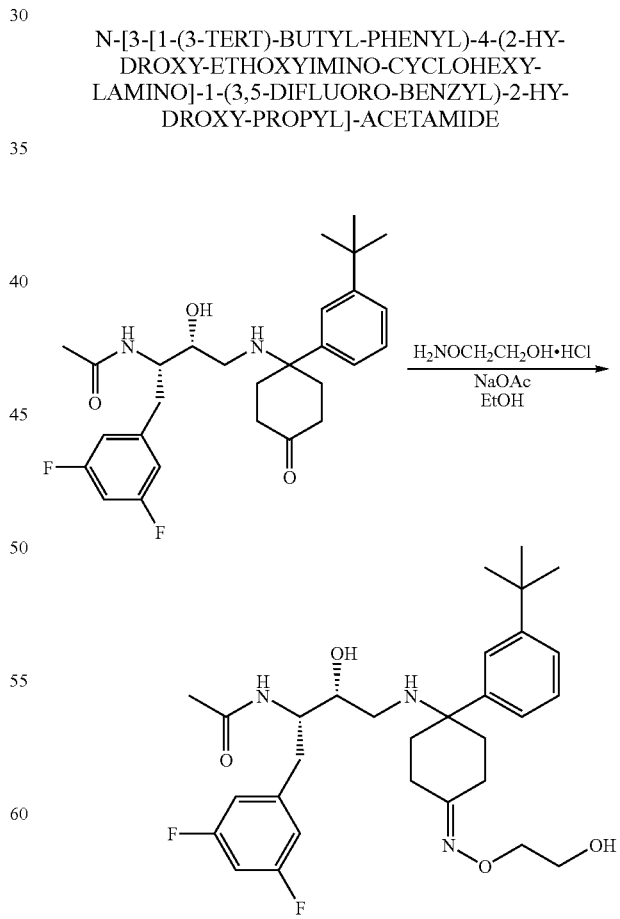

N-[3-[1-(3-tert)-Butyl-phenyl)-4-methoxyimino-cyclohexylamino]-1-(3,5-difluoro-benzyl)-2-hydroxy-propyl]- acetamide was prepared according to essentially the same procedure as described in EXAMPLE 10. MS (ESI): 546.3 (M+H). See Jones, D. S., et al., *Tet. Lett.*, 41, (2000) 1531-33.

EXAMPLE 15

Preparation of N-{1-(3,5-DIFLUORO-BENZYL)-2-HYDROXY-3-[4-METHOXYIMINO-1-(3-R—PHENYL)-CYCLOHEXYLAMINO]-PROPYL}-ACETAMIDE

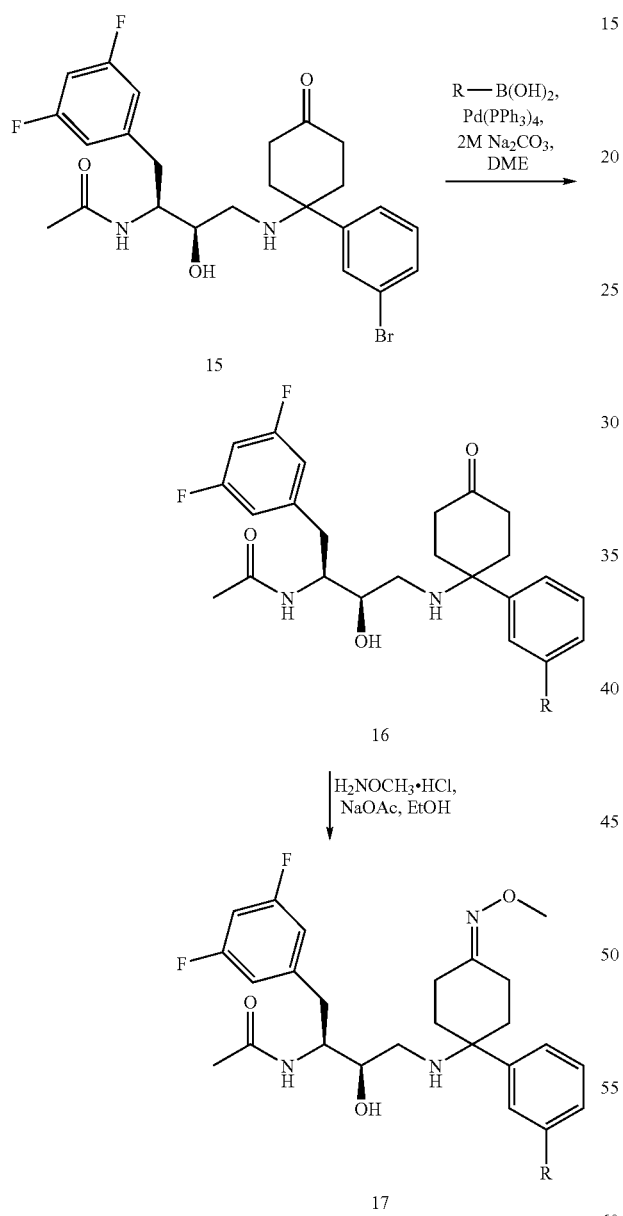

25 mg (0.04 mmol) of the N-[3-[1-(3-Bromo-phenyl)-4-oxo-cyclohexylamino]-1-(3,5-difluoro-benzyl)-2-hydroxy-propyl]-acetamide 15 was dissolved in 1 mL DME and placed in a 4 mL reaction vial. Under N₂(g), a solution of the boronic acid (0.06 mmol), tetrakis(triphenylphosphine) palladium(0) (0.006 mmol), and 0.125 mL of aqueous 2M Na₂CO₃ dissolved in 1 mL DME was added to the reaction mixture. The reaction was then stirred at 95° C. for 15 h. The reaction mixture was then concentrated yielding product 16.

The product 16 (0.048 mmol) was then dissolved in 1 mL ethanol and placed in a 4 mL reaction vial. Methoxylamine hydrochloride (0.23 mmol) and sodium acetate (0.13 mmol) are added in the vial. The reaction was then stirred for 2.5 h at room temperature. The reaction mixture was then concentrated and the product 17 was isolated via preparative HPLC: Method [1].

EXAMPLE 16

Procedure of N-[3-[1-(3-BROMO-PHENYL)-4-OXO-CYCLOHEXYLAMINO]-1-(3,5-DIFLUORO-BENZYL)-2-HYDROXY-PROPYL]-ACETAMIDE (19)

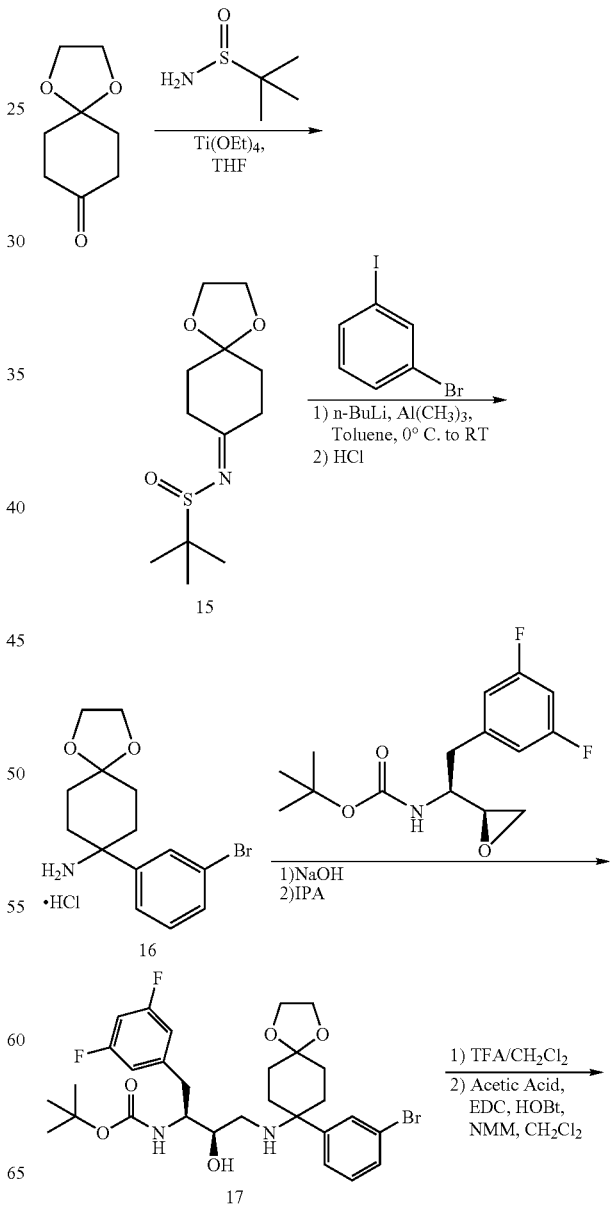

-continued

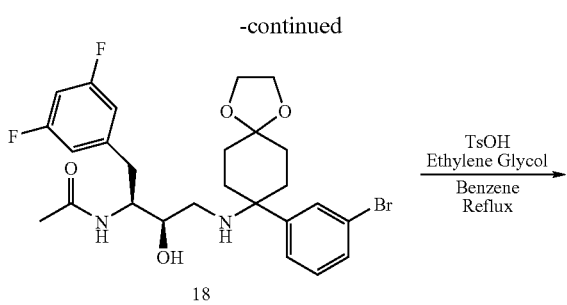

18

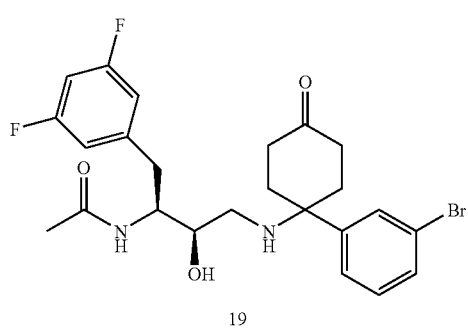

19

Step 1: Procedure of 2-Methyl-propane-2-sulfinic acid (1,4-dioxa-spiro[4.5]dec-8-ylidene)-amide (15)

An oven dried round-bottom flask was cooled to room temperature by flushing with $N_2(g)$ for 30 min. 1,4-Dioxa-spiro[4.5]decan-8-one (1.35 g, 8.66 mmol) (dissolved in 12 mL THF), 2-Methyl-propane-2-sulfinic acid amide (1.0 g, 8.25 mmol) (dissolved in THF), and titanium(IV) ethoxide (3.77 g, 16.50 mmol) were added. The reaction was stirred for 4 h at room temperature. To the mixture was added 15 mL saturated $NaHCO_3$ followed by filtration and an EtOAc rinse. The organic layer was dried with $MgSO_4$, filtered and concentrated under reduced pressure yielding 0.98 g of Compound 15.

MS m/z 260.1; retention time: 0.754, method [8].

Step 2: Procedure for 8-(3-Bromo-phenyl)-1,4-dioxa-spiro[4.5]dec-8-ylamine Hydrochloride (16)

Two oven dried round-bottom flask were cooled to room temperature by flushing with $N_2(g)$. n-Butyl Lithium (2.5 M in hexanes) (0.46 g, 7.14 mmol) was added dropwise to a stirring solution of 1-Bromo-3-iodo-benzene (2.02 g, 7.14 mmol) in 3.2 mL toluene at 0° C. The reaction stirred from 0° C. to room temperature over 2 h. A separate solution of compound 15 (0.98 g, 3.4 mmol) and $AlMe_3$ (0.269 g, 3.74 mmol) were added to a second flask cooled to −78° C. and stirred for 10 min. This second mixture was added by cannula to the first. The combined material was at 0° C. and allowed to reach room temperature over 3 h. The reaction was then quenched with $Na_2SO_4.6H_2O$. $MgSO_4$ was added to the reaction mixture, which was then filtered and concentrated under reduced pressure. The reaction provided 1.6 g of crude material. A column on silica gel (50% EtOAc: hexanes) provided 0.29 g of pure material. The pure material was treated with 0.69 mL 4M HCl in dioxanes and stirred for 1 h at room temperature. The reaction mixture was then placed under reduced pressure. 0.23 g of Compound 16 were recovered.

MS m/z 295.0 (M-NH$_2$); retention time: 0.979, method [8].

Step 3: Procedure for [3-[8-(3-Bromo-phenyl)-1,4-dioxa-spiro[4.5]dec-8-ylamino]-1-(3,5-difluoro-benzyl)-2-hydroxy-propyl]-carbamic acid tert-butyl ester (17)

Compound 16 was dissolved in 1 mL MeOH and added to a round bottom flask. 2M NaOH was added until the pH was approximately 10. The reaction mixture was rinsed six times with $CH_2Cl_2$. The organic layer was dried with $MgSO_4$, filtered and concentrated under reduced pressure to get 0.16 grams of product. The product was then dissolved in 1.0 mL isopropyl alcohol and added to a sealed tube containing [2-(3,5-Difluoro-phenyl)-1-oxiranyl-ethyl]-carbamic acid tert-butyl ester (0.72 mmol). The reaction was heated to 80° C. over night. The reaction was concentrated by reduced pressure yielding Compound 17.

MS m/z 611.1; retention time: 1.919, method [7].

Step 4: Procedure for N-[3-[8-(3-Bromo-phenyl)-1,4-dioxa-spiro[4.5]dec-8-ylamino]-1-(3,5-difluoro-benzyl)-2-hydroxy-propyl]-acetamide (18)

Compound 17 was dissolved in 1 mL (1:1) trifluoroacetic acid (TFA) and $CH_2Cl_2$. The reaction stirred at room temperature for 2 h and concentrated under reduced pressure. The residue was dissolved in 4 mL $CH_2Cl_2$ and N-Methyl-morpholine (NMM) (3.12 mmol). The reaction was stirred at 0° C. Acetic Acid (0.76 mmol) was added slowly to the reaction mixture and the mixture stirred at 0° C. for five min. Then 1-Hydroxylbenzotriazole hydrate (HOBt) (0.76 mmol) and 1-Ethyl-3-(3'-Dimethylaminopropyl)carbodiimide Hydrochloride (EDC.HCl) (0.76 mmol) were added sequentially. The reaction was stirred at room temperature for two h. $CH_2Cl_2$ was removed by reduced pressure and the residue dissolved in EtOAc. The organic layer was rinsed with a saturated $NaHCO_3$ solution three times and once with Brine. The organic layer was dried with $MgSO_4$, filtered and concentrated under reduced pressure. Compound 22 was purified by preparative HPLC.

MS m/z 509.0; retention time: 1.335, method [7].

Step 5: Procedure for N-[3-[1-(3-Bromo-phenyl)-4-oxo-cyclohexylamino]-1-(3,5-difluoro-benzyl)-2-hydroxy-propyl]-acetamide (19)

Compound 18 (0.4 g, 0.78 mmol), p-Toluenesulfonic acid monohydrate (TsOH) (0.16 g, 0.84 mmol), and poly(Ethylene glycol) (8.9 g, 143.4 mmol) were added to 25 mL benzene. The reaction was heated to 100° C. for 30 min. The benzene was removed under reduced pressure and fresh benzene was added. The resulting mixture was treated with saturated $NaHCO_3$ and extracted $CH_2Cl_2$. The organic layer was washed with brine and dried with $MgSO_4$, filtered and concentrated under reduced pressure providing 0.4 g of Compound 19.

MS m/z 553.1; retention time: 1.523, method [7].

EXAMPLE 17

N-{1-(3,5-DIFLUORO-BENZYL)-2-HYDROXY-3-[8-(3-PYRAZOL-1-YL-PHENYL)-1,4-DIOXA-SPIRO[4.5]DEC-8-YLAMINO]-PROPYL}-ACETAMIDE (21)

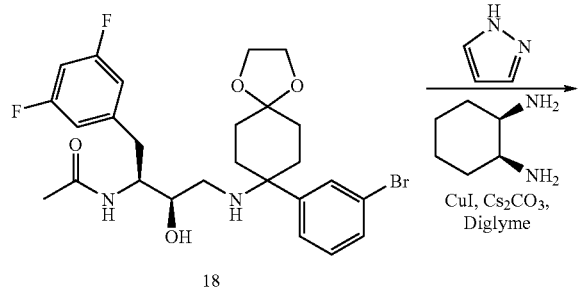

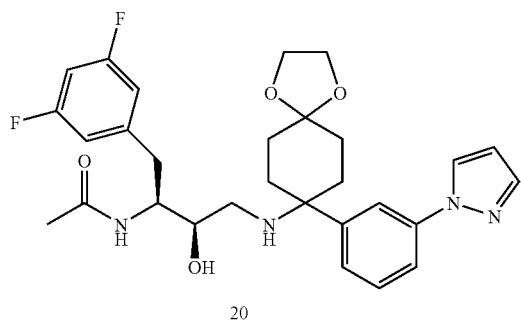

Compound 18 (0.4 g, 0.72 mmol), pyrazole (0.059 g, 0.87 mmol), and cesium carbonate (0.47 g, 1.45 mmol) were added to a round-bottom flask. Diglyme was added to trans-1,2-diaminocyclohexane (0.0082 g, 0.072 mmol). This mixture was added to Copper(I) Iodide (0.014 g, 0.072 mmol). The mixture was then added to the round-bottom flask. The reaction mixture was then heated to 130° C. for 4 days. The crude material was purified by preparative HPLC (13.0 mg) yielding Compound 20.

$^1$H NMR (CD$_3$OD) δ 7.87 (s, 1H), 7.72-7.65 (m, 2H), 7.52-7.46 (m, 1H), 6.82-6.79 (m, 3H), 4.00-3.87 (m, 4H), 3.57-3.54 (m, 1H), 3.23-3.17 (m, 1H), 2.83-2.65 (m, 3H), 2.58-2.53 (m, 1H), 2.27-2.19 (m, 2H), 1.87 (s, 2H), 1.80 (s, 2H), 1.80 (s, 3H), 1.51-1.29 (m, 4H).

MS m/z 541.2; retention time: 1.412, method [7].

EXAMPLE 18

N-{1-(3,5-DIFLUORO-BENZYL)-2-HYDROXY-3-[4-METHOXYIMINO-1-(3-PYRAZOL-1-YL-PHENYL)-CYCLOHEXYLAMINO]-PROPYL}-ACETAMIDE (21)

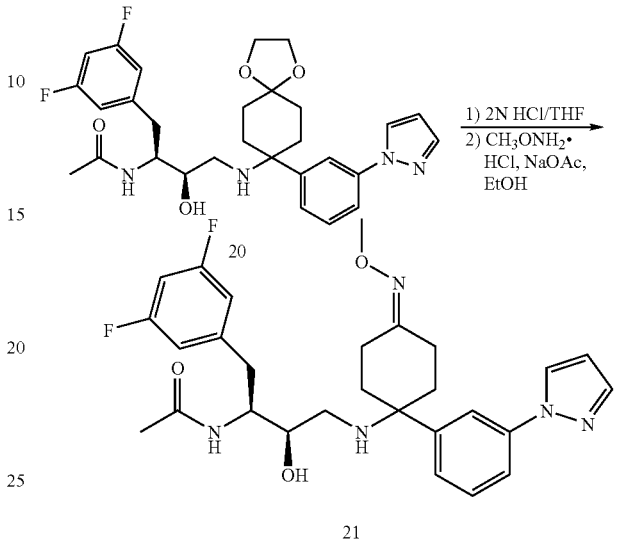

Compound 20 was treated with a (1:1) 2M HCl and THF solution (10 mL) and refluxed overnight. Almost all the THF was removed under reduced pressure and 10% NaOH was added until the pH was approximately 10. The reaction mixture was then rinsed six times with CH$_2$Cl$_2$. The organic layer was rinsed with MgSO$_4$, filtered and concentrated under reduced pressure to provide 0.044 g of about 85% pure product. The ketone was then transferred to a round-bottom flask containing CH$_3$ONH$_2$.HCl (0.013 g, 0.20 mmol), NaOAc (0.032 g, 0.39 mmol), and 5 mL EtOH. The reaction stirred at room temperature for 2.5 h. The reaction was quenched with H$_2$O and extracted with CH$_2$Cl$_2$. The CH$_2$Cl$_2$ was removed under reduced pressure and the crude material was purified by preparative HPLC (9.0 mg) yielding Compound 21.

$^1$H NMR (CD$_3$OD) δ 8.35-8.34 (bs, 1H), 8.12 (s, 1H), 7.91-7.88 (d, J=9 Hz, 1H), 7.77 (s, 1H), 7.72-7.63 (m, 2H), 6.79-6.73 (m, 3H), 6.58-6.57 (m, 1H), 3.86-3.83 (m, 1H), 3.77 (s, 3H), 3.58-3.54 (m, 1H), 3.23-3.15 (m, 2H), 2.93-2.89 (m, 2H), 2.76-2.73 (bs, 2H), 2.57-2.48 (m, 2H), 2.21-2.17 (m, 2H), 2.13-2.03 (m, 2H), 1.71 (s, 3H).

MS m/z 526.2; retention time: 1.464, method [7].

EXAMPLE 19

N-[3-[1-(3-TERT-BUTYL-PHENYL)-3-METHYL-ENE-CYCLOHEXYLAMINO]-1-(3,5-DIFLUORO-BENZYL)-2-HYDROXY-PROPYL]-ACETAMIDE

Step 1

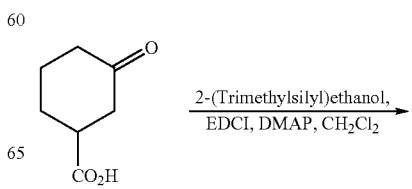

-continued

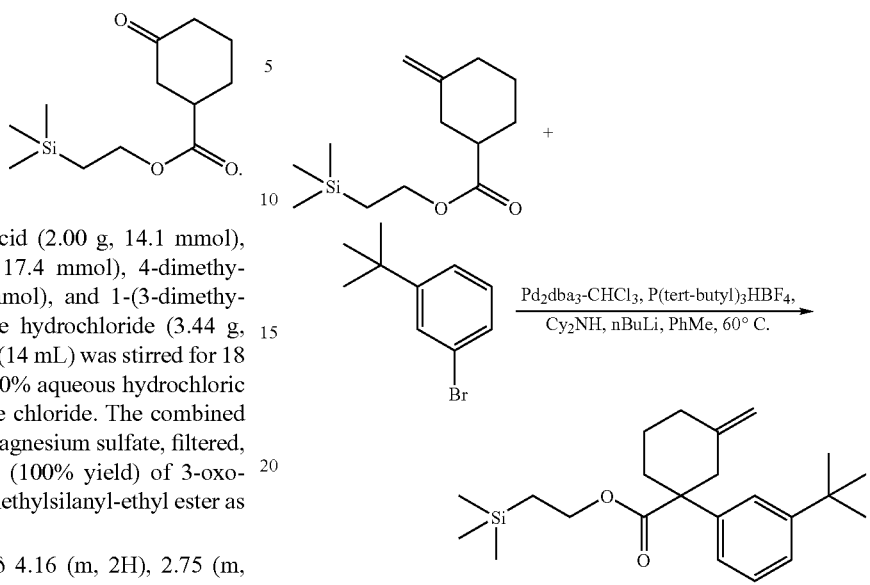

3-oxo-cyclohexanecarboxylic acid (2.00 g, 14.1 mmol), 2-trimethylsilylethanol (2.5 mL, 17.4 mmol), 4-dimethylaminopyridine (148 mg, 1.21 mmol), and 1-(3-dimethylaminopropyl)-3-ethylcarbodiimide hydrochloride (3.44 g, 17.9 mmol) in methylene chloride (14 mL) was stirred for 18 h. The solution was diluted with 10% aqueous hydrochloric acid and extracted with methylene chloride. The combined organic extracts were dried over magnesium sulfate, filtered, and concentrated to yield 3.41 g (100% yield) of 3-oxo-cyclohexanecarboxylic acid 2-trimethylsilanyl-ethyl ester as a clear oil.

$^1$H NMR (300 MHz, CDCl$_3$) δ 4.16 (m, 2H), 2.75 (m, 1H), 2.55 (d, J=7.9 Hz, 2H), 2.36 (m, 2H), 2.08 (m, 2H), 1.82 (m, 2H), 0.98 (m, 2H), 0.04 (s, 9H).

Step 2

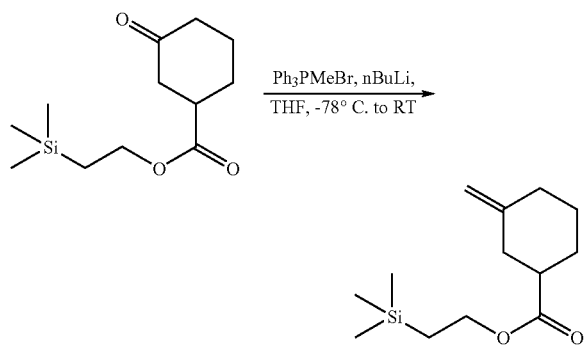

A solution of 1.6 M n-butyllithium in hexanes (14.0 mL, 22.4 mmol) was added to a heterogeneous mixture of methyltriphenylphosphonium bromide (8.02 g, 22.4 mmol) in tetrahydrofuran (50 mL) at −10° C. After stirring for 30 min at −10° C., the yellow slurry was cooled to −78° C. and 3-oxo-cyclohexanecarboxylic acid 2-trimethylsilanyl-ethyl ester (3.41 mg, 14.1 mmol) in tetrahydrofuran (20 mL) was added. After stirring for 10 min at −78° C., the dry ice/acetone bath was removed and the heterogeneous mixture was stirred for 3 h, during which time the solution warmed to ambient temperature. The heterogeneous mixture was concentrated and the residue was flash chromatographed with 99:1, 49:1, 24:1, and 23:2 hexanes:etheyl acetate as the eluant to yield 3.38 g (100% yield) of 3-methylene-cyclohexanecarboxylic acid 2-trimethylsilanyl-ethyl ester as a clear oil.

$^1$H NMR (300 MHz, CDCl$_3$) δ 4.68 (s, 2H), 4.16 (m, 2H), 2.51 (m, 1H), 2.24 (broad m, 3H), 1.98 (m, 2H), 1.86 (m, 1H), 1.55 (m, 1H), 1.38 (m, 1H), 0.98 (m, 2H), 0.05 (s, 9H).

Step 3

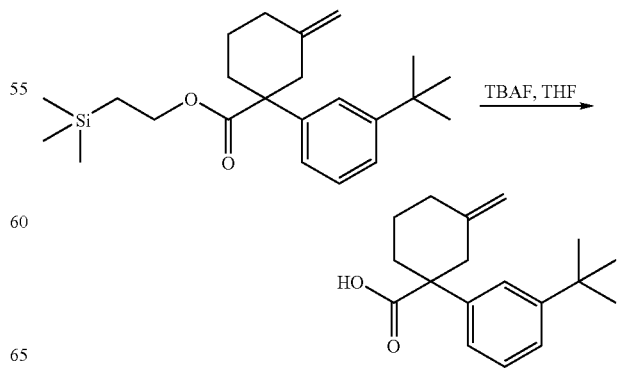

A 1.6 M solution of n-butyllithium (12.0 mL, 19.2 mmol) was added to a solution of dicyclohexylamine (3.7 mL, 18.6 mmol) in toluene (40 mL). After stirring for 5 min, 3-methylene-cyclohexanecarboxylic acid 2-trimethylsilanyl-ethyl ester (3.45 g, 14.4 mmol) was added. After stirring for 30 min, 1-bromo-3-tert-butyl-benzene (3.16 g, 14.8 mmol) was added followed by the simultaneous addition of tri-tert-butylphosphonium tetrafluoroborate (220 mg, 758 mmol) and tris(dibenzylideneacetone)dipalladium(0)-chloroform adduct (380 mg, 367 mmol). The solution was placed into a preheated oil bath at 60° C. After stirring for 16 h, the solution was directly flash chromatographed with 99:1, 49:1, 24:1, and 23:2 hexanes:ethyl acetate as the eluant to yield 4.31 g (81% yield) of 1-(3-tert-butyl-phenyl)-3-methylene-cyclohexanecarboxylic acid 2-trimethylsilanyl-ethyl ester as a light yellow oil.

$^1$H NMR (300 MHz, CDCl$_3$) δ 7.43 (d, J=1.0 Hz, 1H), 7.25 (m, 3H), 4.82 (s, 1H), 4.78 (s, 1H), 4.12 (m, 2H), 3.06 (d, J=13.3 Hz, 1H), 2.52 (d, J=13.3 Hz, 2H), 2.26 (dt, J=13.1 Hz and 4.5 Hz, 1H), 2.05 (m, 1H), 1.88-1.59 (broad m, 3H), 1.31 (s, 9H), 0.89 (m, 2H), −0.04 (s, 9H).

Step 4

A 1.0 M solution of tetrabutylammonium fluoride in tetrahydrofuran (15.0 mL, 15.0 mmol) was added to 1-(3-tert-butyl-phenyl)-3-methylene-cyclohexanecarboxylic acid 2-trimethylsilanyl-ethyl ester (2.67 mg, 7.16 mmol). After stirring for 16 h, the solution was concentrated, diluted with 10% aqueous hydrochloric acid, and extracted with diethyl ether. The combined organic extracts were dried over magnesium sulfate, filtered, and concentrated to yield 2.09 g (100% yield) of 1-(3-tert-butyl-phenyl)-3-methylene-cyclohexanecarboxylic acid as a yellow oil.

$^1$H NMR (300 MHz, CDCl$_3$) δ 7.50 (m, 1H), 7.29 (m, 3H), 4.84 (s, 1H), 4.79 (s, 1H), 3.06 (d, J=13.3 Hz, 1H), 2.58 (d, J=13.3 Hz, 1H), 2.51-1.20 (broad m, 6H), 1.34 (s, 9H).

Step 5

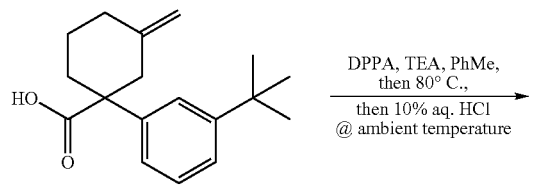

Diphenylphosphoryl azide (0.53 mL, 2.46 mmol) was added to a solution of 1-(3-tert-butyl-phenyl)-3-methylene-cyclohexanecarboxylic acid (554 mg, 2.03 mmol) and triethylamine (0.43 mL, 3.08 mmol) in toluene (4 mL). After stirring at ambient temperature for 18 h, the solution was placed into a preheated oil bath at 80° C. Bubbling was observed. After stirring for 1 h at 80° C., the bubbling had ceased and the solution was cooled to ambient temperature. 10% aqueous hydrochloric acid was added and stirred vigorously for 3 h. The aqueous layer was made alkaline with aqueous 3 N NaOH and extracted with methylene chloride. The combined organic extracts were dried over magnesium sulfate, filtered, and concentrated. The residue was flash chromatographed with 99:1:0.1, 49:1:0.1, 24:1:0.1, and 23:2:0.2 methylene chloride:methanol:concentrated ammonium hydroxide as the eluant to yield 12 mg (2% yield) of 1-(3-tert-butyl-phenyl)-3-methylene-cyclohexylamine.

Method [1] Retention time 1.94 min by HPLC and 2.00 min by MS (M−NH$_2$=227).

Step 6

Using 1-(3-tert-butyl-phenyl)-3-methylene-cyclohexylamine, [3-[1-(3-tert-Butyl-phenyl)-3-methylene-cyclohexylamino]-1-(3,5-difluoro-benzyl)-2-hydroxy-propyl]-carbamic acid tert-butyl ester, 3-Amino-1-[1-(3-tert-butyl-phenyl)-3-methylene-cyclohexylamino]-4-(3,5-difluoro-phenyl)-butan-2-ol, and N-[3-[1-(3-tert-Butyl-phenyl)-3-methylene-cyclohexylamino]-1-(3,5-difluoro-benzyl)-2-hydroxy-propyl]-acetamide are prepared according to essentially the same procedure as described in Example 9, steps 1 and 2.

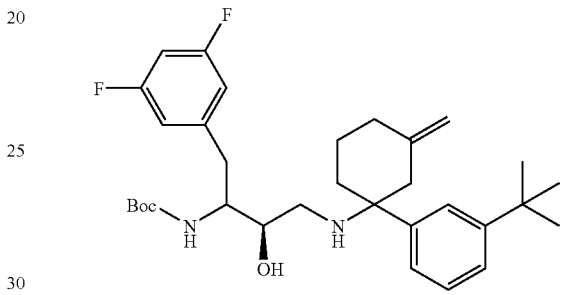

Method [1] Retention time 2.27 min by HPLC and 2.33 min by MS (M+=543).

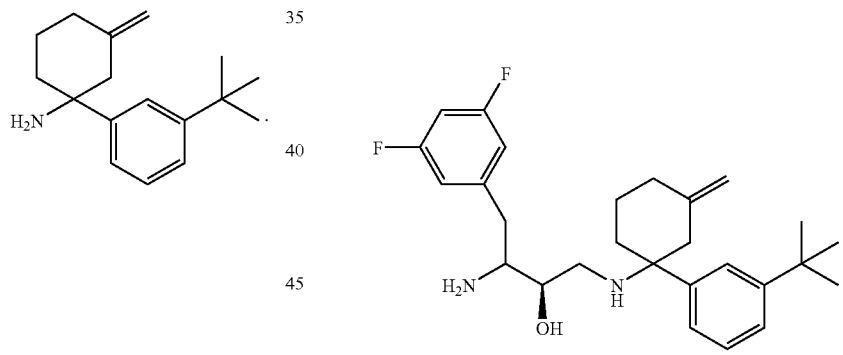

Method [1] Retention time 1.65 min by HPLC and 1.70 min by MS (M+=443).

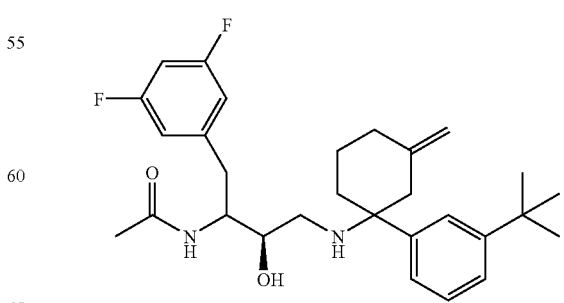

Method [1] Retention time 1.92 min by HPLC and 1.98 min by MS (M+=485).

EXAMPLE 20

N-[3-[1-(3-TERT-BUTYL-PHENYL)-4-METHYL-ENE-CYCLOHEXYLAMINO]-1-(3,5-DIFLUORO-BENZYL)-2-HYDROXY-PROPYL]-ACETAMIDE

Step 1

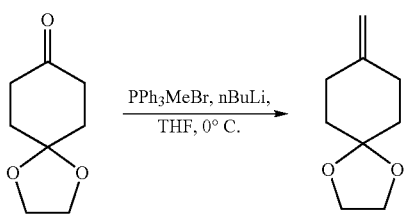

A solution of 1.6 M n-butyllithium in hexanes (46 mL, 73.6 mmol) was slowly added to a heterogeneous mixture of methyltriphenylphosphonium bromide (28.07 g, 78.6 mmol) in tetrahydrofuran (150 mL) at −10° C. After stirring for 1 h, 1,4-dioxa-spiro[4.5]decan-8-one (8.01 g, 51.3 mmol) was added. After stirring for 3 h, during which time the solution warmed to ambient temperature, acetone was added and the heterogeneous mixture was concentrated. The residue was diluted with 1:1 methylene chloride:ethyl ether, filtered and concentrated. The residue was flash chromatographed with 49:1, 24:1, and 23:2 hexanes:etheyl acetate as the eluant to yield 6.22 g (79% yield) of 8-methylene-1,4-dioxa-spiro[4.5]decane as a yellow oil.

$^1$H NMR (300 MHz, CDCl$_3$) δ 4.67 (s, 2H), 3.96 (s, 4H), 2.29 (m, 4H), 1.70 (m, 4H).

Step 2

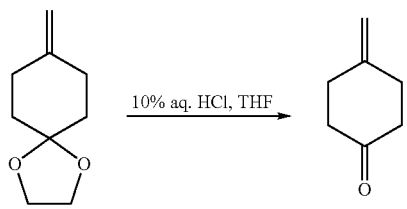

A solution of 8-methylene-1,4-dioxa-spiro[4.5]decane (6.22 g, 40.3 mmol) was stirred in tetrahydrofuran (100 mL) and 10% aqueous hydrochloric acid (100 mL) for 18 h. The solution was extracted with ethyl ether and the combined organic extracts were dried over magnesium sulfate. The combined organic extracts were filtered and concentrated to yield 3.89 g (88% yield) of 4-methylene-cyclohexanone as a yellow oil.

$^1$H NMR (300 MHz, CDCl$_3$) δ 4.89 (s, 2H), 2.47 (m, 8H).

Step 3

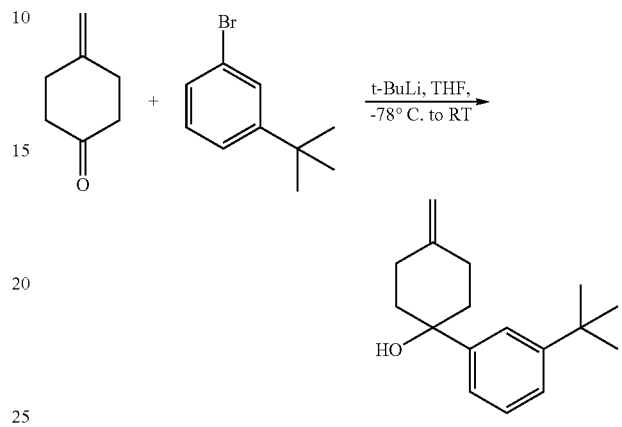

A solution of 1.7 M tert-butyllithium in pentane (32.0 mL, 54.4 mmol) was added to a solution of 1-bromo-3-tert-butyl-benzene (5.54 g, 26.0 mmol) in tetrahydrofuran (60 mL) at −78° C. After stirring for 1 h, cyclohexanone (2.00 g, 18.2 mmol) in tetrahydrofuran (15 mL) was added. After stirring for 18 h, during which time the solution warmed to ambient temperature, the solution was diluted with saturated aqueous ammonium chloride and extracted with methylene chloride. The combined organic extracts were dried over magnesium sulfate, filtered, and concentrated. The residue was flash chromatographed with 49:1, 24:1, 23:2 hexanes:ethyl acetate as the eluant to yield 3.61 g (81% yield) of 1-(3-tert-butyl-phenyl)-4-methylene-cyclohexanol as a yellow oil.

$^1$H NMR (300 MHz, CDCl$_3$) δ 7.56 (s, 1H), 7.30 (m, 3H), 4.72 (s, 2H), 2.60 (m, 2H), 2.27 (m, 2H), 1.93 (m, 4H), 1.33 (s, 9H).

Step 4

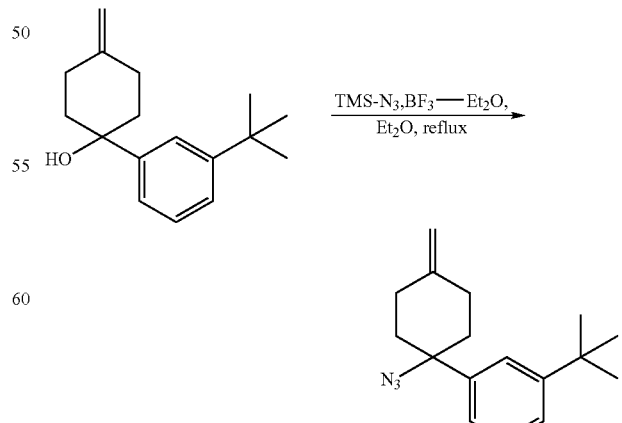

Borontrifluoride-etherate (2.0 mL, 15.7 mmol) was added to a solution of 1-(3-tert-butyl-phenyl)-4-methylene-cyclohexanol (3.60 g, 14.7 mmol) and azidotrimethylsilane (4.0 mL, 30.1 mmol) in diethyl ether (30 mL) and placed into a preheated oil bath at 45° C. After heating at reflux for 4 h, the solution was diluted with saturated aqueous ammonium chloride and extracted with diethyl ether. The combined organic extracts were dried over magnesium sulfate, filtered, and concentrated. The residue was flash chromatographed with 99:1, 49:1, and 24:1 hexanes:ethyl acetate as the eluant to yield 1.46 g (37% yield) of 1-(1-azido-4-methylene-cyclohexyl)-3-tert-butyl-benzene as a clear oil.

$^1$H NMR (300 MHz, CDCl$_3$) δ 7.47 (s, 1H), 7.36-7.23 (broad m, 3H), 4.72 (s, 2H), 2.48 (m, 2H), 2.28 (m, 2H), 2.13 (m, 2H), 1.96 (m, 2H), 1.34 (s, 9H).

Step 5

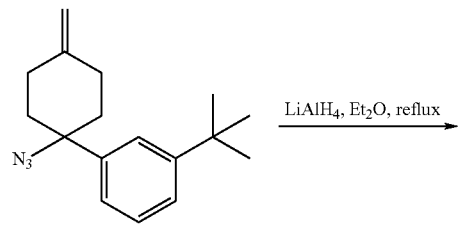

A solution of 1-(1-azido-4-methylene-cyclohexyl)-3-tert-butyl-benzene (820 mg, 3.04 mmol) in diethyl ether (10 mL) was added to a heterogeneous mixture of lithium aluminum hydride (510 mg, 13.4 mmol) in diethyl ether (10 mL) and was placed into a preheated oil bath at 40° C. After heating at reflux for 24 h, the solution was cooled to ambient temperature, and celite and sodium sulfate decahydrate was added. After stirring for 1 h, the heterogeneous mixture was filtered through celite to yield 1-(3-tert-butyl-phenyl)-4-methylene-cyclohexylamine.

Method [1] Retention time 1.62 min by HPLC and 1.67 min by MS (M+=244).

Step 6

Using 1-(3-tert-butyl-phenyl)-4-methylene-cyclohexylamine, [3-[1-(3-tert-Butyl-phenyl)-4-methylene-cyclohexylamino]-1-(3,5-difluoro-benzyl)-2-hydroxy-propyl]-carbamic acid tert-butyl ester 29, 3-Amino-1-[1-(3-tert-butyl-phenyl)-4-methylene-cyclohexylamino]-4-(3,5-difluoro-phenyl)-butan-2-ol 30, and N-[3-[1-(3-tert-Butyl-phenyl)-4-methylene-cyclohexylamino]-1-(3,5-difluoro-benzyl)-2-hydroxy-propyl]-acetamide 31 are prepared according to essentially the same procedure as described in Example 9, steps 1 and 2.

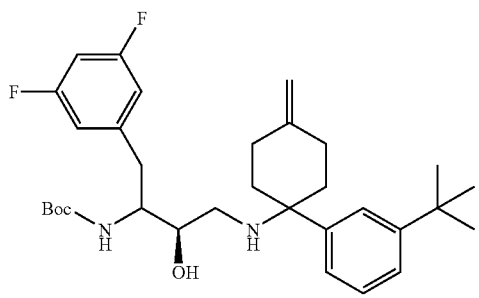

Method [1] Retention time 2.40 min by HPLC and 2.47 min by MS (M+=543).

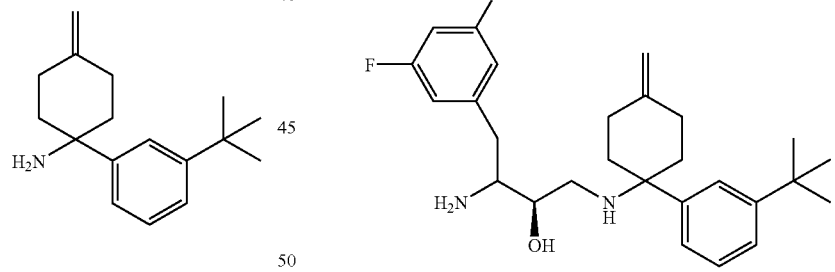

Method [1] Retention time 1.36 min by HPLC and 1.42 min by MS (M+=443).

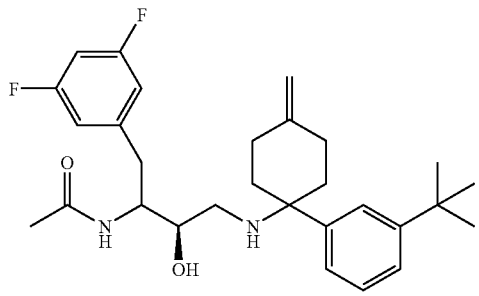

¹H NMR (300 MHz, CDCl₃) δ 9.10 (broad d, 1H), 8.10 (broad d, 1H), 7.61 (s, 1H), 7.40 (broad m, 3H), 6.64 (broad s, 3H), 6.50 (m, 1H), 6.00 (broad s, 3H), 4.72 (s, 1H), 3.98 (broad s, 1H), 3.77 (broad s, 1H), 2.93 (m, 1H), 2.68 (m, 4H), 2.37 (m, 3H), 2.09 (m, 3H), 1.83 (s, 3H), 1.32 (s, 9H). Method [1] Retention time 2.04 min by HPLC and 2.11 min by MS (M+=485).

EXAMPLE 21

Preparation of [4-[3-ACETYLAMINO-4-(3,5-DIFLUORO-PHENYL)-2-HYDROXY-BUTYLAMINO]-4-(3-TERT-BUTYL-PHENYL)-CYCLOHEXYLIDENE]-ACETIC ACID METHYL ESTER AND OF [4-[3-ACETYLAMINO-4-(3,5-DIFLUORO-PHENYL)-2-HYDROXY-BUTYLAMINO]-4-(3-TERT-BUTYL-PHENYL)-CYCLOHEXYLIDENE]-ACETIC ACID ETHYL ESTER g, 0.598 mmol) in anhydrous THF (1 mL) was added to the reaction flask. The mixture was allowed to stir for 2 days. The reaction was quenched with H₂O and extracted with CH₂Cl₂. The organic layer was collected, dried over anhydrous Na₂SO₄, filtered and concentrated. The crude product was purified by flash chromatography, eluting with 5% CH₃OH in CH₂Cl₂ yielding 0.085 g of the conjugated products. HPLC purification afforded the methyl ester: retention time (min)=1.87, method [1]; ¹H NMR (300 MHz, CD₃OD): δ 7.56 (s, 1H), δ 7.31-7.26 (m, 1H), δ 7.24-7.26 (m, 2H), δ 6.70 (d, J=7 Hz, 3H), δ 3.80-3.78 (m, 1H), δ 3.70 (s, 3H), δ 3.36-3.33 (m, 1H), δ 2.83-2.77 (m, 3H), δ2.51 (t, 1H), δ 2.30 (d, J=4 Hz, 1H), δ 2.24 (d, J=10 Hz, 1H), δ 2.16-2.07 (m, 1H), δ 1.95-1.86 (m, 7H), δ 1.71 (s, 3H), δ 1.33 (s, 9H); MS (ESI) 543.2 (M+H).

HPLC purification afforded the ethyl ester: retention time (min)=1.98, method [1]; ¹H NMR (300 MHz, CD₃OD): δ 7.55 (s, 1H), δ 7.31-7.27 (m, 1H), δ 7.23 (d, J=4 Hz, 2H),

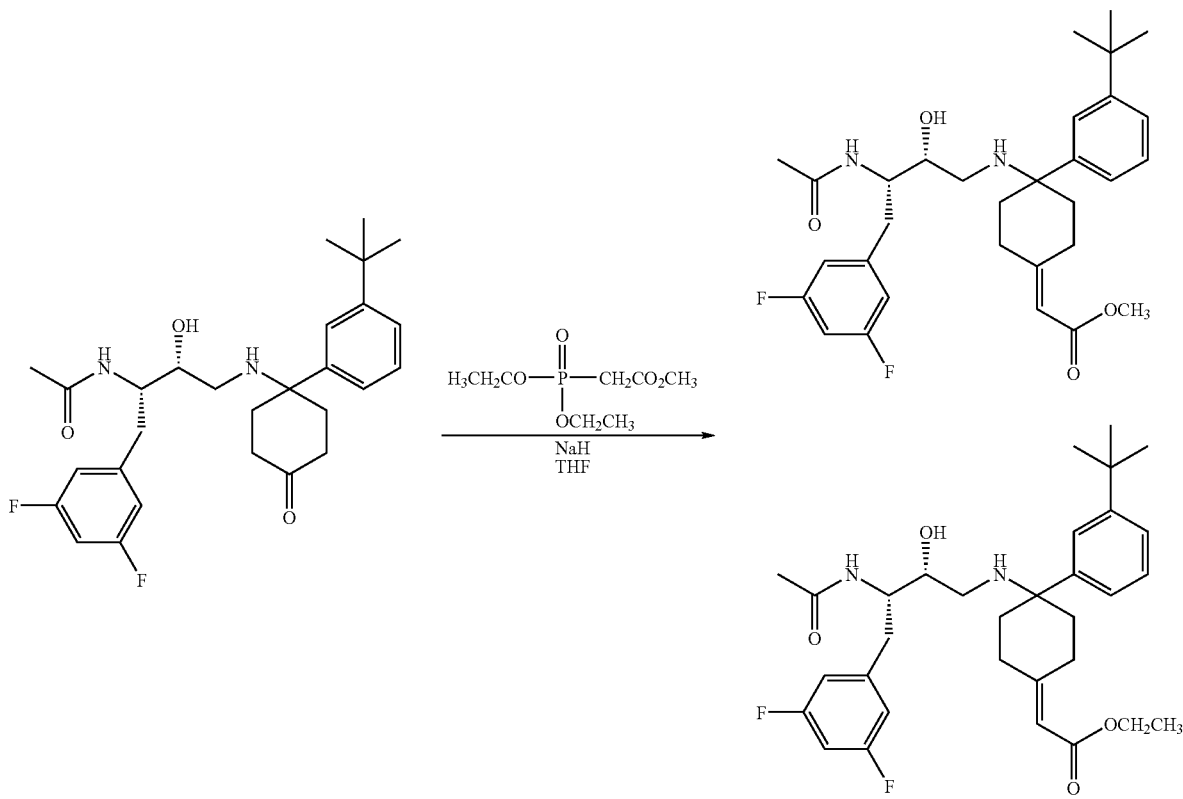

To a solution of methyl diethylphosphonoacetate (0.20 mL, 1.102 mmol) in anhydrous THF (1 mL) was added a 60% dispersion of sodium hydride in mineral oil (0.80 g, 20.0 mmol). Vigourous gas evolution was observed while stirring at RT under N₂(g) inlet. After 2 h a solution of N-[3-[1-(3-tert-butyl-phenyl)-4-oxo-cyclohexylamino]-1-(3,5-difluoro-benzyl)-2-hydroxyl-propyl]-acetamide (0.291

δ 6.70 (d, J=8 Hz, 3H), δ 4.20-4.13 (m, 2H), δ 3.82-3.76 (m, 1H), δ 3.36-3.35 (m, 1H), δ 2.82 (d, J=4 Hz, 1H), δ 2.78 (s, 2H), δ 2.50 (t, 1H), δ 2.33 (d, J=10 Hz, 1H), δ 2.23 (d, J=10 Hz, 1H), δ 2.16-2.07 (m, 1H), δ 1.95-1.80 (m, 7H), δ 1.70 (s, 3H), δ 1.32 (s, 9H), δ 1.30 (t, 3H); MS (ESI) 557.3 (M+H).

EXAMPLE 22

Preparation of 2-[4-[3-ACETYLAMINO-4-3,5-DIFLUORO-PHENYL)-2-HYDROXY-BUTYLAMINO]-4-(3-TERT-BUTYL-PHENYL)-CYCLOHEXYLIDENE]-N,N-DIMETHYL-ACETAMIDE

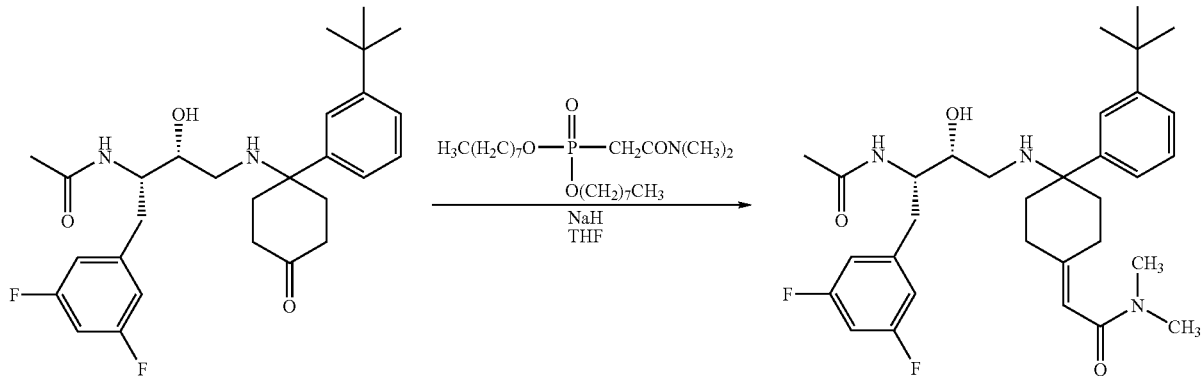

To a solution of dioctyl (N,N-dimethylcarbamoylmethyl) phosphonate (0.05 g, 0.128 mmol) in anhydrous THF (1 mL) was added a 60% dispersion of sodium hydride in mineral oil (0.026 g, 0.65 mmol). Vigorous gas evolution was observed while stirring at room temperature under $N_2(g)$ inlet. After 3.5 h a solution of N-[3-[1-(3-tert-butyl-phenyl)-4-oxo-cyclohexylamino]-1-(3,5-difluoro-benzyl)-2-hydroxyl-propyl]-acetamide (0.041 g, 0.084 mmol) in anhydrous THF (1 mL) was added to the reaction flask. The mixture was allowed to stir overnight. The reaction was quenched with $H_2O$ and extracted with $CH_2Cl_2$. The organic layer was collected, dried over anhydrous sodium sulfate, filtered and concentrated. HPLC purification afforded the parent compound: retention time (min)=1.83, method [1]; $^1$H NMR (300 MHz, $CD_3OD$): δ 7.53 (s, 1H), δ 7.24 (m, 1H), 7.22 (d, J=4 Hz, 2H), 6.68 (d, J=8 Hz, 3H), 3.78 (m, 1H), 3.41 (m, 1H), 3.12 (s, 3H), 2.94 (s, 3H), 2.84 (s, 2H), 2.79 (d, J=15 Hz, 1H), 2.49 (t, 1H), 2.32-2.22 (m, 2H), 2.06 (m, 2H), 1.85 (m, 6H), 1.64 (s, 3H), 1.29 (s, 9H); MS (ESI) 556.3 (M+H).

EXAMPLE 23

Preparation of N-[3-[1-(3-TERT-BUTYL-PHENYL)-4-CYANOMETHYLENE-CYCLOHEXYLAMINO]-1-(3,5-DIFLUORO-BENZYL)-2-HYDROXY-PROPYL]-ACETAMIDE

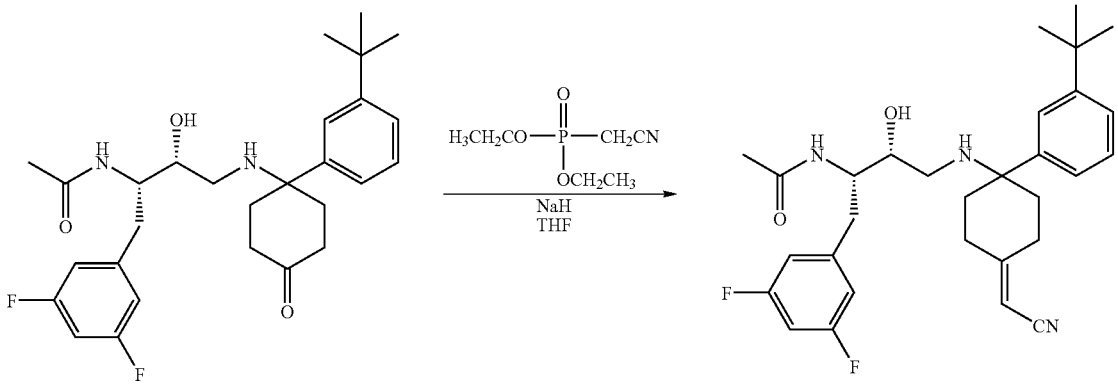

To a solution of diethyl(cyanomethyl)phosphonate (0.05 mL, 0.309 mmol) in anhydrous THF (0.7 mL) was added a 60% dispersion of sodium hydride in mineral oil (0.008 g, 0.20 mmol). Vigourous gas evolution was observed while stirring at RT under $N_2$(g) inlet. After 1.5 h a solution of N-[3-[1-(3-tert-butyl-phenyl)-4-oxo-cyclohexylamino]-1-(3,5-difluoro-benzyl)-2-hydroxyl-propyl]-acetamide (0.119 g, 0.123 mmol) in anhydrous THF (0.5 mL) was added to the reaction flask. The mixture was allowed to stir overnight. The reaction was quenched with $H_2O$ and extracted with $CH_2Cl_2$. The organic layer was collected, dried over anhydrous $Na_2SO_4$, filtered and concentrated. The crude product was purified by HPLC yielding the trifluoroacetic acid salt: retention time (min)=1.81, method [1]; MS (ESI) 510.2 (M+H).

EXAMPLE 24

Preparation of Hydrazones

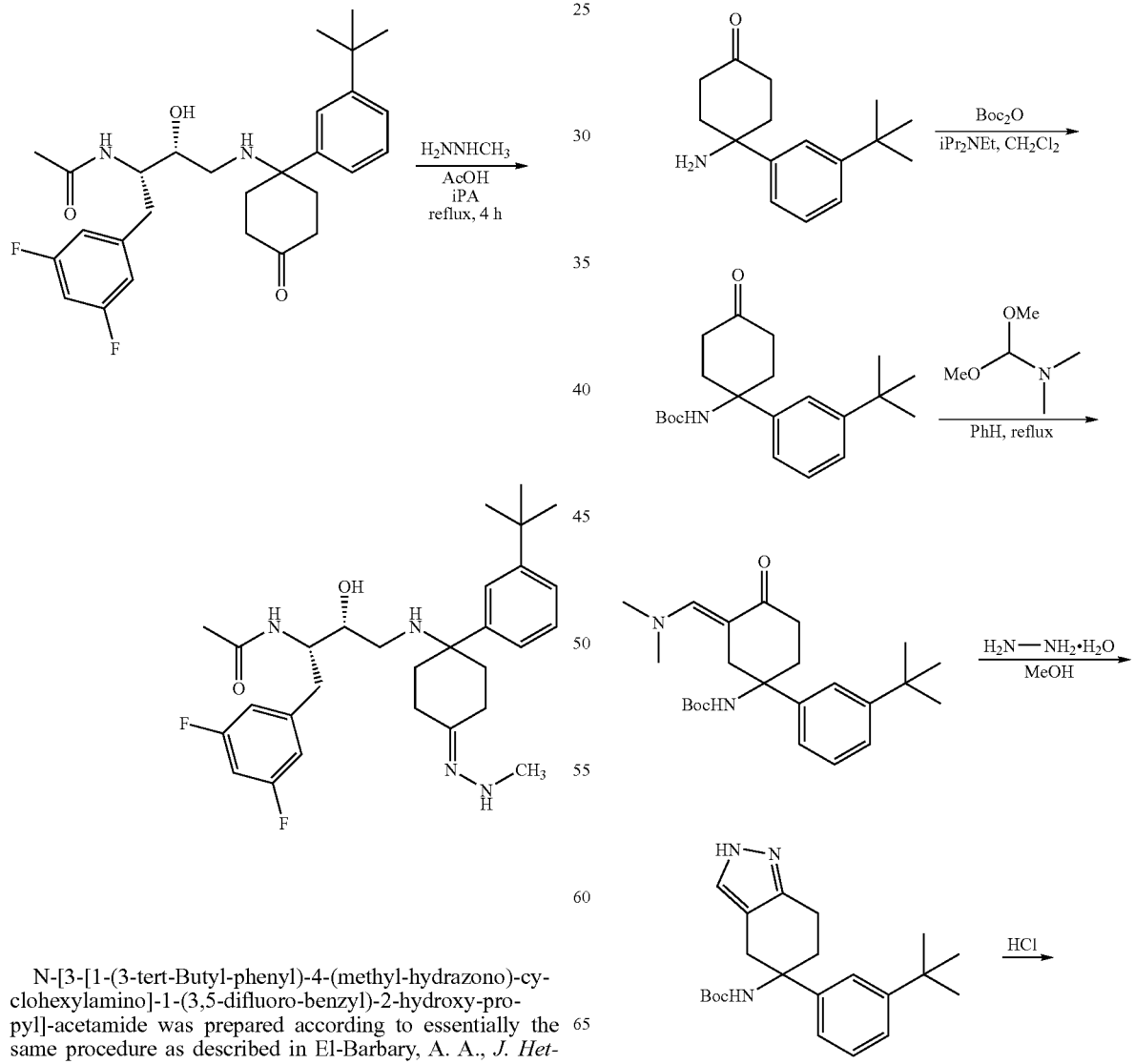

N-[3-[1-(3-tert-Butyl-phenyl)-4-(methyl-hydrazono)-cyclohexylamino]-1-(3,5-difluoro-benzyl)-2-hydroxy-propyl]-acetamide was prepared according to essentially the same procedure as described in El-Barbary, A. A., *J. Heterolytic Chem.*, 38 (2001), 1711-16.

EXAMPLE 25

Preparation of (2R,3S)-N-[3-[5-(3-TERT-BUTYL-PHENYL)-4,5,6,7-TETRAHYDRO-2H-INDAZOL-5-YLAMINO]-1-(3,5-DIFLUORO-BENZYL)-2-HYDROXY-PROPYL]-ACETAMIDE AND (2R, 3S)-N-[3-[2-ACETYL-5-(3-TERT-BUTYL-PHENYL)-4,5,6,7-TETRAHYDRO-2H-INDAZOL-5-YLAMINO]-1-(3,5-DIFLUORO-BENZYL)-2-HYDROXY-PROPYL]-ACETAMIDE

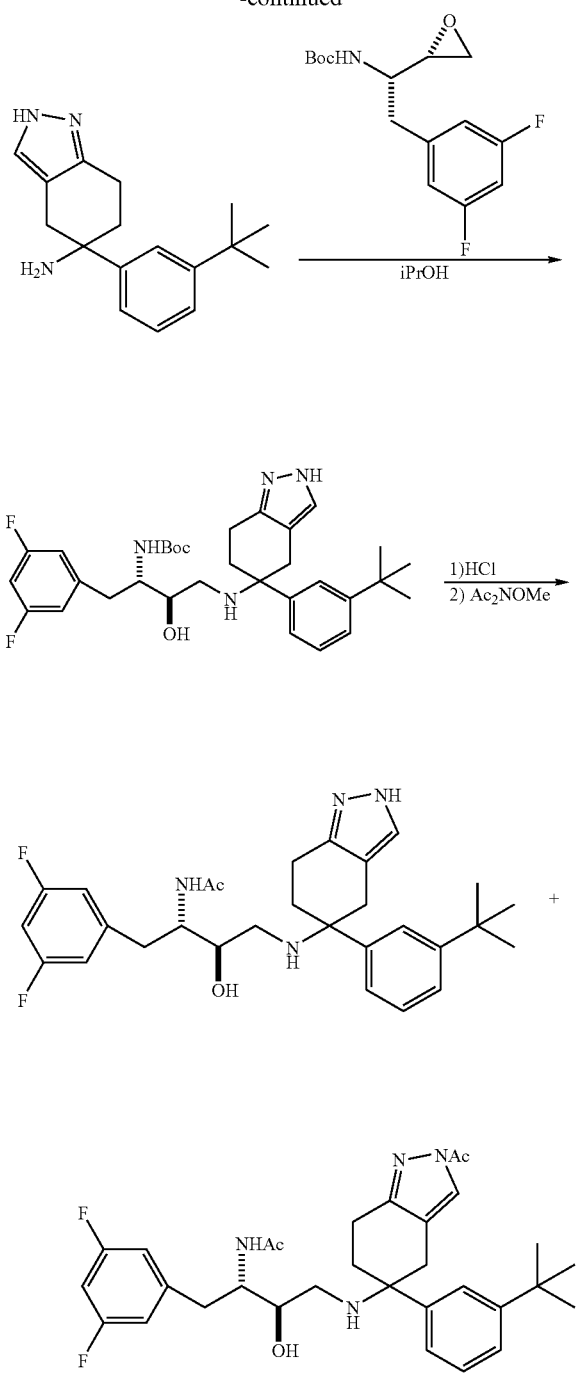

N NaOH solution, then extracted with ethyl acetate (3×25 mL). The combined organic layers were washed (brine), dried (Na$_2$SO$_4$), filtered and concentrated under reduced pressure. Material was pure by HPLC/MS: retention time=1.18 min, method [7]; mass spec (ESI) 246 (MH$^+$, 33), 229 (M−NH$_2^+$, 100), 228 (28), 173 (47).

Step 2. [1-(3-tert-Butyl-phenyl)-4-oxo-cyclohexyl]-carbamic acid tert-butyl ester 4-Amino-4-(3-tert-butyl-phenyl)-cyclohexanone (441 mg, 1.8 mmol) was dissolved in dry methylene chloride (10 mL), diisopropylethylamine (0.31 mL, 1.8 mmol) and di-tert-butyl carbonate (400 mg, 1.83 mmol) were added in succession at room temperature. After 19 h, the reaction was concentrated under reduced pressure, and the desired product isolated by chromatography (R$_f$=0.35 in 20% EtOAc/hexanes). The resulting oil was taken to the next reaction: retention time=2.57 min, method [7]; mass spec (ESI) 369 (24), 368 (100), 272 (42), 211 (24).

Step 3. [5-(3-tert-Butyl-phenyl)-4,5,6,7-tetrahydro-2H-indazol-5-yl]-carbamic acid tert-butyl ester

[1-(3-tert-Butyl-phenyl)-4-oxo-cyclohexyl]-carbamic acid tert-butyl ester (155 mg, 0.45 mmol) was heated with triethylamine (0.010 mL, 0.07 mmol) and dimethylformamide dimethyl acetal (0.38 mL, 2.9 mmol) in benzene (~20 mL) to reflux in a round-bottom flask fitted with a Dean-Stark trap and a condenser. Benzene was distilled to about one third the original volume, then fresh benzene was added and the distillation continued. This process was repeated until reaction showed absence of starting material by TLC (~24 h). The solvent was evaporated. The crude [1-(3-tert-Butyl-phenyl)-3-dimethylaminomethylene-4-oxo-cyclohexyl]-carbamic acid tert-butyl ester was used in the next reaction without further purification.

To crude [1-(3-tert-Butyl-phenyl)-3-dimethylaminomethylene-4-oxo-cyclohexyl]-carbamic acid tert-butyl ester (91 mg, 0.227 mmol) was added ethanol (6 mL) and hydrazine hydrate (0.010 mL, 0.32 mmol). The reaction mixture was stirred at room temperature for 12 h then placed in a freezer overnight. The reaction mixture was concentrated under reduced pressure yielding the title compound: R$_f$=0.35 in 5% MeOH/CH$_2$Cl$_2$; retention time=1.92 min, method [7]; mass spec (ESI) 392 (25), 370 (2), 315 (24), 314 (100).

Step 4. 5-(3-tert-Butyl-phenyl)-4,5,6,7-tetrahydro-2H-indazol-5-ylamine

[5-(3-tert-Butyl-phenyl)-4,5,6,7-tetrahydro-2H-indazol-5-yl]-carbamic acid tert-butyl ester (84 mg, 0.23 mmol) was dissolved in 4 N hydrogen chloride in dioxane (2 mL, 8 mmol) at room temperatrure for 90 min, whereupon the reaction was deemed complete by TLC. The reaction mixture was concentrated under reduced pressure and the amine hydrochloride salt was basified by partitioning between 1 N aqueous NaOH and 33% isopropanol in chloroform. The organic layer was separated and the aqueous layer extracted twice with additional 33% IPA/CHCl$_3$. The combined organic layers were dried (Na$_2$SO$_4$), filtered and concentrated. LC/MS analysis showed 90% pure material, which Step 1.
4-Amino-4-(3-tert-butyl-phenyl)-cyclohexanone A solution of 8-(3-tert-Butyl-phenyl)-1,4-dioxa-spiro[4.5]dec-8-ylamine hydrochloride (337 mg, 1.03 mmol) in glacial acetic acid (9 mL) and water (4 mL) was heated to 75° C. for 21 h, whereupon the reaction was deemed complete by HPLC analysis. The reaction mixture was basified with 2.5 was taken to subsequent reactions: $R_f$=0.098 in 25% MeOH/ CH$_2$Cl$_2$; retention time=0.98 min, method [7]; mass spec (ESI) 270 (6), 254 (23), 253 (100), 197 (12).

Step 5. (2R,3S)-[3-[5-(3-tert-Butyl-phenyl)-4,5,6,7-tetrahydro-2H-indazol-5-ylamino]-1-(3,5-difluoro-benzyl)-2-hydroxy-propyl]-carbamic acid tert-butyl ester

[2-(3,5-Difluorophenyl)-1-oxiranyl-ethyl]-carbamic acid tert-butyl ester (80.2 mg, 0.268 mmol) was combined with 5-(3-tert-Butyl-phenyl)-4,5,6,7-tetrahydro-2H-indazol-5-ylamine (61 mg, 0.227 mmol) in isopropanol (1 mL). This mixture was heated to 80° C. for 16 h, whereupon the reaction mixture was concentrated under reduced pressure and the crude reaction mixture purified by flash chromatography yielding 61 mg (47%) desired product: $R_f$=0.40 in 10% MeOH/CH$_2$Cl$_2$; retention time=1.84 min, method [7]; mass spec (ESI) 591 (20), 570 (42), 569 (100).

Step 6. (2R,3S)-N-[3-[5-(3-tert-Butyl-phenyl)-4,5,6,7-tetrahydro-2H-indazol-5-ylamino]-1-(3,5-difluoro-benzyl)-2-hydroxy-propyl]-acetamide and (2R,3S)-N-[3-[2-Acetyl-5-(3-tert-butyl-phenyl)-4,5,6,7-tetrahydro-2H-indazol-5-ylamino]-1-(3,5-difluoro-benzyl)-2-hydroxy-propyl]-acetamide (2R,3S)-[3-[5-(3-tert-Butyl-phenyl)-4,5,6,7-tetrahydro-2H-indazol-5-ylamino]-1-(3,5-difluoro-benzyl)-2-hydroxy-propyl]-carbamic acid tert-butyl ester (61 mg, 0.11 mmol) was dissolved in 4 N hydrogen chloride in dioxane (2 mL) at room temperature. After 90 min, the reaction mixture was concentrated under reduced pressure. The crude residue was partitioned between 1 N aqueous NaOH and dichloromethane. The layers were separated and the aqueous layer further extracted with dichloromethane twice. The combined organic washes were dried (Na$_2$SO$_4$), filtered and concentrated yielding a foam (50 mg), which was used in the subsequent reaction without further purification.

The crude amine (50 mg, 0.11 mmol) was dissolved in dry dichloromethane (1 mL), and N,N-diacetylhydroxylamine (0.025 mL, 0.21 mmol) was added dropwise by syringe. After 20 h at room temperature, the reaction was concentrated under reduced pressure. The crude residue was purified by HPLC.

(2R,3S)-N-[3-[5-(3-tert-Butyl-phenyl)-4,5,6,7-tetrahydro-2H-indazol-5-ylamino]-1-(3,5-difluoro-benzyl)-2-hydroxy-propyl]-acetamide (1:1 mixture of two regioisomers): retention time=1.48 min, method [7]; mass spec (ESI) 533 (18), 512 (39), 511 (100), 259 (18), 253 (16).

EXAMPLE 26

NH$_2$ Replacement of Hydroxyl Alpha to the —(CHR$_1$)— Group of Compounds of Formula (I)

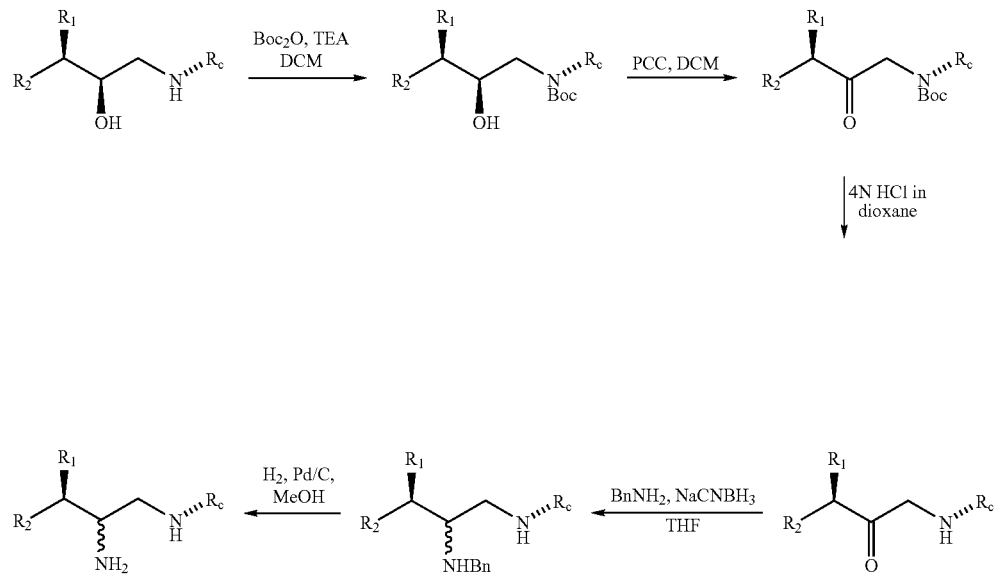

EXAMPLE 27
SH Replacement of Hydroxyl Alpha to the
—(CHR₁)— Group of Compounds of Formula (I)
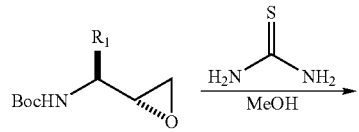
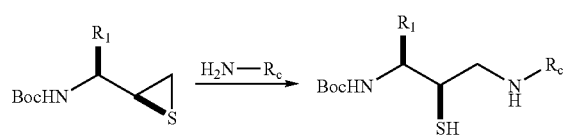
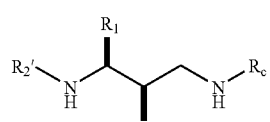
EXAMPLE 28
Preparation of 1-[5-(3-TERT-BUTYL-PHENYL)-4,
5,6,7-TETRAHYDRO-2H-INDAZOL-5-
YLAMINO]-4-(3,5-DIFLUORO-PHENYL)-BU-
TAN-2-OL
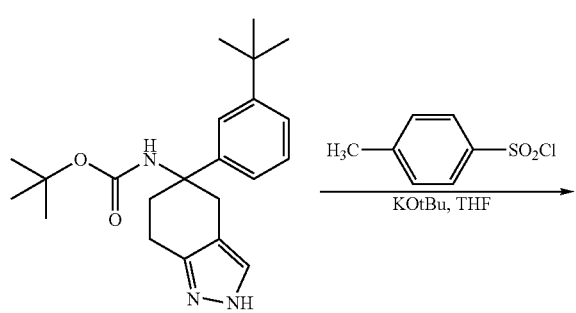
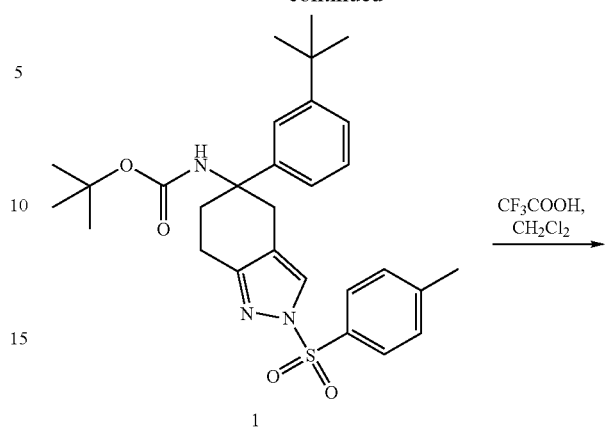
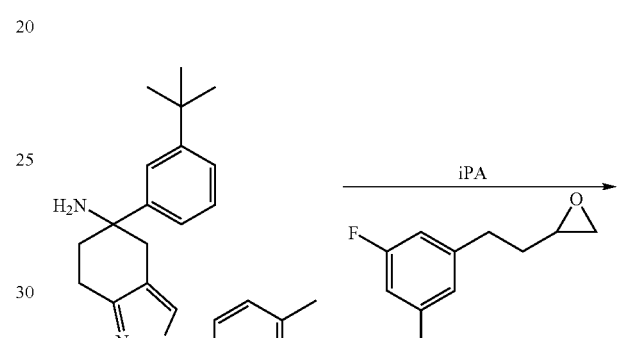
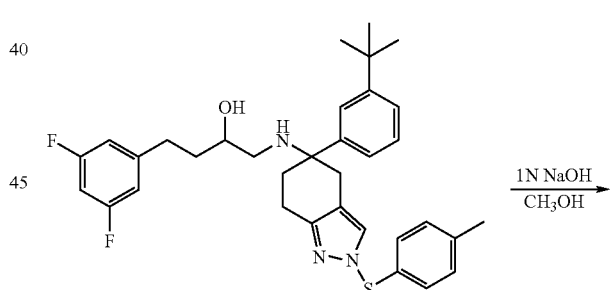
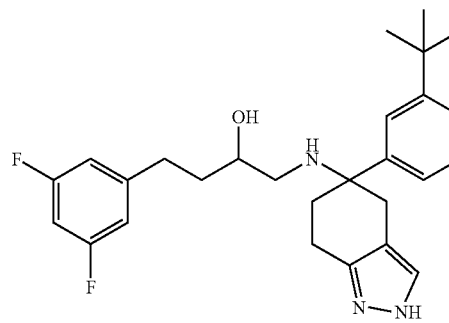

Step 1. Preparation of [5-(3-tert-butyl-phenyl-2-(toluene-4-sulfonyl)-4,5,6,7-tetrahydro-2H-indazol-5-yl]-carbamic acid tert-butyl ester To [5-(3-tert-butyl-phenyl)-4,5,6,7-tetrahydro-2H-indazol-5-yl]-carbamic acid tert-butyl ester (0.58 g, 1.58 mmol) in THF (6 mL) cooled to 0° C. was added a 1.0 M solution of potassium tert-butoxide (3.5 mL). After 1.5 h a solution of p-toluenesulfonyl chloride (0.54 g, 2.81 mmol) was added and the mixture was stirred overnight while warming to ambient temperature. The reaction mixture was concentrated under reduced pressure, dissolved in $CH_2Cl_2$ and washed with $H_2O$ followed by sat. NaCl (aq). The organic layer was collected, dried over anhydrous $Na_2SO_4$, filtered and concentrated. The crude product was purified by flash chromatography, eluting with 30% ethyl acetate in hexane to afford 0.63 g (1.20 mmol, 76%) of [5-(3-tert-butyl-phenyl-2-(toluene-4-sulfonyl)-4,5,6,7-tetrahydro-2H-indazol-5-yl]-carbamic acid tert-butyl ester: retention time (min)=3.18, method [1]. MS (ESI) 524.2 (M+H).

Step 2. Preparation of 5-(3-tert-butyl-phenyl)-2-(toluene-4-sulfonyl)-4,5,6,7-tetrahydro-2H-indazol-5-ylamine To a solution of [5-(3-tert-butyl-phenyl-2-(toluene-4-sulfonyl)-4,5,6,7-tetrahydro-2H-indazol-5-yl]-carbamic acid tert-butyl ester (0.61 g, 1.17 mmol) dissolved in $CH_2Cl_2$ (1 mL) was added trifluoacetic acid (1 mL). The reaction mixture was allowed to stir for 1 h prior to quenching with sat. $NaHCO_3$ (aq) and conc. $NH_4OH$. The product was extracted with $CH_2Cl_2$ and the organic layer was collected, dried over anhydrous $Na_2SO_4$, filtered and concentrated to afford 0.41 g of crude 5-(3-tert-butyl-phenyl)-2-(toluene-4-sulfonyl)-4,5,6,7-tetrahydro-2H-indazol-5-ylamine: retention time of diastereomers (min)=1.62 and 1.71, method [1]. MS (ESI) 407.4 (M+H).

Step 3. Preparation of 1-[5-(3-tert-butyl-phenyl)-2-(toluene-4-sulfonyl)-4,5,6,7-tetrahydro-2H-indazol-5-ylamino]-4-(3,5-difluoro-phenyl)-butan-2-ol To a sealed tube was added a solution of 5-(3-tert-butyl-phenyl)-2-(toluene-4-sulfonyl)-4,5,6,7-tetrahydro-2H-indazol-5-ylamine (0.41 g, 1.0 mmol) in isopropyl alcohol followed by 2-[2-(3,5-difluoro-phenyl)-ethyl]-oxirane (0.18 g, 1.0 mmol). The reaction was heated at 50° C. overnight and no product was formed. After heating at 100° C. for an additional 3.5 h the reaction was complete. The reaction mixture was concentrated and the crude product was purified by flash chromatography, eluting with 3% methanol in $CHCl_3$ to afford 0.25 g (0.41 mmol, 42%) of 1-[5-(3-tert-butyl-phenyl)-2-(toluene-4-sulfonyl)-4,5,6,7-tetrahydro-2H-indazol-5-ylamino]-4-(3,5-difluoro-phenyl)-butan-2-ol: retention time (min)=2.15, method [1]. MS (ESI) 608.4 (M+H).

Step 4. Preparation of 1-[5-(3-tert-butyl-phenyl)-4,5,6,7-tetrahydro-2H-indazol-5-ylamino]-4-(3,5-difluoro-phenyl)-butan-2-ol To a solution of 5-(3-tert-butyl-phenyl)-2-(toluene-4-sulfonyl)-4,5,6,7-tetrahydro-2H-indazol-5-ylamine in methanol (4 mL) was added 1 N NaOH (1 mL). The reaction mixture was stirred at ambient temperature 5.5 h prior to quenching with $H_2O$. The product was extracted with EtOAc and the organic layer was collected, dried over anhydrous $NaSO_4$, filtered and concentrated. The crude product was purified by flash chromatography, eluting solvent with 5% methanol in $CH_2Cl_2$ and $NH_4OH$ to afford 1-[5-(3-tert-butyl-phenyl)-4,5,6,7-tetrahydro-2H-indazol-5-ylamino]-4-(3,5-difluoro-phenyl)-butan-2-ol. HPLC purification afforded the parent compound: retention time (min)=4.77, method [1]; MS (ESI) 454.2 (M+H).

EXAMPLE 29

Preparation of 1-[5-(3-TERT-BUTYL-PHENYL)-2-METHYL-4,5,6,7-TETRAHYDRO-2H-INDAZOL-5-YLAMINO]-4-(3,5-DIFLUORO-PHENYL)-BUTAN-2-OL

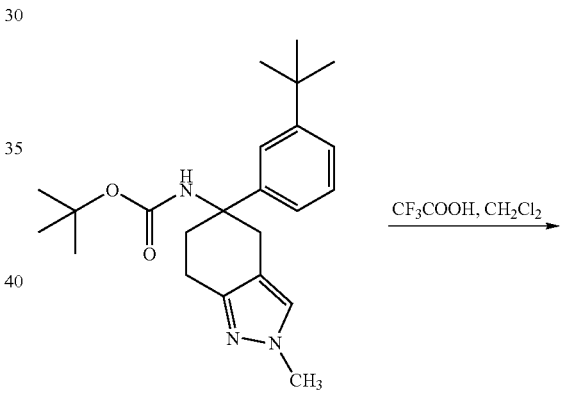

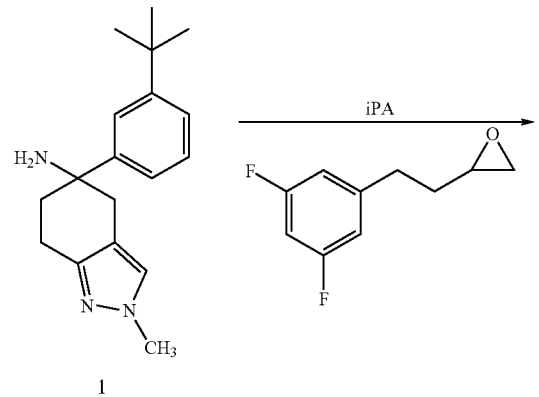

1

-continued

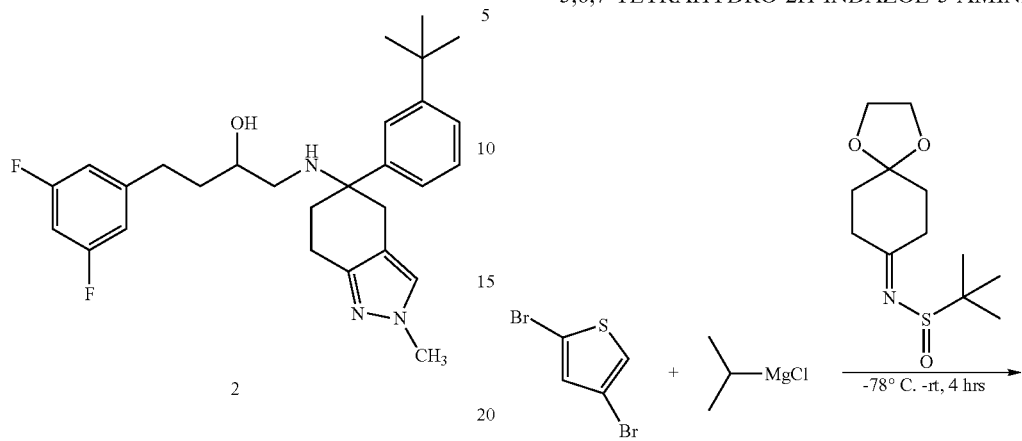

2

Step 1. Preparation of 5-(3-tert-butyl-phenyl)-2-methyl-4,5,6,7-tetrahydro-2H-indazol-5-yl amine To a solution of [5-(3-tert-butyl-phenyl-2-methyl-4,5,6,7-tetrahydro-2H-indazol-5-yl]-carbamic acid tert-butyl ester (0.33 g, 0.86 mmol) dissolved in CH$_2$Cl$_2$ (1 mL) was added trifluoacetic acid (1 mL). The reaction mixture was allowed to stir for 1.5 h prior to quenching with sat. NaHCO$_3$ (aq) and conc. NH$_4$OH. The product was extracted with CH$_2$Cl$_2$ and the organic layer was collected, dried over anhydrous Na$_2$SO$_4$, filtered and concentrated to afford 0.17 g of crude 5-(3-tert-butyl-phenyl)-2-methyl-4,5,6,7-tetrahydro-2H-indazol-5-ylamine: retention time (min)=1.04, method [1]. MS (ESI) 267.2 (M+H).

Step 2. Preparation of 1-[5-(3-tert-butyl-phenyl)-2-methyl-4,5,6,7-tetrahydro-2H-indazol-5-ylamino]-4-(3,5-difluoro-phenyl)-butan-2-ol To a sealed tube was added 2-[2-(3,5-difluoro-phenyl)-ethyl]-oxirane (0.124 g, 0.673 mmol) and 5-(3-tert-butyl-phenyl)-2-methyl-4,5,6,7-tetrahydro-2H-indazol-5-ylamine (0.174 g, 0.614 mmol) in a solution of isopropyl alcohol (2.5 mL). The reaction mixture was heated at 120° C. for 4 h and concentrated to yield crude product. The crude product was purified by flash chromatography, eluting with 50% hexane in ethyl acetate, 5% CH$_3$OH in CH$_2$Cl$_2$ and conc. NH$_4$OH to afford 0.089 g (0.19 mmol, 31%) of the 1-[5-(3-tert-butyl-phenyl)-2-methyl-4,5,6,7-tetrahydro-2H-indazol-5-ylamino]-4-(3,5-difluoro-phenyl)-butan-2-ol 2. HPLC purification afforded the trifluoroacetic acid salt: retention time (min)=1.80, method [1]; $^1$H NMR (300 MHz, CD$_3$OD): δ 7.60 (d, J=2 Hz, 1H), δ 7.59-7.27 (m, 4H), δ 6.81-6.75 (m, 3H), δ 3.81 (s, 3H), δ 3.75 (m, 1H), δ 3.70 (s, 2H), δ 3.09-3.02 (m, 2H), δ 2.88-2.04 (m, 6H), δ 1.71-1.61 (m, 1H), δ 1.37 (m, 2H), δ 1.28 (s, 9H); MS (ESI) 468.3 (M+H).

EXAMPLE 30

Preparation of 5-(4-BROMOTHIOPHEN-2-YL)-4,5,6,7-TETRAHYDRO-2H-INDAZOL-5-AMINE

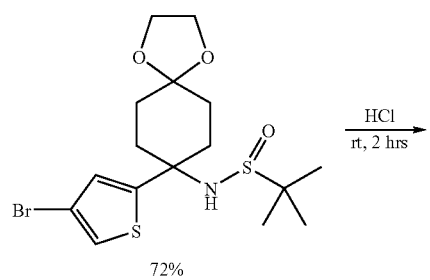

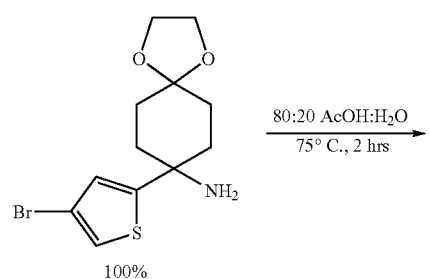

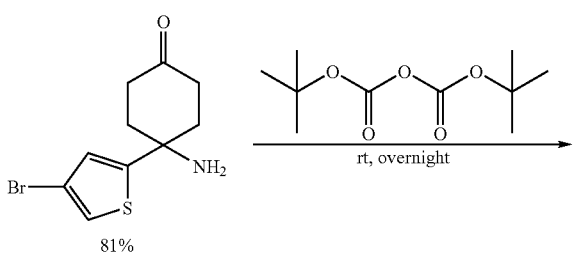

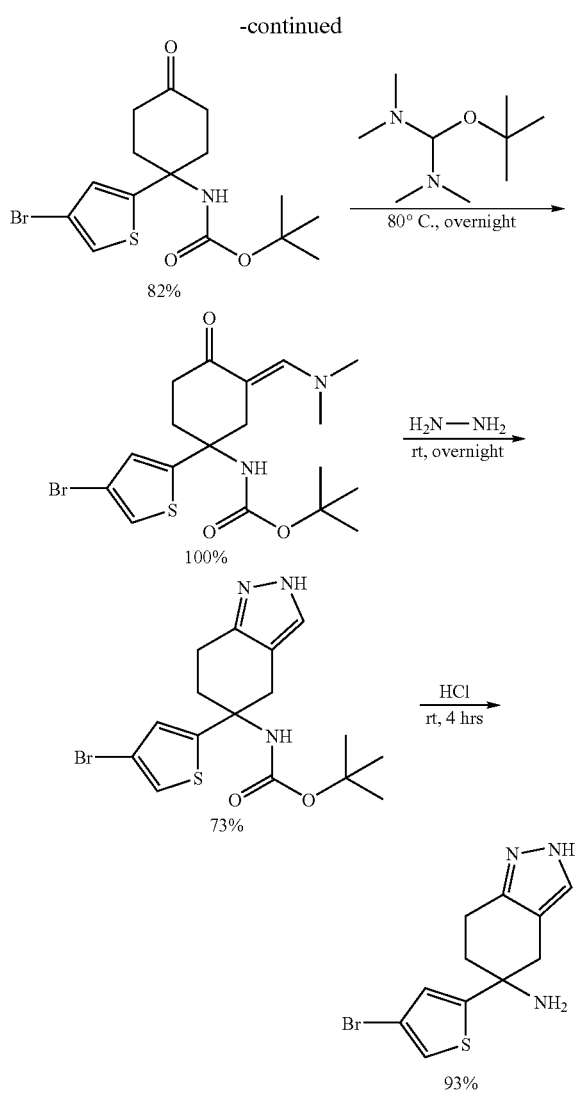

Step 1: Preparation of tert-butyl 1-(4-bromothiophen-2-yl)-4-(1,3-dioxol-2-yl)cyclohexylcarbamate To a stirred solution under nitrogen of 2,4-dibromothiophene (2.24 g, 9.25 mmol) in Et$_2$O (4 mL) at 0° C. was added isopropylmagnesium chloride (2.0 M, 4.78 mL, 9.56 mmol). The reaction was stirred for 30 min to form the grignard reagent. After this time the reaction was cooled to −78° C. and a solution of 2-Methylpropane-2-sulfinic acid (1,4-dioxa-spiro[4.5]dec-8-ylidene)-amide in Et$_2$O (and minimal toluene for solubility) was added to the reaction. Upon addition of the 2-Methylpropane-2-sulfinic acid (1,4-dioxa-spiro[4.5]dec-8-ylidene)-amide the reaction was allowed to warm to room temperature and stirred for 3 h. The reaction was then cooled to 0° C. and quenched with water. This mixture was extracted with EtOAc (2×) and the organic phase washed with brine and dried over MgSO$_4$. The crude product was analyzed by TLC (100% EtOAc), LC and LC/MS. The solution was then concentrated and purified on the Biotage Horizon (65+M silica gel, 10% to 100% EtOAC/Hex51 mL-1836 mL, 100% EtOAc 51 mL-612 mL, 100% EtOAc 51 mL-1224 mL). The appropriate fractions were combined (last eluting) and concentrated to give the thiophene product as a colorless foam in 72% yield: $^1$H NMR (CDCl$_3$) δ7.18 (s, 1H), 7.03 (s, 1H), 4.00-3.90 (m, 4H), 3.43 (s, 1H), 2.43-2.20 (m, 4H), 1.95-1.65 (m, 4H), 1.17 (s, 9H); retention time (min)=3.66 (method [8]); MS (ESI) 122.0.

Step 2: 4-amino-4-(4-bromothiophen-2-yl)-1(1,3-dioxol-2-yl)cyclohexane

To the sulfonylated amine (983 mg, 2.22 mmol) was added HCl (4.0 M in p-dioxane, 5.56 mL, 22.2 mmol) and p-dioxane (4 mL). The reaction was stirred for 2 h at room temperature and monitored by LC/MS. Following addition of the acid a white precipitate formed and persisted for the remainder of the reaction. After this time the reaction was concentrated to a pale yellow oil to afford the deprotected product as the HCl salt. The product was used crude in step 3: retention time (min)=2.47 (method [8]); MS (ESI) 300.9.

Step 3: 4-amino-4-(4-bromothiophen-2-yl)cyclohexanone

To the amine (837 mg, 2.63 mmol) was added an 80:20 solution of AcOH:H$_2$O (11.5 mL). The reaction was heated to 75° C. and allowed to stir at this temperature for 2 h. After LC/MS analysis the reaction was allowed to cool to room temperature and then concentrated. The resulting pale orange solid was then re-dissolved in EtOAc and brought to a basic pH (10) with 2M NaOH. The aqueous phase was then extracted with an additional amount of EtOAc, and all organics combined, dried over MgSO$_4$, and concentrated to afford the crude product in 81% yield: retention time (min) =1.47 (method [8]); MS (ESI) 273.9 ($^{79}$Br isotope).

Step 4: tert-butyl 1-(4-bromothiophen-2-yl)-4-oxocyclohexylcarbamate

To a stirred solution of the ketone (584 mg, 2.13 mmol) in DCM (8 mL) was added Boc anhydride (697 mg, 3.20 mmol). The reaction was allowed to stir at room temperature overnight. The following morning the reaction was analyzed by TLC (4:1 Hex/EtOAc, MeOH/DCM) and LC/MS. Based on these results more Boc anhydride was added (1 eq) and the reaction allowed to continue stirring overnight. After this time the reaction was concentrated and purified on the Biotage Horizon (40+M silica gel). The appropriate fractions were combined (TLC 4:1 Hex/EtOAc), concentrated to give the desired product in 82% yield: $^1$H NMR (CDCl$_3$) δ7.07 (s, 1H), 6.90 (s, 1H), 4.98 (s, 1H), 2.82-2.65 (m, 2H), 2.65-2.50 (m, 2H), 2.45-2.35 (m, 2H), 2.30-2.20 (m, 2H), 1.41 (s, 9H).

Step 5: (E)-tert-butyl 1-(4-bromothiophen-2-yl)-3-((dimethylamino)methylene)-4-oxocyclohexylcarbamate To the ketone (657 mg, 1.76 mmol) in toluene (20 mL), at room temperature under nitrogen, was added tert-butoxybis(dimethylamino)methane (0.4 mL, 1.93 mmol). The reaction was then heated to 80° C. and left to stir overnight. The following morning the reaction was analyzed by TLC and determined to have gone to completion. The reaction was allowed to cool, then concentrated and used directly in Step 6: retention time (min)=2.08 (method [8]); MS (ESI) 430.9.

Step 6: tert-butyl 5-(4-bromothiophen-2-yl)-4,5,6,7-tetrahydro-2H-indazol-5-ylcarbamate To a stirred solution of the enamine (557 mg, 1.91 mmol) in EtOH (20 mL) at room temperature was added hydrazine (119 µl, 3.81 mmol). The reaction was allowed to stir overnight and monitored by LC/MS and TLC (10% MeOH in DCM). The following morning the reaction was concentrated and then purified on the Biotage Horizon (40+M silica gel, 5% to 75% B:20% MeOH/DCM, 21 mL-1512 mL). The appropriate fractions were combined and concentrated to give a yellow foam in 73% yield: retention time (min)=2.17 (method [8]); MS (ESI) 399.8.

Step 7: 5-(4-bromothiophen-2-yl)-4,5,6,7-tetrahydro-2H-indazol-5-amine

To a stirred solution of the indazole (557 mg, 1.40 mmol) in p-dioxane (2 mL) was added HCl (4.0M in p-dioxane, 1.75 mL, 6.99 mmol). The reaction was allowed to stir for 2 h and monitored by TLC (20% MeOH/DCM), LC and LC/MS. After this time the reaction was concentrated and placed on the high vacuum for 48 h. After this time the reaction was analyzed by LC and LC/MS and determined not to have gone to completion. Therefore, p-dioxane (2 mL) and HCl (4.0M in p-dioxane, 1.75 mL, 6.99 mmol) were added to the dried reaction and allowed to stir for an additional two h. The reaction was then concentrated, triturated with ether/DCM, and the desired product collected as a light orangish yellow solid in 93% yield: $^1$H NMR (DMSO-d$_6$) δ 8.88 (s, 1H), 7.65 (s, 1H), 7.52 (s, 1H), 7.38 (s, 1H), 4.80 (br s, 2H), 3.33 (d, J=14 Hz, 1H), 3.14 (d, J=14 Hz, 1H), 2.85-2.72 (m, 1H), 2.50-2.30 (m, 3H); retention time (min)=2.20 (method [8]); MS (ESI) 300.1 (60), 283.1 ($^{81}$Br, 100).

EXAMPLE 31

Preparation of 5-(3-TERT-BUTYLPHENYL)-4,5,6,7-TETRAHYDRO-2H-INDAZOL-5-AMINE

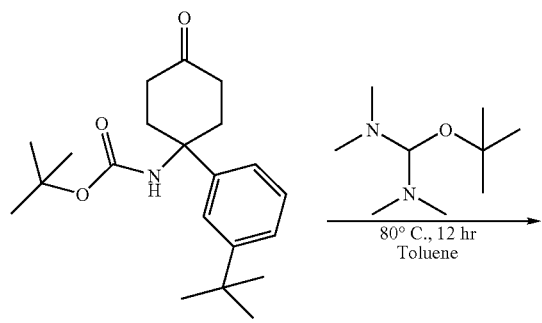

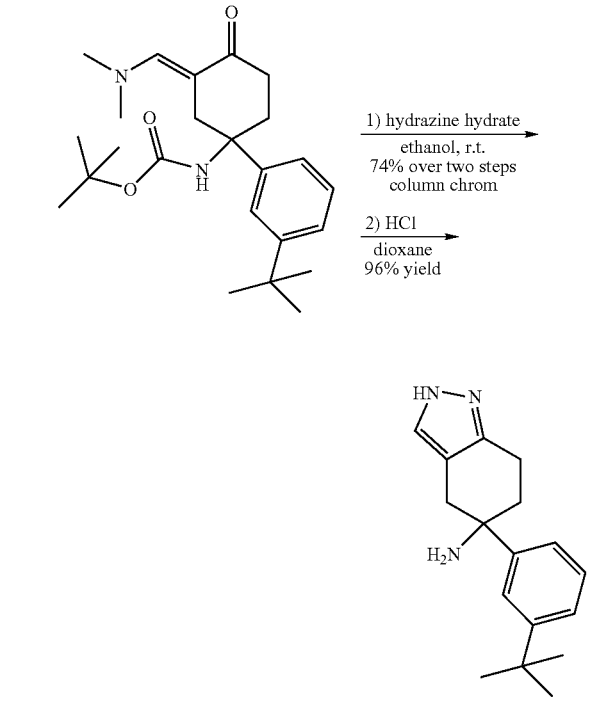

Step 1: (E)-tert-butyl 1-(3-tert-butylphenyl)-3-((dimethylamino)methylene)-4-oxocyclohexylcarbamate To a stirred solution of tert-butyl 1-(3-tert-butylphenyl)-4-oxocyclohexylcarbamate (691 mg, 2.0 mmol) in Toluene (5 mL) was added tert-butoxybis(dimethylamino)methane (454 µL, 2.2 mmol). The reaction was stirred at 85° C. overnight. The reaction was concentrated and used crude in the next step.

Step 2: Tert-butyl 5-(3-tert-butylphenyl)-4,5,6,7-tetrahydro-2H-indazol-5-ylcarbamate To a stirred solution of (E)-tert-butyl 1-(3-tert-butylphenyl)-3-((dimethylamino) methylene)-4-oxocyclohexylcarbamate (801 mg, 2.0 mmol) in 6 mL of ethanol was added hydrazine monohydrate (150 µL, 3.0 mmol). The reaction was allowed to stir for 3 h. The reaction was concentrated and purified using a biotage 40S column eluting with DCM/MeOH (95:5) to afford 500 mg (67% yield) of an off white foam. LCMS corresponded to the desired material: retention time (min)=2.45 (method [8]); MS (ESI) 370.0.

Step 3: 5-(3-tert-butylphenyl)-4,5,6,7-tetrahydro-2H-indazol-5-amine

Tert-butyl 5-(3-tert-butylphenyl)-4,5,6,7-tetrahydro-2H-indazol-5-ylcarbamate (499 mg, 1.35 mmol) was taken up in 2 mL of dioxane followed by the addition of HCl (3.38 mL of a 4N solution in dioxane). The reaction was stirred for 4 h and then concentrated to yield 350 mg (96% yield) of a white solid. $^1$H-NMR (CD$_3$OD) δ 8.17 (d, J=2.7 Hz, 1H), 7.60 (s, 1H), 7.52-7.45 (m, 1H), 7.44-7.32 (m, 2H), 3.77 (d, J=14.8 Hz, 1H), 3.21 (d, J=14.8 Hz, 1H), 3.10-2.94 (m, 1H), 2.82-2.66 (m, 1H), 2.59-2.42 (m, 2H), 1.30 (s, 9H); retention time (min)=1.70 (method [8]); MS (ESI) 253.3.

Generally, the protection of amines is conducted, where appropriate, by methods known to those skilled in the art. See, for example, *Protecting Groups in Organic Synthesis*, John Wiley and Sons, New York, N.Y., 1981, Chapter 7; *Protecting Groups in Organic Chemistry*, Plenum Press, New York, N.Y., 1973, Chapter 2. When the amino protecting group is no longer needed, it is removed by methods known to those skilled in the art. By definition the amino protecting group must be readily removable. A variety of suitable methodologies are known to those skilled in the art; see also T. W. Green and P. G. M. Wuts in *Protective Groups in Organic Chemistry*, John Wiley and Sons, 3$^{rd}$ edition, 1999. Suitable amino protecting groups include t-butoxycarbonyl, benzyl-oxycarbonyl, formyl, trityl, phthalimido, trichloro-acetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxy-carbonyl, cyclopentanyloxycarbonyl, 1-methylcyclo-pentanyloxycarbonyl, cyclohexanyloxycarbonyl, 1-methyl-cyclohexanyloxycabonyl, 2-methylcyclohexanyloxycarbonyl, 2-(4-toluylsulfonyl)ethoxycarbonyl, 2-(methylsulfonyl)-ethoxycarbonyl, 2-(triphenylphosphino)ethoxycarbonyl, fluorenylmethoxycarbonyl, 2-(trimethylsilyl)ethoxy-carbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl, 1-piperidyloxycarbonyl, 9-fluoroenylmethyl carbonate, —CH—CH=CH$_2$, and the like.

In an embodiment, the protecting group is t-butoxycarbonyl (Boc) and/or benzyloxycarbonyl (CBZ). In another embodiment, the protecting group is Boc. One skilled in the art will recognize suitable methods of introducing a Boc or CBZ protecting group and may additionally consult *Protective Groups in Organic Chemistry*, for guidance.

The compounds of the present invention may contain geometric or optical isomers as tautomers. Thus, the present invention includes all tautomers and pure geometric isomers, such as the E and Z geometric isomers, as mixtures thereof. Further, the present invention includes pure enantiomers, diastereomers and/or mixtures thereof, including racemic mixtures. The individual geometric isomers, enantiomers or diastereomers may be prepared or isolated by methods known to those in the art, including, for example chiral chromatography, preparing diastereomers, separating the diastereomers and then converting the diastereomers into enantiomers.

Compounds of the present invention with designated stereochemistry can be included in mixtures, including racemic mixtures, with other enantiomers, diastereomers, geometric isomers or tautomers. In another embodiment, compounds of the present invention are typically present in these mixtures in diastereomeric and/or enantiomeric excess of at least 50%. Compounds of the present invention may be present in these mixtures in diastereomeric and/or enantiomeric excess of at least 80%. Compounds of the present invention with the desired stereochemistry may also be present in diastereomeric and/or enantiomeric excess of at least 90%. Compounds of the present invention with the desired stereochemistry may be present in diastereomeric and/or enantiomeric excess of at least 99%. The compounds of the present invention may have the "S" configuration at position 1. Compounds may also have the "R" configuration at position 2. Compounds may, for example, have the "1S,2R" configuration.

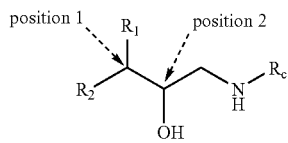

All compound names were generated using AutoNom (AUTOmatic NOMenclature) version 2.1, ACD Namepro version 5.09, Chemdraw Ultra (versions 6.0, 8.0, 8.03, and 9.0), or were derived therefrom.

Several of the compounds of formula (I) are amines, and as such form salts when reacted with acids. Pharmaceutically acceptable salts are preferred over the corresponding amines since they produce compounds which are more water soluble, stable and/or more crystalline.

EXAMPLE 32

Biological Examples

Properties such as efficacy, oral bioavailability, selectivity, or blood-brain penetration can be assessed by techniques and assays known to one skilled in the art. Exemplary assays for determining such properties are found below.

Inhibition of APP Cleavage

The methods of treatment and compounds of the present invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While many theories exist, inhibition of beta-secretase activity is thought to inhibit production of A-beta.

Inhibitory activity is demonstrated in one of a variety of inhibition assays, whereby cleavage of an APP substrate in the presence of beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compounds of formula (I) are known. Representative assay systems are described, for example, in U.S. Pat. Nos. 5,942,400 and 5,744,346, as well as in the Examples below.

The enzymatic activity of beta-secretase and the production of A-beta can be analyzed in vitro or in vivo, using natural, mutated, and/or synthetic APP substrates, natural, mutated, and/or synthetic enzyme, and the compound employed in the particular method of treatment. The analysis can involve primary or secondary cells expressing native, mutant, and/or synthetic APP and enzyme, animal models expressing native APP and enzyme, or can utilize transgenic animal models expressing the substrate and enzyme. Detection of enzymatic activity can be by analysis of at least one of the cleavage products, for example, by immunoassay, fluorometric or chromogenic assay, HPLC, or other means of detection. Inhibitory compounds are determined as those able to decrease the amount of beta-secretase cleavage product produced in comparison to a control, where beta-secretase mediated cleavage in the reaction system is observed and measured in the absence of inhibitory compounds.

Efficacy reflects a preference for a target tissue. For example, efficacy values yield information regarding a compound's preference for a target tissue by comparing the compound's effect on multiple (e.g., two) tissues. See, for example, Dovey et al., *J. Neurochemistry*, 2001, 76:173-181. Efficacy reflects the ability of compounds to target a specific tissue and create the desired result (e.g., clinically). Efficacious compositions and corresponding methods of treatment are needed to prevent or treat conditions and diseases associated with amyloidosis.

Efficacious compounds of the present invention are those able to decrease the amount of A-beta produced compared to a control, where beta-secretase mediated cleavage is observed and measured in the absence of the compounds. Detection of efficacy can be by analysis of A-beta levels, for example, by immunoassay, fluorometric or chromogenic assay, HPLC, or other means of detection. The efficacy of the compounds of formula (I) was determined as a percentage inhibition corresponding to A-beta concentrations for tissue treated and untreated with a compound of formula (I).

Beta-Secretase

Various forms of beta-secretase enzyme are known, are available, and useful for assaying of enzymatic activity and inhibition of enzyme activity. These include native, recombinant, and synthetic forms of the enzyme. Human beta-secretase is known as Beta Site APP Cleaving Enzyme (BACE), BACE1, Asp2, and memapsin 2, and has been characterized, for example, in U.S. Pat. No. 5,744,346 and published PCT patent applications WO 98/22597, WO 00/03819, WO 01/23533, and WO 00/17369, as well as in literature publications (Hussain et al., 1999, *Mol. Cell. Neurosci.*, 14:419-427; Vassar et al., 1999, *Science*, 286: 735-741; Yan et al., 1999, *Nature*, 402:533-537; Sinha et al., 1999, *Nature*, 40:537-540; and Lin et al., 2000, *Proceedings Natl. Acad. Sciences USA*, 97:1456-1460). Synthetic forms of the enzyme have also been described in, for example (WO 98/22597 and WO 00/17369). Beta-secretase can be extracted and purified from human brain tissue and can be produced in cells, for example mammalian cells expressing recombinant enzyme.

APP Substrate

Assays that demonstrate inhibition of beta-secretase-mediated cleavage of APP can utilize any of the known forms of APP, including the 695 amino acid "normal" isotype described by Kang et al., 1987, *Nature*, 325:733-6, the 770 amino acid isotype described by Kitaguchi et. al., 1981, *Nature*, 331:530-532, and variants such as the Swedish Mutation (KM670-1NL) (APP-SW), the London Mutation (V7176F), and others. See, for example, U.S. Pat. No. 5,766,846 and also Hardy, 1992, *Nature Genet.* 1:233-234, for a review of known variant mutations. Additional useful substrates include the dibasic amino acid modification, APP-KK, disclosed, for example, in WO 00/17369, fragments of APP, and synthetic peptides containing the beta-secretase cleavage site, wild type (WT) or mutated form, (e.g., SW), as described, for example, in U.S. Pat. No. 5,942,400 and WO 00/03819.

The APP substrate contains the beta-secretase cleavage site of APP (KM-DA, SEQ ID NO: 1 or NL-DA, SEQ ID NO: 2) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety can be an antigenic epitope for antibody binding, a label or other detection moiety, a binding substrate, and the like.

Antibodies

Products characteristic of APP cleavage can be measured by immunoassay using various antibodies, as described, for example, in Pirttila et al., 1999, *Neuro. Lett.*, 249:21-4, and in U.S. Pat. No. 5,612,486. Useful antibodies to detect A-beta include, for example, the monoclonal antibody 6E10 (Senetek, St. Louis, Mo.) that specifically recognizes an epitope on amino acids 1-16 of the A-beta peptide, antibodies 162 and 164 (New York State Institute for Basic Research, Staten Island N.Y.) that are specific for human A-beta 1-40 and 1-42, respectively, and antibodies that recognize the junction region of A-beta, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the present invention are described, for example, in WO 00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beta-secretase cleavage site of APP, for example, a complete APP or variant, an APP fragment, or a recombinant or synthetic APP substrate containing the amino acid sequence KM-DA (SEQ ID NO: 1) or NL-DA (SEQ ID NO: 2) is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that can be fusion proteins or peptides that contain the substrate peptide and a modification useful to facilitate the purification or detection of the peptide or its beta-secretase cleavage products. Useful modifications include the insertion of a known antigenic epitope for antibody binding, the linking of a label or detectable moiety, the linking of a binding substrate, and the like.

Suitable incubation conditions for a cell-free in vitro assay include, for example, approximately 200 nM to 10 μM substrate, approximately 10 pM to 200 pM enzyme, and approximately 0.1 nM to 10 μM inhibitor compound, in aqueous solution, at an approximate pH of 4-7, at approximately 37° C., for a time period of approximately 10 min to 3 h. These incubation conditions are exemplary only, and can vary as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by an anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A-beta. Contact of an APP substrate with a beta-secretase enzyme within the cell and in the presence or absence of a compound inhibitor of the present invention can be used to demonstrate beta-secretase inhibitory activity of the compound. It is preferred that the assay in the presence of a useful inhibitory compound provides at least about 10% inhibition of the enzymatic activity, as compared with a non-inhibited control.

In an embodiment, cells that naturally express beta-secretase are used. Alternatively, cells are modified to express a recombinant beta-secretase or synthetic variant enzyme as discussed above. The APP substrate can be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A-beta from APP provide useful means to assay inhibitory activities of the compounds employed in the methods of treatment of the present invention. Production and release of A-beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of at least one cleavage product of the APP substrate. For example, inhibition of beta-secretase activity against the substrate APP would be expected to decrease the release of specific beta-secretase induced APP cleavage products such as A-beta.

Although both neural and non-neural cells process and release A-beta, levels of endogenous beta-secretase activity are low and often difficult to detect by EIA. The use of cell types known to have enhanced beta-secretase activity, enhanced processing of APP to A-beta, and/or enhanced production of A-beta are therefore preferred. For example, transfection of cells with the Swedish Mutant form of APP (APP-SW), with APP-KK, or with APP-SW-KK provides cells having enhanced beta-secretase activity and producing amounts of A-beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor employed in the methods of treatment, the amount of A-beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release A-beta, as described above. For example, transgenic animals expressing APP substrate and beta-secretase enzyme can be used to demonstrate inhibitory activity of the compounds of the present invention. Certain transgenic animal models have been described, for example, in U.S. Pat. Nos. 5,877, 399, 5,612,486, 5,387,742, 5,720,936, 5,850,003, 5,877,015, and 5,811,633, and in Games et al., 1995, *Nature,* 373:523. Animals that exhibit characteristics associated with the pathophysiology of Alzheimer's disease are preferred. Administration of the compounds of the present invention to the transgenic mice described herein provides an alternative method for demonstrating the inhibitory activity of the compounds. Administration of the compounds of the present invention in a pharmaceutically effective carrier and via an administrative route that reaches the target tissue in an appropriate therapeutic amount is also preferred.

Inhibition of beta-secretase mediated cleavage of APP at the beta-secretase cleavage site and of A-beta release can be analyzed in these animals by measuring cleavage fragments in the animal's body fluids such as cerebral fluid or tissues. Analysis of brain tissues for A-beta deposits or plaques is preferred.

A: Enzyme Inhibition Assay

The methods of treatment and compounds of the present invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et al., 1999, Nature, 40:537-540 or recombinantly produced as the full-length enzyme (amino acids 1-501), and can be prepared, for example, from 293 cells expressing the recombinant cDNA, as described in WO 00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu596 at the substrate's APP-SW 751 mutation site.

Specific Assay Procedure

Compounds of formula (I) are diluted in a 1:1 dilution series to a six-point concentration curve (two wells per concentration) in one row of a 96-well plate per compound tested. Each of the test compounds is prepared in DMSO to make up a 10 mM stock solution. The stock solution is serially diluted in DMSO to obtain a final compound concentration of 200 µM at the high point of a 6-point dilution curve. Ten (10) µL of each dilution is added to each of two wells on row C of a corresponding V-bottom plate to which 190 µL of 52 mM NaOAc, 7.9% DMSO, pH 4.5 are pre-added. The NaOAc diluted compound plate is spun down to pellet precipitant and 20 µL/well is transferred to a corresponding flat-bottom plate to which 30 µL of ice-cold enzyme-substrate mixture (2.5 µL MBP-C125SW substrate, 0.03 µL enzyme and 24.5 µL ice cold 0.09% TX100 per 30 µL) is added. The final reaction mixture of 200 µM compound at the highest curve point is in 5% DMSO, 20 µM NaOAc, 0.06% TX100, at pH 4.5.

Warming the plates to 37° C. starts the enzyme reaction. After 90 min at 37° C., 200 µL/well cold specimen diluent is added to stop the reaction and 20 µL/well was transferred to a corresponding anti-MBP antibody coated ELISA plate for capture, containing 80 µL/well specimen diluent. This reaction is incubated overnight at 4° C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a 50% reduction in detected signal ($IC_{50}$) compared to the enzyme reaction signal in the control wells with no added compound. In this assay, preferred compounds of the present invention exhibit an $IC_{50}$ of less than 50 µM.

B: FP BACE Assay: Cell Free Inhibition Assay Utilizing a Synthetic APP Substrate A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds employed in the present invention. Useful substrates include Biotin-SEVNL-DAEFRC[oregon green]KK (SEQ ID NO: 3), Biotin-SEVKM-DAEFRC[oregon green]KK (SEQ ID NO: 4), Biotin-GLNIKTEEISEISY-EVEFRC[oregon green]KK (SEQ ID NO: 5), Biotin-ADRGLTTRPGSGLTNIKTEEISEVNL-DAEFRC[oregon green]KK (SEQ ID NO: 6), and Biotin-FVNQHLCoxGSHLVEALY-LVCoxGERGFFYT-PKAC[oregon green]KK (SEQ ID NO: 7).

The enzyme (0.1 nM) and test compounds (0.001-100 µM) are incubated in pre-blocked, low affinity, black plates (384 well) at 37° C. for 30 min. The reaction is initiated by addition of 150 mM substrate to a final volume of 30 µL/well. The final assay conditions are 0.001-100 µM compound inhibitor, 0.1 molar sodium acetate (pH 4.5), 150 nM substrate, 0.1 nM soluble beta-secretase, 0.001% Tween 20, and 2% DMSO. The assay mixture is incubated for 3 h at 37° C., and the reaction is terminated by the addition of a saturating concentration of immunopure streptavidin. After incubation with streptavidin at room temperature for 15 min, fluorescence polarization is measured, for example, using a LJL Acqurest (Ex485 nm/Em530 nm).

The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, preferred compounds of the present invention exhibit an $IC_{50}$ of less than 50 µM. More preferred compounds of the present invention exhibit an $IC_{50}$ of less than 10 µM. Even more preferred compounds of the present invention exhibit an $IC_{50}$ of less than 5 µM.

C: Beta-Secretase Inhibition: P26-P4'SW Assay

Synthetic substrates containing the beta-secretase cleavage site of APP are used to assay beta-secretase activity, using the methods described, for example, in published PCT application WO 00/47618. The P26-P4'SW substrate is a peptide of the sequence (biotin)CGGADRGLTTRPGSGLT-NIKTEEISEVNLDAEF (SEQ ID NO: 8). The P26-P1 standard has the sequence (biotin)CGGADRGLTTRPGSGLT-NIKTEEISEVNL (SEQ ID NO: 9).

Briefly, the biotin-coupled synthetic substrates are incubated at a concentration of from about 0 to about 200 µM in this assay. When testing inhibitory compounds, a substrate concentration of about 1.0 µM is preferred. Test compounds diluted in DMSO are added to the reaction mixture, with a final DMSO concentration of 5%. Controls also contain a final DMSO concentration of 5%. The concentration of beta secretase enzyme in the reaction is varied, yielding product concentrations with the linear range of the ELISA assay, about 125 to 2000 pM, after dilution.

The reaction mixture also includes 20 mM sodium acetate, pH 4.5, 0.06% Triton X100, and is incubated at 37° C. for about 1 to 3 h. Samples are then diluted in assay buffer (for example, 145.4 nM sodium chloride, 9.51 mM sodium phosphate, 7.7 mM sodium azide, 0.05% Triton X405, 6 g/L bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 h at 4° C. After washing in TTBS buffer (150 mM sodium chloride, 25 mM Tris, 0.05% Tween 20, pH 7.5), the samples are incubated with streptavidin-AP according to the manufacturer's instructions. After a 1 h incubation at room temperature, the samples are washed in TTBS and incubated with fluorescent substrate solution A (31.2 g/L 2-amino-2-methyl-1-propanol, 30 mg/L, pH 9.5). Reaction with streptavidin-alkaline phosphate permits detection by fluorescence. Compounds that are effective inhibitors of beta-secretase activity demonstrate reduced cleavage of the substrate as compared to a control.

D: Assays Using Synthetic Oligopeptide-Substrates

Synthetic oligopeptides are prepared incorporating the known cleavage site of beta-secretase, and optionally include detectable tags, such as fluorescent or chromogenic moieties. Examples of such peptides, as well as their production and detection methods, are described in U.S. Pat. No. 5,942,400. Cleavage products can be detected using high performance liquid chromatography, or fluorescent or chromogenic detection methods appropriate to the peptide to be detected, according to methods well known in the art.

By way of example, one such peptide has the sequence SEVNL-DAEF (SEQ ID NO: 10), and the cleavage site is between residues 5 and 6. Another preferred substrate has the sequence ADRGLTTRPGSGLTNIKTEEISEVNL-DAEF (SEQ ID NO: 11), and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of a compound inhibitor to control results provides a measure of the compound's inhibitory activity.

E: Inhibition of Beta-Secretase Activity-Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met652 to Asn651Leu652 (numbered for APP751), commonly called the Swedish mutation and shown to overproduce A-beta (Citron et al., 1992, Nature, 360:672-674), as described in U.S. Pat. No. 5,604,102.

The cells are incubated in the presence/absence of the inhibitory compound (diluted in DMSO) at the desired concentration, generally up to 10 μg/mL. At the end of the treatment period, conditioned media is analyzed for beta-secretase activity, for example, by analysis of cleavage fragments. A-beta can be analyzed by immunoassay, using specific detection antibodies. The enzymatic activity is measured in the presence and absence of the compounds of formula (I) to demonstrate specific inhibition of beta-secretase mediated cleavage of APP substrate.

F: Inhibition of Beta-Secretase in Animal Models of Alzheimer's Disease

Various animal models can be used to screen for inhibition of beta-secretase activity. Examples of animal models useful in the present invention include mouse, guinea pig, dog, and the like. The animals used can be wild type, transgenic, or knockout models. In addition, mammalian models can express mutations in APP, such as APP695-SW and the like as described herein. Examples of transgenic non-human mammalian models are described in U.S. Pat. Nos. 5,604,102, 5,912,410 and 5,811,633.

PDAPP mice, prepared as described in Games et al., 1995, Nature, 373:523-527 are useful to analyze in vivo suppression of A-beta release in the presence of putative inhibitory compounds. As described in U.S. Pat. No. 6,191,166, 4-month-old PDAPP mice are administered a compound of formula (I) formulated in a vehicle, such as corn oil. The mice are dosed with the compound (1-30 mg/mL, preferably 1-10 mg/mL). After a designated time, e.g., 3-10 h, the brains are analyzed.

Transgenic animals are administered an amount of a compound formulated in a carrier suitable for the chosen mode of administration. Control animals are untreated, treated with vehicle, or treated with an inactive compound. Administration can be acute, (i.e. single dose or multiple doses in one day), or can be chronic, (i.e. dosing is repeated daily for a period of days). Beginning at time 0, brain tissue or cerebral fluid is obtained from selected animals and analyzed for the presence of APP cleavage peptides, including A-beta, for example, by immunoassay using specific antibodies for A-beta detection. At the end of the test period, animals are sacrificed and brain tissue or cerebral fluid is analyzed for the presence of A-beta and/or beta-amyloid plaques. The tissue is also analyzed for necrosis.

Reduction of A-beta in brain tissues or cerebral fluids and reduction of beta-amyloid plaques in brain tissue are assessed by administering the compounds of formula (I), or pharmaceutical compositions comprising compounds of formula (I) to animals and comparing the data with that from non-treated controls.

G: Inhibition of A-Beta Production in Human Patients

Patients suffering from Alzheimer's disease demonstrate an increased amount of A-beta in the brain. Alzheimer's disease patients are subjected to a method of treatment of the present invention, (i.e. administration of an amount of the compound inhibitor formulated in a carrier suitable for the chosen mode of administration). Administration is repeated daily for the duration of the test period. Beginning on day 0, cognitive and memory tests are performed, for example, once per month.

Patients administered the compounds of formula (I) are expected to demonstrate slowing or stabilization of disease progression as analyzed by a change in at least one of the following disease parameters: A-beta present in cerebrospinal fluid or plasma; brain or hippocampal volume; A-beta deposits in the brain; amyloid plaque in the brain; or scores for cognitive and memory function, as compared with control, non-treated patients.

H: Prevention of A-Beta Production in Patients at Risk for Alzheimer's Disease

Patients predisposed or at risk for developing Alzheimer's disease can be identified either by recognition of a familial inheritance pattern, for example, presence of the Swedish Mutation, and/or by monitoring diagnostic parameters. Patients identified as predisposed or at risk for developing Alzheimer's disease are administered an amount of the compound inhibitor formulated in a carrier suitable for the chosen mode of administration. Administration is repeated daily for the duration of the test period. Beginning on day 0, cognitive and memory tests are performed, for example, once per month.

Patients subjected to a method of treatment of the present invention (i.e., administration of at least one compound of formula (I)) are expected to demonstrate slowing or stabilization of disease progression as analyzed by a change in at least one of the following disease parameters: A-beta present in cerebrospinal fluid or plasma; brain or hippocampal volume; amyloid plaque in the brain; or scores for cognitive and memory function, as compared with control, non-treated patients.

I: Efficacy of Compounds to Inhibit A-Beta Concentration

The invention encompasses compounds of formula (I) that are efficacious. Efficacy is calculated as a percentage of concentrations as follows:

Efficacy=(1−(total A-beta in dose group/total A-beta in vehicle control))*100% wherein the "total A-beta in dose group" equals the concentration of A-beta in the tissue, (e.g., rat brain) treated with the compound, and the "total A-beta in vehicle control" equals the concentration of A-beta in the tissue, yielding a % inhibition of A-beta production. Statistical significance is determined by p-value<0.05 using the Mann Whitney t-test. See, for example, Dovey et al., *J. Neurochemistry*, 2001, 76:173-181.

Where indicated, diastereomers were separated by reverse phase HPLC using the noted methods. The first isomer collected in each case was designated Diastereomer A, and the second isomer Diastereomer B. Unless otherwise indicated, specific formula (I) compound examples represent mixtures of diastereomers.

J: Selectivity of Compounds for Inhibiting BACE Over Aspartyl Proteases

The compounds of formula (I) can be selective for beta-secretase versus catD. Wherein the ratio of catD:beta-secretase is greater than 1, selectivity is calculated as follows:

Selectivity=(IC$_{50}$ for catD/IC$_{50}$ for beta-secretase) *100% wherein IC$_{50}$ is the concentration of compound necessary to decrease the level of catD or beta-secretase by 50%.

The compounds of formula (I) can be selective for beta-secretase versus catE. Wherein the ratio of catE:beta-secretase is greater than 1, selectivity is calculated as follows:

Selectivity=(IC$_{50}$ for catE/IC$_{50}$ for beta-secretase) *100% wherein IC$_{50}$ is the concentration of compound necessary to decrease the level of catE or beta-secretase by 50%. Selectivity is reported as the ratio of IC$_{50}$(catE):IC$_{50}$(BACE).

Pharmacokinetic parameters were calculated by a non-compartmental approach. See, for example, Gibaldi, M. and Perrier, D., *Pharmacokinetics*, Second Edition, 1982, Marcel Dekker Inc., New York, N.Y., pp 409-418.

EXAMPLE 33

Exemplary Formula (I) Compounds Exhibiting Selectivity for Bace Versus catD

In the following examples, each value is an average of four experimental runs and multiple values for one compound indicate that more than one experiment was conducted.

| Example No. | Compound | Selectivity IC$_{50}$(catD)/ IC$_{50}$(BACE) |
|---|---|---|
| 33-1 | 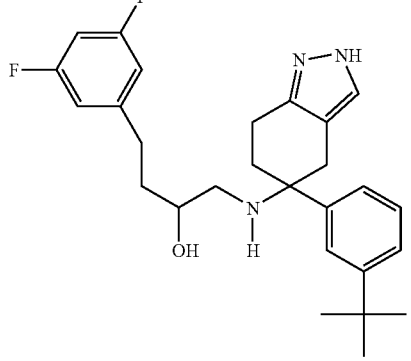 1-(5-(3-tert-butylphenyl)-4,5,6,7-tetrahydro-2H-indazol-5-ylamino)-4-(3,5-difluorophenyl)butan-2-ol | 1.8 >2.4 1.0 |

EXAMPLE 34

Exemplary Formula (I) Compounds Exhibiting Selectivity for Bace Versus catE

| Example No. | Compound | Selectivity IC$_{50}$(catE)/ IC$_{50}$(BACE) |
|---|---|---|
| 34-1 | 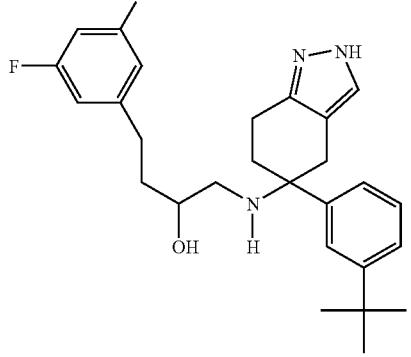 1-(5-(3-tert-butylphenyl)-4,5,6,7-tetrahydro-2H-indazol-5-ylamino)-4-(3,5-difluorophenyl)butan-2-ol | 1.6 1.6 0.6 |

Oral Bioavailability of Compounds for Inhibiting Amyloidosis

The invention encompasses compounds of formula (I) that are orally bioavailable. Generally, oral bioavailability is defined as the fraction of orally administered dose reaching systemic circulation. Oral bioavailability can be determined following both an intravenous (IV) and oral (PO) administration of a test compound.

Oral bioavailability was determined in the male Sprague-Dawley rat following both IV and PO administration of test compound. Two month-old male rats (250-300 g) were surgically implanted with polyethylene (PE-50) cannula in the jugular vein while under isoflurane anesthesia the day before the in-life phase. Animals were fasted overnight with water ad libitum, then dosed the next day. The dosing regime consisted of either a 5 mg/kg (2.5 mL/kg) IV dose (N=3) administered to the jugular vein cannula, then flushed with saline, or a 10 mg/kg (5 mL/kg) PO dose (N=3) by esophageal gavage. Compounds were formulated with 10% Solutol in 5% dextrose at 2 mg/mL. Subsequent to dosing, blood was collected at 0.016 (IV only), 0.083, 0.25, 0.5, 1, 3, 6, 9 and 24 h post administration and heparinized plasma was recovered following centrifugation.

Compounds were extracted from samples following precipitation of the plasma proteins by methanol. The resulting supernatants were evaporated to dryness and reconstituted with chromatographic mobile phase (35% acetonitrile in 0.1% formic acid) and injected onto a reverse phase $C_{18}$ column (2×50 mm, 5 μm, BDS Hypersil). Detection was facilitated with a multi-reaction-monitoring experiment on a tandem triple quadrupole mass spectrometer (LC/MS/MS) following electrospray ionization. Experimental samples were compared to calibration curves prepared in parallel with aged match rat plasma and quantitated with a weighted 1/x linear regression. The lower limit of quantization (LOQ) for the assay was typically 0.5 ng/mL.

Oral bioavailability (% F or F value) is calculated from the dose-normalized ratio of plasma exposure following oral administration to the intravenous plasma exposure in the rat by the following equation $$\% F = (AUC_{po}/AUC_{iv}) \times (D_{iv}/D_{po}) \times 100\%$$

where D is the dose and AUC is the area-under-the-plasma-concentration-time-curve from 0 to 24 h. AUC is calculated from the linear trapezoidal rule by $AUC=((C_2+C_1)/2)\times(T_2-T_1)$ where C is concentration and T is time.

Pharmacokinetic parameters were calculated by a non-compartmental approach. See, for example, Gibaldi, M. and Perrier, D., *Pharmacokinetics*, Second Edition, 1982, Marcel Dekker Inc., New York, N.Y., pp 409-418.L: Brain Uptake The invention encompasses beta-secretase inhibitors that can readily cross the blood-brain barrier. Factors that affect a compound's ability to cross the blood-brain barrier include a compound's molecular weight, Total Polar Surface Area (TPSA), and log P (lipophilicity). See, e.g., Lipinski, C. A., et al., *Adv. Drug Deliv. Reviews*, 23:3-25 (1997). One of ordinary skill in the art will be aware of methods for determining characteristics allowing a compound to cross the blood-brain barrier. See, for example, Murcko et al., *Designing Libraries with CNS Activity, J. Med. Chem.*, 42 (24), pp. 4942-51 (1999). Calculations of logP values were performed using the Daylight clogP program (Daylight Chemical Information Systems, Inc.). See, for example, Hansch, C., et al., *Substituent Constants for Correlation Analysis in Chemistry and Biology*, Wiley, New York (1979); Rekker, R., *The Hydrophobic Fragmental Constant*, Elsevier, Amsterdam (1977); Fujita, T., et al., *J. Am. Chem. Soc.*, 86, 5157 (1964). TPSA was calculated according to the methodology outlined in Ertl, P., et al., *J. Med. Chem.*, 43:3714-17 (2000).

The following assay was employed to determine the brain penetration of compounds encompassed by the present invention.

In-life phase: Test compounds were administered to CF-1 (20-30 g) mice at 10 μmol/kg (4 to 7 mg/kg) following IV administration in the tail vein. Two time-points, 5 and 60 min, are collected post dose. Four mice are harvested for heparinized plasma and non-perfused brains at each time-point for a total of 8 mice per compound.

Analytical phase: Samples were extracted and evaporated to dryness, then reconstituted and injected onto a reverse phase chromatographic column while monitoring the effluent with a triple quadrupole mass spectrometer. Quantitation was then performed with a $1/x^2$ weighted fit of the least-squares regression from calibration standards prepared in parallel with the in vivo samples. The LOQ is generally 1 ng/mL and 0.5 ng/g for the plasma and brain respectively. Data was reported in micromolar (μM) units. Brain levels were corrected for plasma volumes (16 μL/g).

Results: Comparison of a compound's brain concentration level to two marker compounds, Indinavir and Diazepam, demonostrates the ability in which the compounds of the present invention can cross the blood-brain barrier. Indinavir (HIV protease inhibitor) is a poor brain penetrant marker and Diazepam is a blood flow limited marker. The concentration levels of Indinavir in the brain at 5 and 60 min were 0.165 μM and 0.011 μM, respectively. The concentration levels of Diazepam at 5 and 60 min were 5.481 μM and 0.176 μM, respectively.

The present invention has been described with reference to various specific and preferred embodiments and techniques. However, it should be understood that many variations and modifications may be made while remaining within the spirit and scope of the present invention.

Unless defined otherwise, all scientific and technical terms used herein have the same meaning as commonly understood by one of skill in the art to which this invention belongs. Although methods and materials similar or equivalent to those described herein can be used in the practice or testing of the present invention, suitable methods and materials are described above. Additionally, the materials, methods, and examples are illustrative only and not intended to be limiting. All publications, patent applications, patents, and other references mentioned herein are incorporated by reference in their entirety. In case of conflict, the present specification, including definitions, will control.

What is claimed is:

1. A compound of formula (I),

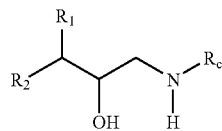

(I)

or at least one pharmaceutically acceptable salt thereof, wherein $R_1$ is selected from

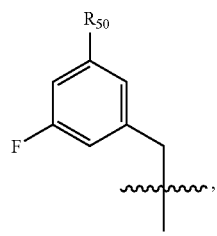

(IIa)

-continued

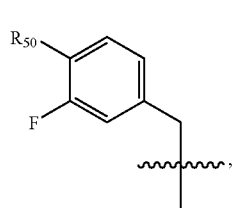
(IIb)

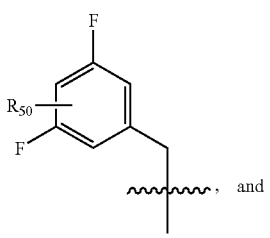
(IIc)
, and

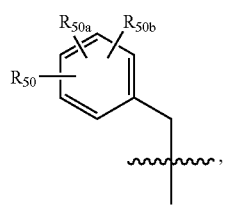
(IId)
, $R_{50}$, $R_{50a}$, and $R_{50b}$ are independently selected from —H, halogen, —OH, —SH, —CN, —C(O)-alkyl, —NR$_7$R$_8$, —NO$_2$, —S(O)$_{0-2}$-alkyl, alkyl, alkoxy, —O-benzyl (optionally substituted with at least one group independently selected from —H, —OH, and alkyl), —C(O)—NR$_7$R$_8$, alkyloxy, alkoxyalkoxy-alkoxy, and cycloalkyl;
  wherein the alkyl, alkoxy, and cycloalkyl groups within $R_{50}$, $R_{50a}$, and $R_{50b}$ are optionally substituted with at least one group independently selected from alkyl, halogen, OH, NR$_5$R$_6$, CN, haloalkoxy, NR$_7$R$_8$, and alkoxy;
$R_5$ and $R_6$ are independently selected from —H and alkyl, or
$R_5$ and $R_6$, and the nitrogen to which they are attached, form a 5 or 6 membered heterocycloalkyl ring; and
$R_7$ and $R_8$ are independently selected from —H, alkyl optionally substituted with at least one group independently selected from —OH, —NH$_2$, and halogen, -cycloalkyl, and -alkyl-O-alkyl;
$R_2$ is selected from
  —H,
  -alkyl optionally substituted with at least one group independently selected from $R_{200}$,
  —OH,
  —O-alkyl optionally substituted with at least one group independently selected from $R_{200}$,
  —C(O)—N(R$_{315}$)(R$_{320}$), wherein R$_{315}$ and R$_{320}$ are each independently selected from —H, alkyl, and aryl,
  —NH—R$_{400}$, and
  —R$_{400}$ $R_{400}$ is

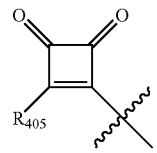

wherein $R_{405}$ is selected from —H, —N(R$_{515}$)$_2$ and O-alkyl;
$R_{515}$ is independently selected from
  —H,
  -alkyl, and
  -aryl;
$R_C$ is selected from formula

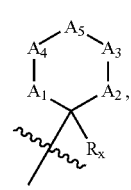
(IIId)

wherein,
$A_1$ and $A_2$ are independently selected from —(CH$_2$)$_{0-2}$—, —CH(R$_{200}$)—, —C(R$_{200}$)$_2$—, —C(=N—R$_{230}$)—, —C(=CH—R$_{230}$)—, —C(=N—C(O)—R$_{230}$)—, and —C(=CH—C(O)—R$_{230}$)—;
$A_3$, $A_4$, and $A_5$ are independently selected from —CH$_2$—, —CH(R$_{200}$)—, —C(R$_{200}$)$_2$—, —C(O)—, —C(=N—R$_{230}$)—, —C(=N—NH(alkyl))-, —C(=N—N(alkyl)(alkyl))-, —C(=N—O—(CH$_2$)$_{1-4}$—OH)—, —C(=CH—R$_{230}$), —C(=N—C(O)—R$_{230}$)—, and —C(=CH—C(O)—R$_{230}$)—;
$R_{230}$ is independently selected from —H, —OH, R$_{215}$ (optionally substituted with —OH, —NH$_2$, —C(O)H, and —CN), alkyl, cycloalkyl, alkoxy, -alkyl-OH, -alkyl-NH$_2$, -alkyl-C(O)H, —O—R$_{215}$ (optionally substituted with —OH, —NH$_2$, —C(O)H, and —CN), —O-alkyl, —O-alkyl-OH, —O-alkyl-NH$_2$, —O-alkyl-C(O)H, —NH$_2$, —NHR$_{215}$, —N(R$_{215}$)$_2$, —NR$_{235}$R$_{240}$, and —CN;
  wherein at least one carbon of the alkyl or cycloalkyl within $R_{230}$ is optionally independently replaced with —C(O)— or a heteroatom;
  wherein the cycloalkyl within formulae (IIId) may optionally contain at least one double bond;
  wherein in formulae (IIId), only one of $A_1$, $A_2$, $A_3$, $A_4$, or $A_5$ is selected from —C(=N—R$_{230}$)—, —C(=N—NH(alkyl))-, —C(=N—N(alkyl)(alkyl))-, C(=N—O—(CH$_2$)$_{1-4}$—OH)—, —C(=CH—R$_{230}$)-r-C(=N—C(O)—R$_{230}$)—, and —C(=CH—C(O)—R$_{230}$)—;
  wherein each aryl group attached directly or indirectly to $R_C$ is optionally substituted with at least one group independently selected from $R_{200}$;
  wherein each cycloalkyl or attached directly or indirectly to $R_C$ is optionally substituted with at least one group independently selected from $R_{210}$; and
$R_x$ is selected from aryl, and cycloalkyl;
  wherein each aryl group of $R_x$ is optionally substituted with at least one group independently selected from $R_{200}$;

wherein each cycloalkyl of $R_x$ is optionally substituted with at least one group independently selected from $R_{210}$, and
$R_{200}$ at each occurrence is independently selected from
-alkyl optionally substituted with at least one group independently selected from $R_{205}$,
—$(CH_2)_{0-4}$—C(O)H,
—$(CO)_1R_{215}$,
—$(CO)_1R_{220}$,
—$(CH_2)_{0-4}$—$(CO)_{0-1}$—$NR_{220}R_{225}$,
—$(CH_2)_{0-4}$—$(CO)_{0-1}$—NH($R_{215}$),
—$(CH_2)_{0-4}$—C(O)-alkyl
—$(CH_2)_{0-4}$—$(CO)_{0-1}$-cycloalkyl,
—$(CH_2)_{1-4}$—$(CO)_{0-1}$-heterocycloalkyl,
—$(CH_2)_{0-4}$—$(CO)_{0-1}$-aryl,
—$(CH_2)_{1-4}$—$(CO)_{0-1}$-heteroaryl,
—$(CH_2)_{0-4}$—C(O)—O—$R_{215}$,
—$(CH_2)_{0-4}$—$SO_2$—$NR_{220}R_{225}$,
—$(CH_2)_{0-4}$—$S(O)_{0-2}$-alkyl,
—$(CH_2)_{0-4}$—$S(O)_{0-2}$-cycloalkyl,
—$(CH_2)_{0-4}$—N(H or $R_{215}$)—C(O)—O—$R_{215}$,
—$(CH_2)_{0-4}$—N(H or $R_{215}$)—$SO_2$—$R_{220}$,
—$(CH_2)_{0-4}$—N(H or $R_{215}$)—C(O)—N($R_{215}$)$_2$,
—$(CH_2)_{0-4}$—N(H or $R_{215}$)—C(O)—$R_{220}$,
—$(CH_2)_{0-4}$—C(O)-alkyl
—$(CH_2)_{0-4}$—O—($R_{215}$),
—$(CH_2)_{0-4}$—S—($R_{215}$), and
—$(CH_2)_{0-4}$—O-alkyl optionally substituted with at least one halogen;
wherein each aryl and heteroaryl group included within $R_{200}$ is optionally substituted with at least one group independently selected from $R_{205}$, $R_{210}$, and alkyl (optionally substituted with at least one group independently selected from $R_{205}$ and $R_{210}$);
wherein each cycloalkyl or heterocycloalkyl group included within $R_{200}$ is optionally substituted with at least one group independently selected from $R_{210}$;
$R_{205}$ at each occurrence is independently selected from
-alkyl,
-haloalkoxy,
—$(CH_2)_{0-3}$-cycloalkyl,
-halogen,
—$(CH_2)_{1-6}$—OH,
—O-aryl,
—OH,
—SH,
—$(CH_2)_{0-4}$—(O)H,
—$(CH_2)_{0-6}$—CN,
—$(CH_2)_{0-6}$—C(O)—$NR_{235}R_{240}$,
—$(CH_2)_{0-6}$—C(O)—$NR_{235}$,
—$(CH_2)_{0-4}$—N(H or $R_{215}$)—$SO_2$—$R_{235}$,
—$OCF_3$,
—$CF_3$,
-alkoxy,
-alkoxycarbonyl, and
—$NR_{235}R_{240}$; $R_{210}$ at each occurrence is independently selected from
—$(CH_2)_{0-4}$—OH,
—$(CH_2)_{0-4}$—CN,
—$(CH_2)_{0-4}$—C(O)H,
-alkyl optionally substituted with at least one group independently selected from $R_{205}$,
-alkanoyl,
—S-alkyl;
—$S(O)_2$-alkyl,
-halogen,
-alkoxy,
—$(CH_2)_{0-4}$—$NR_{235}R_{240}$,
—$(CH_2)_{0-4}$—$NR_{235}$(alkoxy),
—$(CH_2)_{0-4}$—S—($R_{215}$),
—$(CH_2)_{0-4}$—$NR_{235}$—C(O)H,
—$(CH_2)_{0-4}$—$NR_{235}$—C(O)-(alkoxy),
—$(CH_2)_{0-4}$—$NR_{235}$—C(O)—$R_{240}$,
—C(O)—$NHR_{215}$,
—C(O)-alkyl,
—C(O)—$NR_{235}R_{240}$, and
$R_{215}$ at each occurrence is independently selected from
-alkyl,
—$(CH_2)_{0-2}$-aryl,
—$(CH_2)_{0-2}$-cycloalkyl,
—$(CH_2)_{0-2}$-heteroaryl,
—$(CH_2)_{0-2}$-heterocycloalkyl, and
—$CO_2$—$CH_2$-aryl;
wherein the aryl group included within $R_{215}$ is optionally substituted with at least one group independently selected from $R_{205}$ and $R_{210}$, and
wherein the heterocycloalkyl and heteroaryl groups included within $R_{215}$ are optionally substituted with at least one group independently selected from $R_{210}$;
$R_{220}$ and $R_{225}$ at each occurrence are independently selected from
—H,
-alkyl,
—$(CH_2)_{0-4}$—C(O)H,
-alkylhydroxyl,
-alkoxycarbonyl,
-alkylamino,
—$S(O)_2$-alkyl,
-alkanoyl optionally substituted with at least one halogen,
—C(O)—$NH_2$,
—C(O)—NH(alkyl),
—C(O)—N(alkyl)(alkyl),
-haloalkyl,
—$(CH_2)_{0-2}$-cycloalkyl,
-(alkyl)-O-(alkyl),
-aryl,
-heteroaryl, and
-heterocycloalkyl;
wherein the aryl, heteroaryl, cycloalkyl, and heterocycloalkyl groups included within $R_{220}$ and $R_{225}$ are each optionally substituted with at least one group independently selected from $R_{270}$;
$R_{270}$ at each occurrence is independently selected from
—$R_{205}$,
-alkyl optionally substituted with at least one group independently selected from $R_{205}$,
-aryl,
-halogen,
-alkoxy,
-haloalkoxy,
—$NR_{235}R_{240}$,
—OH,
—CN,
-cycloalkyl optionally substituted with at least one group independently selected from $R_{205}$,
—C(O)-alkyl,
—$S(O)_2$—$NR_{235}R_{240}$,
—C(O)—$NR_{235}R_{240}$,
—$S(O)_2$-alkyl, and
—$(CH_2)_{0-4}$—C(O)H;

R₂₃₅ and R₂₄₀ at each occurrence are independently selected from
—H,
—OH,
—CF₃,
—OCH₃,
—NHCH₃,
—N(CH₃)₂,
—(CH₂)₀₋₄—C(O)(H or alkyl),
-alkyl,
-alkanoyl,
—SO₂-alkyl, and
-aryl.

2. The compound according to claim 1, wherein R₁ is optionally substituted with at least one group independently selected from halogen, C₁-C₂ alkyl, C₁-C₂ alkoxy, and —OH.

3. The compound according to claim 1, wherein R₁ is selected from 3-allyloxy-5-fluoro-benzyl, 3-benzyloxy-5-fluoro-benzyl, 4-hydroxy-benzyl, 3-hydroxybenzyl, 3,5-difluoro-2-propylamino-benzyl, 2-ethylamino-3,5-difluoro-benzyl, 2-hydroxy-5-methyl-benzamide, 3-fluoro-5-[2-(2-methoxy-ethoxy)-ethoxy]-benzyl, 3-fluoro-5-heptyloxybenzyl, 3-fluoro-5-hexyloxy-benzyl, 4-hydroxybenzyl, 3-hydroxy-benzyl, 3,5-difluoro-2-hydroxy-benzyl, 3,5-difluoro-4-hydroxy-benzyl, 3,5-difluoro-benzyl, 3-fluoro-4-hydroxy-benzyl, 3-fluoro-5-hydroxy-benzyl, and 3-fluorobenzyl.

4. The compound according to claim 1, wherein R₂ is selected from hydrogen, 3-4-dioxo-cyclobut-1-enylamino, 2-methoxy-3-4-dioxo-cyclobut-1-enylamino, and 2-methylamino-3,4-dioxo-cyclobut-1-enylamino.

5. The compound according to claim 1, wherein R_C is selected from

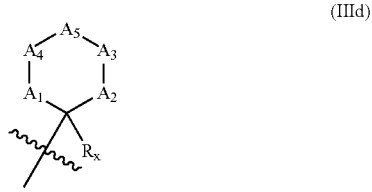

(IIId)

wherein A₅ is —C(=N—R₂₃₀) and A₁, A₂, A₃, A₄, R_x and R₂₃₀ are defined as in claim 1.

6. The compound according to claim 5, wherein A₅ is selected from —C(=N—OH)—, —C(=N—O—CH₃)—, —C(=N—O—CH₂CH₃)—, —C(=N—O—CH₂CH₂OH)—, —C(=N—O—CH₂CH₂NH₂)—, —C(=N—NHCH₃)—, and —C(=N—CN)—, and A₁, A₂, A₃, and A₄ are —CH₂—.

7. The compound according to claim 1, wherein R_C is selected from 1-(3-tert-Butyl-phenyl)-4-hydroxyimino-cyclohexyl, 1-(3-tert-Butyl-phenyl)-4-methoxyiminocyclohexyl, 1-(3-tert-Butyl-phenyl)-4-ethoxyimino-cyclohexyl, 1-(3-tert-Butyl-phenyl)-4-(2-hydroxy-ethoxyimino)-cyclohexyl, 1-(3-tert-Butyl-phenyl)-4-(2-amino-ethoxyimino)-cyclohexyl, 1-(3-tert-Butyl-phenyl)-4-(methyl-hydrazono)-cyclohexyl, 1-(3-tert-Butyl-phenyl)-4-cyanoiminocyclohexyl, 1-(Acrylic acid methyl ester)-4-(tert-Butyl-phenyl)-cyclohexane-4-yl, 1-(Acrylamide)-4-(tert-Butyl-phenyl)-cyclohexane-4-yl, 1-(3-tert-Butyl-phenyl)-4-(2-hydroxy-ethylidene)-cyclohex-1-yl, 1-(3-tert-Butyl-phenyl)-4-(methyl-hydrazono)-cyclohex-1-yl, 1(3-tert-Butyl-phenyl)-4-(dimethyl-hydrazono)-cyclohex-1-yl, 4-methoxyimino-1-(3-thiophen-3-yl-phenyl)-cyclohexyl, 1-(3-furan-3-ylphenyl)-4-methoxyimino-cyclohexyl, 4-methoxyimino-1-[3-(1H-pyrrol-2-yl)-phenyl]cyclohexyl, 4-methoxyimino-1-(3-pyridin-4-yl-phenyl)-cyclohexyl, 4-methoxyimino-1-(3-pyrimidin-5-yl-phenyl)-cyclohexyl, 4-methoxyimino-1-(3-pyrazol-1-yl-phenyl)-cyclohexyl, 1-(3-tert-Butylphenyl)-4-methylene-cyclohexyl, and ethyl 2-(4-(3tert-butylphenyl)cyclohexylidene)acetate.

8. The compound according to claim 1, wherein R_x is selected from 3-(1,1-dimethyl-propyl)-phenyl, 3-(1-ethyl-propyl)-phenyl, 3-(1-hydroxy-1-methyl-ethyl)-phenyl, 3-(1-methylcyclopropyl)-phenyl, 3-(2,2-dimethyl-propyl)-phenyl, 3-(2-fluoro-benzyl)-phenyl, 3-(3-methyl-butyl)-phenyl, 3-(4-fluoro-benzyl)-phenyl, 3-(Cyano-dimethyl-methyl)-phenyl, 3-Acetyl-5-tert-butyl-phenyl, 3'-Acetylamino-biphenyl-3-yl, 3-Bromo-5-tert-butyl-phenyl, 3-Cyano-phenyl, 3-Cyclobutyl-phenyl, 3-Cyclopentyl-phenyl, 3-Cyclopropyl-phenyl, 3-ethyl-phenyl, 3-ethynyl-phenyl, 3-fluoro-5-(2-hydroxy-1,1-dimethyl-ethyl)-phenyl, 3-isobutyl-phenyl, 3-isopropyl-phenyl, 3-pent-4-enyl-phenyl, 3-pentyl-phenyl, 3-Phenyl-propionic acid ethyl ester, 3-sec-Butyl-phenyl, 3-tert-Butyl-4-chloro-phenyl, 3-tert-Butyl-4-cyano-phenyl, 3-tert-Butyl-4-ethyl-phenyl, 3-tert-Butyl-4-methyl-phenyl, 3-tert-Butyl-4-trifluoromethyl-phenyl, 3-tert-Butyl-5-chloro-phenyl, 3-tert-Butyl-5-cyano-phenyl, 3-tert-Butyl-5-ethyl-phenyl, 3-tert-Butyl-5-fluoro-phenyl, 3-tert-Butyl-5-methyl-phenyl, 3-tert-Butyl-5-trifluoromethyl-phenyl, 3-tert-Butyl-phen-1-yl, 3-tert-Butyl-phenyl, 3-trifluoromethyl-phenyl, and 4-Acetyl-3-tert-butyl-phenyl.

9. The compound according to claim 1, wherein R_x is 3-tert-Butyl-phen-1-yl.

10. The compound according to claim 1, wherein the formula (I) compound is selected from 4-[1-(3-tert-Butyl-phenyl)-4-hydroxyimino-cyclohexylamino]-2-(3,5-difluoro-benzyl)-3-hydroxy-N-methyl-butyramide, 4-[1-(3-tert-Butyl-phenyl)-4-methoxyimino-cyclohexylamino]-2-(3,5-difluoro-benzyl)-3-hydroxy-N-methyl-butyramide, 4-[1-(3-tert-Butyl-phenyl)-4-ethoxyimino-cyclohexylamino]-2-(3,5-difluoro-benzyl)-3-hydroxy-N-methyl-butyramide, 4-[1-(3-tert-Butyl-phenyl)-4-(2-hydroxy-ethoxyimino)-(cyclohexylamino]-2-(3,5-difluoro-benzyl)-3-hydroxy-N-methyl-butyramide, 4-[4-(2-Amino-ethoxyimino)-1-(3-tert-butyl-phenyl)-cyclohexylamino]-2-(3,5-difluoro-benzyl)-3-hydroxy-N-methyl-butyramide, 4-[1-(3-tert-Butyl-phenyl)-4-(methyl-hydrazono)-cyclohexylamino]-2-(3,5-difluoro-benzyl)-3-hydroxy-N-methyl-butyramide, 4-[1-(3-tert-Butyl-phenyl)-4-(dimethyl-hydrazono)-cyclohexylamino]-2-(3,5-difluoro-benzyl)-3-hydroxy-N-methyl-butyramide, 4-[1-(3-tert-Butyl-phenyl)-4-cyanoimino-cyclohexylamino]-2(3,5-difluoro-benzyl)-3-hydroxy-N-methyl]-butyramide, 4-[1-(3-tert-Butyl-phenyl)-4-methylcarbamoyl methylene-cyclohexylamino]-2-(3,5-difluoro-benzyl)-3-hydroxy-N-methyl-butyramide, {4-(3-tert-Butyl-phenyl)-4-[4-(3,5-difluoro-phenyl)-2-hydroxy-3-methylcarbamoyl-butylamino]-cyclohexylidene}-acetic acid methyl ester, 4-[1-(3-tert-Butyl-phenyl)-4-(2-hydroxy-ethylidene)-cyclohexylamino]-2-(3,5-difluoro-benzyl)-3-hydroxy-N-methyl-butyramide, 4-[1-(3-tert-Butyl-phenyl)-4-hydroxyimino-cyclohexylamino]-2-(3,5-difluoro-benzyl)-3-hydroxy-N-phenyl-butyramide, 4-[1-(3-tert-Butyl-phenyl)-4-methoxyimino-cyclohexylamino]-2-(3,5-difluoro-benzyl)-3-hydroxy-N-phenyl-butyramide, 4-[1(3-tert-Butyl-phenyl)-4-ethoxyimino-cyclohexylamino]-2-(3,5-difluoro-benzyl)-3-hydroxy-N-phenyl-butyramide, 4-[1-(3-tert-Butyl-phenyl)-4-(2-hydroxy-ethoxyimino)-cyclohexylamino]-2-(3,5-difluoro-benzyl)-3-hydroxy-N-phenyl-butyramide, 4-[4-(2-Amino-ethoxyimino)-1-(3-tertbutyl-phenyl)-cyclohexylamino)-2-(3,5-difluoro-benzyl)-3-hydroxy-N-phenyl-butyramide, 4-[1-(3-tert-Butyl-phenyl)-4-(methyl-hydrazono)-cyclohexylamino]-2-(3,5-difluoro-benzyl)-3-hydroxy-N-phenyl-butyramide, 4-[1-(3-tert-Butyl-phenyl)-4-(dimethyl-hydrazono)-cyclohexylamino]-2-(3,5-difluoro-benzyl)-3-hydroxy-N-phenyl-butyramide, 4-[1-(3-tert-Butyl-phenyl)-4-cyanoimino-cyclohexylamino]-2-(3,5-difluoro-benzyl)-3-hydroxy-N-phenyl-butyramide, 4-[1-(3-tert-Butyl-phenyl)-4-methylcarbamoyl methylene-cyclohexylamino]-2-(3,5-difluoro-benzyl)-3-hydroxy-N-phenyl-butyramide, {4-(3-tert-Butyl-phenyl)-4-[(3,5-difluoro-phenyl)-2-hydroxy-3-phenylcarbamoyl-butylamino]-cyclohexylidene)-acetic acid methyl ester, 4-[1-(3-tert-Butyl-phenyl)-4-(2-hydroxyethylidene)-cyclohexylamino]-2-(3,5-difluoro-benzyl)-3-hydroxy-N-phenyl-butyramide, 4-(3-tert-Butyl-phenyl)-4-[(3,5-difluoro-phenyl)-2-hydroxy-butylamino]-cyclohexanone oxime, 4-(3-tert-Butyl-phenyl)-4-[3-(3,5-difluorophenoxy)-2-hydroxy-propylamino]-cyclohexanone oxime, 4-(3-tert-Butyl-phenyl)-4-[4-(3,5-difluoro-phenyl)-2-hydroxy-4-oxo-butylamino]-cyclohexanone oxime, 4-(3-tert-Butyl-phenyl)-4-[4-(3,5-difluoro-phenyl)-2-hydroxy-pentylamino]-cyclohexanone oxime, 4-(3-tert-Butyl-phenyl)-4-[4-(3,5-difluoro-phenyl)-2-hydroxy-pentylamino]-cyclohexanone oxime, 3-[3-[1-(3-tert-Butyl-phenyl)-4-hydroxyimino-cyclohexylamino]1-(3,5-difluoro-benzyl)-2-hydroxy-propylamino]-4-methylamino-cyclobut-3-ene-1,2-dione, and 3-[3-[1-(3-tert-Butyl-phenyl)-4-hydroxyimino-cyclohexylamino]1-(3,5-difluoro-benzyl)-2-hydroxy-propylamino]-4-methoxy-cyclobut-3-ene-1,2-dione.

* * * * *